(12) United States Patent
Wagner et al.

(10) Patent No.: US 10,617,742 B2
(45) Date of Patent: Apr. 14, 2020

(54) METHODS FOR TREATING AND PREVENTING NEUTROPHIL-DERIVED NET TOXICITY AND THROMBOSIS

(71) Applicant: CHILDREN'S MEDICAL CENTER CORPORATION, Boston, MA (US)

(72) Inventors: Denisa D. Wagner, Dover, MA (US); Tobias A. Fuchs, Gunzenbach (DE); Simon De Meyer, Zwevegem (BE); Kimberly Martinod, Boston, MA (US); Alexander Brill, Birmingham (GB); Grace M. Thomas, Marseilles (FR)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/474,012

(22) Filed: Mar. 30, 2017

(65) Prior Publication Data
US 2017/0196945 A1    Jul. 13, 2017

Related U.S. Application Data

(62) Division of application No. 14/119,499, filed as application No. PCT/US2012/039613 on May 25, 2012, now Pat. No. 9,642,822.

(60) Provisional application No. 61/490,877, filed on May 27, 2011.

(51) Int. Cl.
| | |
|---|---|
| *A61K 38/46* | (2006.01) |
| *A61K 39/395* | (2006.01) |
| *A61K 31/155* | (2006.01) |
| *A61K 45/06* | (2006.01) |
| *A61K 38/49* | (2006.01) |
| *A61K 31/166* | (2006.01) |
| *A61M 1/34* | (2006.01) |
| *A61M 1/02* | (2006.01) |

(52) U.S. Cl.
CPC .......... *A61K 38/465* (2013.01); *A61K 31/155* (2013.01); *A61K 31/166* (2013.01); *A61K 38/49* (2013.01); *A61K 39/3955* (2013.01); *A61K 45/06* (2013.01); *A61M 1/0209* (2013.01); *A61M 1/34* (2013.01); *C12Y 301/21001* (2013.01)

(58) Field of Classification Search
None
See application file for complete search history.

(56) References Cited

U.S. PATENT DOCUMENTS

| | | | |
|---|---|---|---|
| 7,612,032 B2 | 11/2009 | Genkin et al. | |
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,796,004 B2 | 8/2014 | Genkin et al. | |
| 8,916,151 B2 | 12/2014 | Genkin et al. | |
| 9,770,492 B2 | 9/2017 | Genkin et al. | |
| 9,845,461 B2 | 12/2017 | Genkin et al. | |
| 2003/0069528 A1 | 4/2003 | Herz et al. | |
| 2004/0048235 A1 | 3/2004 | Budowsky et al. | |
| 2005/0209175 A1 | 9/2005 | Van Amsterdam | |
| 2010/0099074 A1 | 4/2010 | Nolan et al. | |
| 2011/0059460 A1 | 3/2011 | Ewert | |
| 2012/0134974 A1* | 5/2012 | Sehgal | A61K 35/14 424/93.72 |

OTHER PUBLICATIONS

Fung et al., "The Role of Neutrophils in the Pathogenesis of Transfusion-Related Acute Lung Injury", Transfusion Medicine Reviews, vol. 23, pp. 266-283. (Year: 2009).*
Papayannopoulos et al., "Neutrophil elastase and myeloperoxidase regulate the formation of neutrophil extracellular traps", Journal of Cell Biology, vol. 191, pp. 677-691. (Year: 2010).*
Eichler et al., "Engraftment capacity of umbilical cord blood cells processed by either whole blood preparation or filtration." Stem Cells 21(2):208-216 (2003).
Brown et al., "Effects of heparin and related molecules upon neutrophil aggregation and elastase release in vitro", British journal of pharmacology 139: 845-853 (2003).
Deindl et al., Indian J Biochem Biophys. 46(6):461-466 (2009). "New directions in inflammation and immunity: the multifunctional role of the extracellular RNA/RNase system".
DiPasco et al., "Thrombophilic State in Cancer, Part I: Biology, Incidence, and Risk Factors", Journal of Surgical Oncology 104:316-322 (2011).
Eichler et al., Stem Cells. 21(2):208-16 (2003). "Engraftment capacity of umbilical cord blood cells processed by either whole blood preparation or filtration.".
Feng et al., SGH Proceedings 17(2):73-78 (2008). "Ex Vivo Expansion of Haematopoietic Stem/Progenitor Cells for Pooled Cord Blood Transplantation".
Fuchs et al., "Extracellular DNA traps promote thrombosis" PNAS 107(36): 15880-15885 (2010).
Li et al., "PAD4 is essential for antibacterial innate immunity mediated by neutrophil extracellular traps" J. Exp. Med 207(9): 1853-1682 (2010).

(Continued)

*Primary Examiner* — Michelle F. Paguio Frising
(74) *Attorney, Agent, or Firm* — Nixon Peabody LLP; David S. Resnick; Nicole D. Kling

(57) ABSTRACT

Embodiments of the technology described herein are based upon the discoveries that neturophil extracellular traps (NETs) provide a stimulus for thrombus formation and that NETs are present in stored blood products. Accordingly, some embodiments are directed towards methods of treating stored blood products to prevent transfusion-related injuries e.g., preventing transfusion-related acute lung injury (TRALI), by treating blood transfusion products with an anti-Neutrophil Extracellular Trap (NET) compound.

7 Claims, 28 Drawing Sheets
Specification includes a Sequence Listing.

(56) References Cited

OTHER PUBLICATIONS

Massberg et al., Nat Med. 16(8):887-96 (2010). "Reciprocal coupling of coagulation and innate immunity via neutrophil serine proteases.".

* cited by examiner

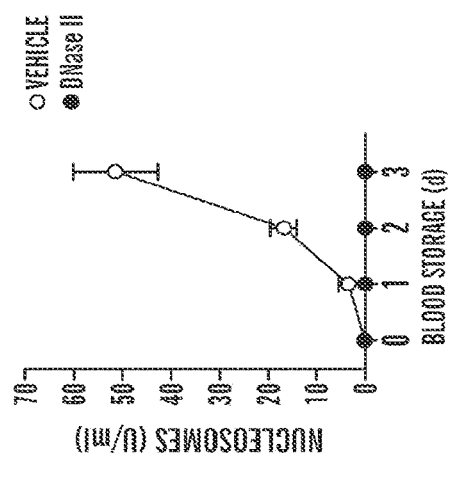
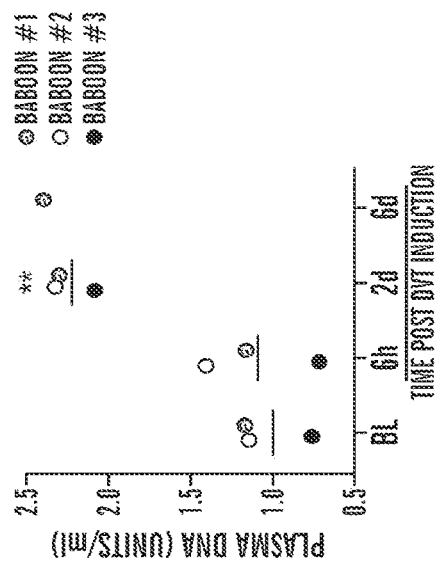
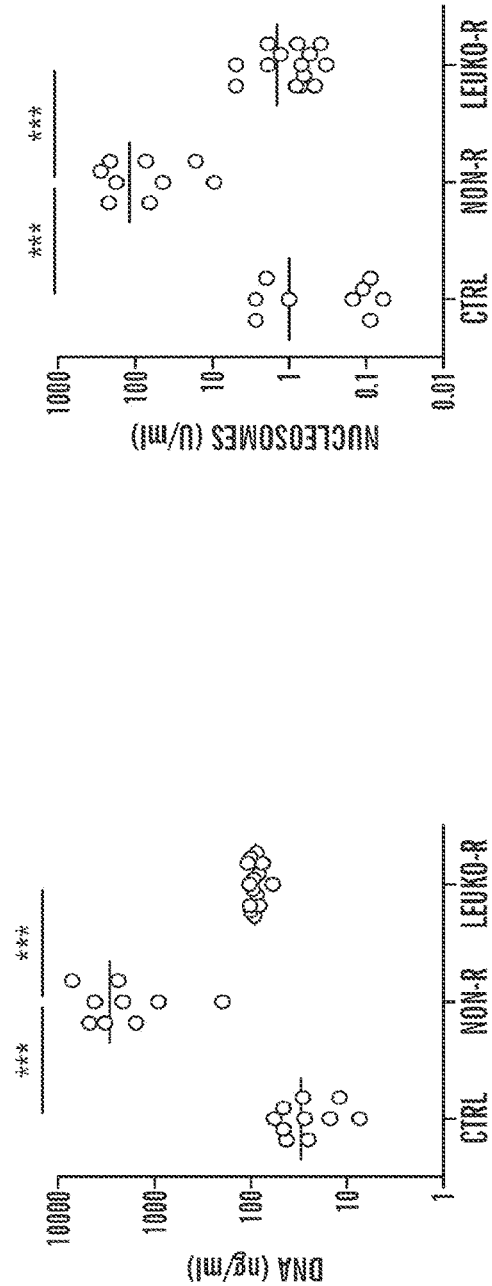

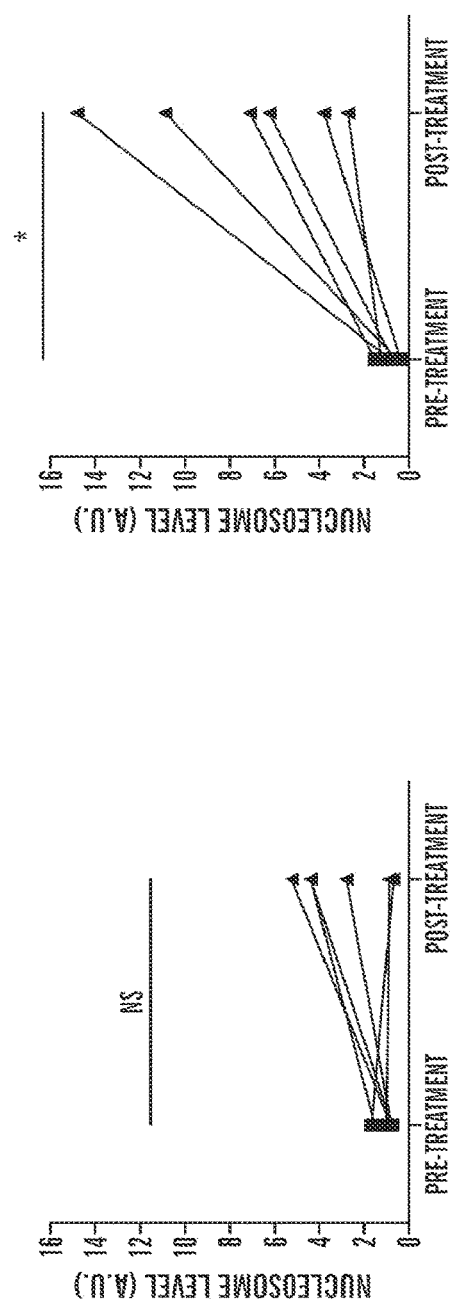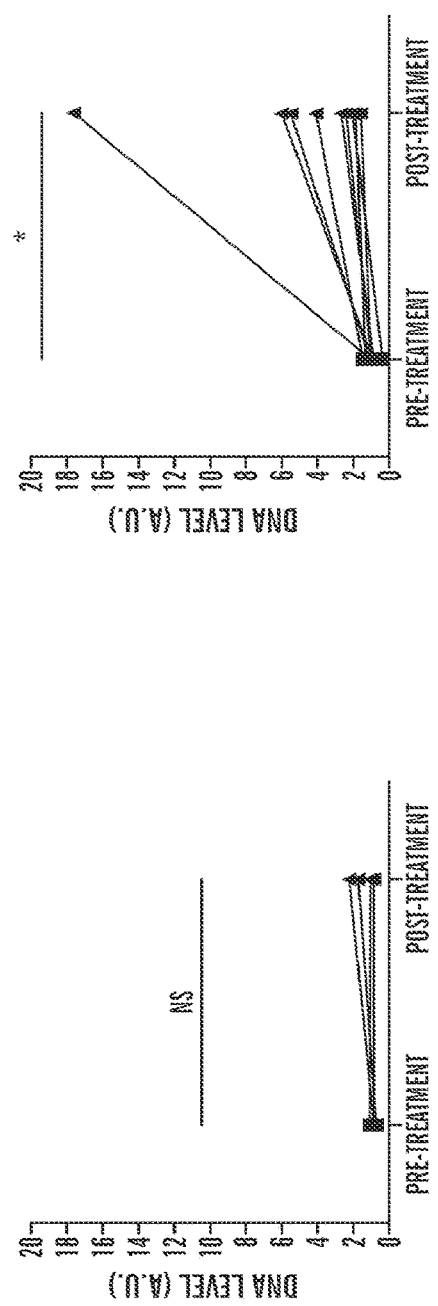

| SCORE | WILD TYPE | DNase-1$^{-/-}$ | P-VALUE |
|---|---|---|---|
| BEDERSON | 1.70±0.40 (N=10) | 2.91±0.16 (N=11) | <0.009 |
| GRIP TEST | 2.50±0.48 (N=10) | 2.09±0.37 (N=11) | =0.050 |

| SCORE | VEHICLE | rhDNase-1 | P-VALUE |
|---|---|---|---|
| BEDERSON | 3.00±0.22 (N=15) | 1.79±0.30 (N=14) | <0.003 |
| GRIP TEST | 1.80±0.31 (N=15) | 3.07±0.35 (N=14) | <0.020 |
| CORNER TEST | 8.42±0.87 (N=12) | 5.46±0.93 (N=13) | =0.030 |

| SCORE | VEHICLE | BWA3 | IgG1 | P-VALUE |
|---|---|---|---|---|
| BEDERSON | 1.70 ± 0.40 (N=13) | 2.00 ± 0.44 (N=7) | 3.00 ± 0.00 (N=7) | 0.12,? |
| GRIP TEST | 1.92 ± 0.43 (N=13) | 3.43 ± 0.30 (N=7) | 2.67 ± 0.21 (N=7) | <0.05, 0.068 |

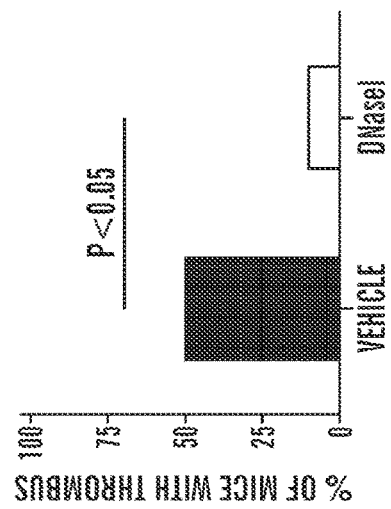
FIG. 13A
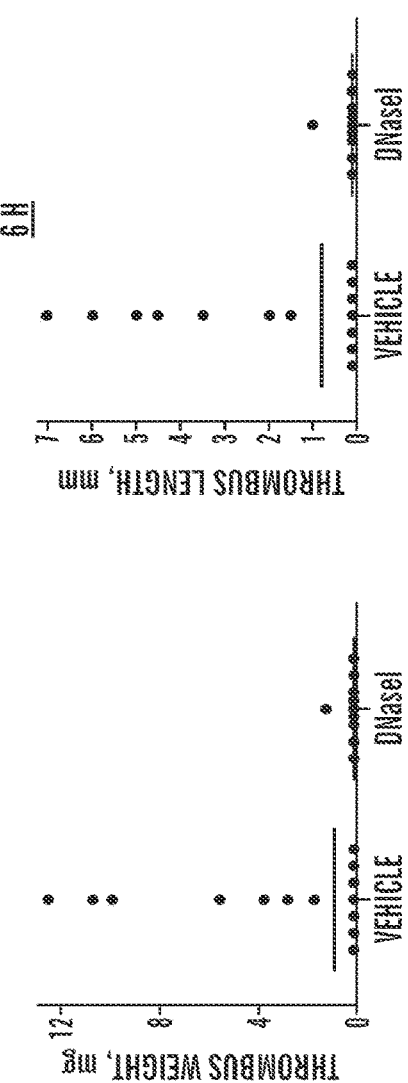
FIG. 13B
FIG. 13C
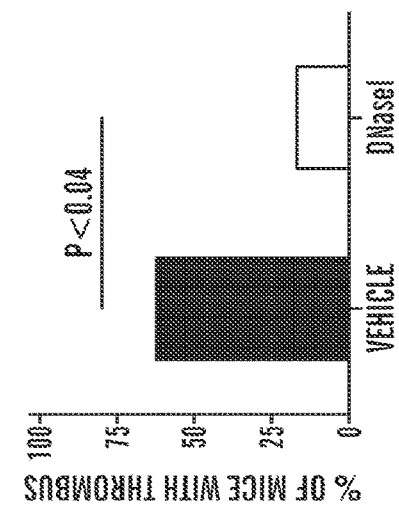
FIG. 13D
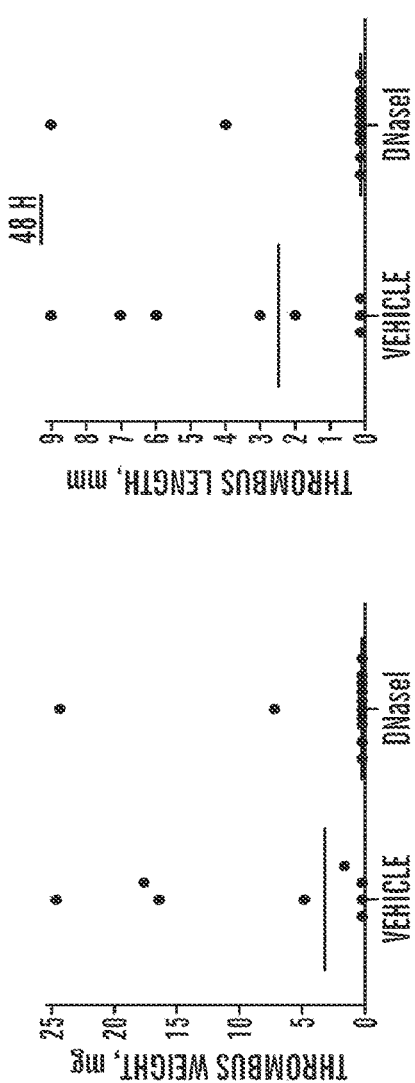
FIG. 13E
FIG. 13F

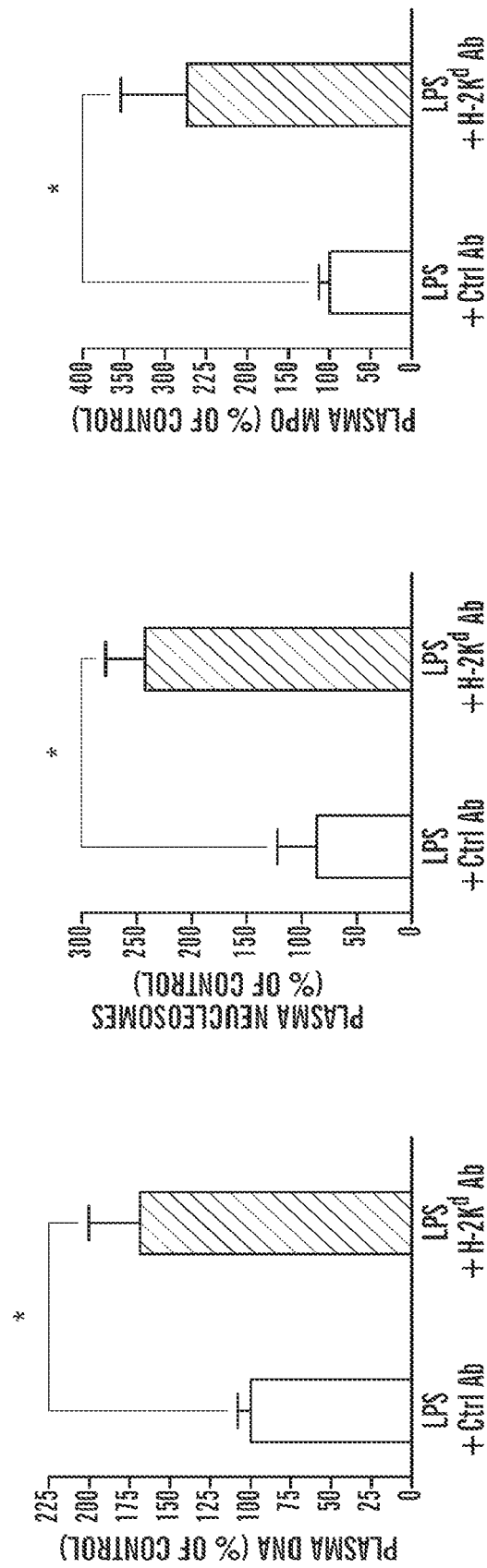

SEQUENCE LISTING

<160> NUMBER OF SEQ ID NOS: 2

<210> SEQ ID NO 1
<211> LENGTH: 2265
<212> TYPE: DNA
<213> ORGANISM: Homo sapiens

<400> SEQUENCE: 1

```
acagccagag ggacgagcta gcccgacgat ggcccagggg acattgatcc gtgtgacccc        60
agagcagccc acccatgccg tgtgtgtgct gggcaccttg actcagcttg acatctgcag       120
ctctgcccct gaggactgca cgtccttcag catcaacgcc tccccagggg tggtcgtgga       180
tattgcccac ggccctccag ccaagaagaa atccacaggt tcctccacat ggcccctgga       240
ccctggggta gaggtgaccc tgacgatgaa agtggccagt ggtagcacag gcgaccagaa       300
ggttcagatt tcatactacg gacccaagac tccaccagtc aaagctctac tctacctcac       360
cggggtggaa atctccttgt gcgcagacat caccgcacc  ggcaaagtga agccaaccag       420
agctgtgaaa gatcagagga cctggacctg gggcccttgt ggacagggtg ccatcctgct       480
```

-continued

```
ggtgaactgt gacagagaca atctcgaatc ttctgccatg gactgcgagg atgatgaagt    540
gcttgacagc gaagacctgc aggacatgtc gctgatgacc ctgagcacga agacccccaa    600
ggacttcttc acaaaccata cactggtgct ccacgtggcc aggtctgaga tggacaaagt    660
gagggtgttt caggccacac ggggcaaact gtcctccaag tgcagcgtag tcttgggtcc    720
caagtggccc tctcactacc tgatggtccc cggtggaaag cacaacatgg acttctacgt    780
ggaggccctc gctttcccgg acaccgactt cccggggctc attaccctca ccatctccct    840
gctggacacg tccaacctgg agctccccga ggctgtggtg ttccaagaca gcgtggtctt    900
ccgcgtggcg ccctggatca tgaccccaa cacccagccc ccgcaggagg tgtacgcgtg    960
cagtattttt gaaaatgagg acttcctgaa gtcagtgact actctggcca tgaaagccaa   1020
gtgcaagctg accatctgcc ctgaggagga gaacatggat gaccagtgga tgcaggatga   1080
aatggagatc ggctacatcc aagccccaca caaaacgctg cccgtggtct tcgactctcc   1140
aaggaacaga ggcctgaagg agtttcccat caaacgcgtg atgggtccag attttggcta   1200
tgtaactcga gggccccaaa caggggtat cagtggactg gactcctttg ggaacctgga   1260
agtgagcccc ccagtcacag tcaggggcaa ggaatacccg ctgggcagga ttctcttcgg   1320
ggacagctgt tatcccagca atgacagccg gcagatgcac caggccctgc aggacttcct   1380
cagtgcccag caggtgcagg ccctgtgaa gctctattct gactggctgt ccgtgggcca   1440
cgtggacgag ttcctgagct tgtgccagc acccgacagg aagggcttcc ggctgctcct   1500
ggccagcccc aggtcctgct acaaactgtt ccaggagcag cagaatgagg ccacggggga   1560
ggccctgctg ttcgaaggga tcaagaaaaa aaaacagcag aaaataaaga acattctgtc   1620
aaacaagaca ttgagagaac ataattcatt tgtggagaga tgcatcgact ggaaccgcga   1680
gctgctgaag cgggagctgg gcctggccga gagtgacatc attgacatcc gcagctcttc   1740
caagctcaaa gagttctcta aggcggaagc tttttttcccc aacatggtga acatgctggt   1800
gctagggaag cacctgggca tccccaagcc cttcgggccc gtcatcaacg ccgctgctg   1860
cctggaggag aaggtgtgtt ccctgctgga gccactgggc ctccagtgca ccttcatcaa   1920
cgacttcttc acctaccaca tcaggcatgg ggaggtgcac tgcggcacca acgtgcgcag   1980
aaagcccttc tccttcaagt ggtggaacat ggtgccctga gcccatcttc cctggcgtcc   2040
tctccctcct ggccagatgt cgctgggtcc tctgcagtgt ggcaagcaag agctcttgtg   2100
aatattgtgg ctccctgggg gcggccagcc ctcccagcag tggcttgctt tcttctcctg   2160
tgatgtccca gtttcccact ctgaagatcc aacatggtc ctagcactgc acactcagtt   2220
ctgctctaag aagctgcaat aaagttttt taagtcactt tgtac                    2265
```

<210> SEQ ID NO 2
<211> LENGTH: 663
<212> TYPE: PRT
<213> ORGANISM: Homo sapiens

<400> SEQUENCE: 2

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Gly Pro Pro Ala Lys Lys Lys Ser Thr Gly

-continued

```
            50                  55                  60
Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                    85                  90                  95

Tyr Gly Pro Lys Thr Pro Pro Val Lys Ala Leu Leu Tyr Leu Thr Gly
                100                 105                 110

Val Glu Ile Ser Leu Cys Ala Asp Ile Thr Arg Thr Gly Lys Val Lys
                115                 120                 125

Pro Thr Arg Ala Val Lys Asp Gln Arg Thr Trp Thr Trp Gly Pro Cys
130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Glu Val Leu Asp Ser Glu Asp
                165                 170                 175

Leu Gln Asp Met Ser Leu Met Thr Leu Ser Thr Lys Thr Pro Lys Asp
                180                 185                 190

Phe Phe Thr Asn His Thr Leu Val Leu His Val Ala Arg Ser Glu Met
                195                 200                 205

Asp Lys Val Arg Val Phe Gln Ala Thr Arg Gly Lys Leu Ser Ser Lys
210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
                260                 265                 270

Asp Thr Ser Asn Leu Glu Leu Pro Glu Ala Val Val Phe Gln Asp Ser
                275                 280                 285

Val Val Phe Arg Val Ala Pro Trp Ile Met Thr Pro Asn Thr Gln Pro
                290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
                340                 345                 350

Glu Ile Gly Tyr Ile Gln Ala Pro His Lys Thr Leu Pro Val Val Phe
                355                 360                 365

Asp Ser Pro Arg Asn Arg Gly Leu Lys Glu Phe Pro Ile Lys Arg Val
370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
                420                 425                 430

Ser Cys Tyr Pro Ser Asn Asp Ser Arg Gln Met His Gln Ala Leu Gln
                435                 440                 445

Asp Phe Leu Ser Ala Gln Gln Val Gln Ala Pro Val Lys Leu Tyr Ser
                450                 455                 460

Asp Trp Leu Ser Val Gly His Val Asp Glu Phe Leu Ser Phe Val Pro
465                 470                 475                 480
```

```
Ala Pro Asp Arg Lys Gly Phe Arg Leu Leu Leu Ala Ser Pro Arg Ser
            485                 490                 495
Cys Tyr Lys Leu Phe Gln Glu Gln Gln Asn Glu Gly His Gly Glu Ala
            500                 505                 510
Leu Leu Phe Glu Gly Ile Lys Lys Lys Gln Gln Lys Ile Lys Asn
            515                 520                 525
Ile Leu Ser Asn Lys Thr Leu Arg Glu His Asn Ser Phe Val Glu Arg
            530                 535                 540
Cys Ile Asp Trp Asn Arg Glu Leu Leu Lys Arg Glu Leu Gly Leu Ala
545                 550                 555                 560
Glu Ser Asp Ile Ile Asp Ile Pro Gln Leu Phe Lys Leu Lys Glu Phe
                565                 570                 575
Ser Lys Ala Glu Ala Phe Phe Pro Asn Met Val Asn Met Leu Val Leu
                580                 585                 590
Gly Lys His Leu Gly Ile Pro Lys Pro Phe Gly Pro Val Ile Asn Gly
            595                 600                 605
Arg Cys Cys Leu Glu Glu Lys Val Cys Ser Leu Leu Glu Pro Leu Gly
            610                 615                 620
Leu Gln Cys Thr Phe Ile Asn Asp Phe Phe Thr Tyr His Ile Arg His
625                 630                 635                 640
Gly Glu Val His Cys Gly Thr Asn Val Arg Arg Lys Pro Phe Ser Phe
                645                 650                 655
Lys Trp Trp Asn Met Val Pro
                660
```

METHODS FOR TREATING AND PREVENTING NEUTROPHIL-DERIVED NET TOXICITY AND THROMBOSIS

CROSS-REFERENCE TO RELATED APPLICATIONS

This application is a divisional of co-pending U.S. application Ser. No. 14/119,499 filed Mar. 25, 2014 which is a 35 U.S.C. § 371 National Phase Entry Application of International Application No. PCT/US2012/039613 filed May 25, 2012, which designates the U.S., and which claims benefit under 35 U.S.C. § 119(e) of U.S. Provisional Application No. 61/490,877 filed May 27, 2011, the contents of which are incorporated herein by reference in their entirety.

FEDERAL FUNDING

This invention was made with federal funding under Grant Nos. P01 HL056949, R01 HL041002, R01 HL095091, and R01 HL102101 awarded by the National Institutes of Health and the National Heart Lung and Blood Institute. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 21, 2013, is named 701039-066002-US_SL.txt and is 9,077 bytes in size.

TECHNICAL FIELD

The technology described herein relates to methods of treating and preventing toxicity and thrombosis caused by leukocyte-derived extracellular DNA traps, such as neutrophil extracellular traps (NETs), in the circulatory system, organs (e.g. lungs), tissues, or in blood products.

BACKGROUND

During an infection, the body's innate immune system will be activated, bringing a number of non-specific defensive mechanisms (as opposed to the specific responses of the adaptive immune system such as antibodies) to bear on the threat. Neutrophils are one of the cell types involved in the innate immune response. They will actively attack a pathogen by producing a respiratory burst; exposing the pathogenic cell to hydrogen peroxide, free radicals, and hypochlorite. Neutrophils are also phagocytic, meaning that they will engulf and then degrade pathogenic cells or damaged host cells; essentially "eating" a unwanted cell in order to destroy it. When neutrophils themselves die, they can release fibers of DNA associated with histones and a number of antimicrobial proteins. These neutrophil extracellular traps (NETs) entangle and kill bacterial pathogens.

SUMMARY

Described herein is the discovery that treatment of subjects with DNase or anti-histone antibodies reduces the level of NETs in the bloodstream and can reduce the incidence and severity of stroke, deep vein thrombosis, and pulmonary thromboembolism. Accordingly, provided herein are methods for treating patients to prevent the accumulation of harmful levels of NETs or degrade existing levels of NETs, thus providing novel methods of treating a number of cardiovascular conditions.

Also described herein is the discovery of the presence of NETs in stored blood products. In addition, the inventors have determined that treatment of stored blood products with DNase reduces the accumulation of NETs in the blood product. Accordingly, in certain embodiments, provided herein are methods and devices for treating accumulations of NETs in both stored blood products and a patient's blood in order to avoid NET-induced cytotoxicity and thrombosis.

In certain embodiments, provided herein are methods of degrading NETs and/or preventing the formation of NETs in both stored blood products and a patient with anti-NET compounds. In certain embodiments, an anti-NET compound is selected from the group consisting of: DNase, RNAse, a histone-degrading enzyme, an inhibitor of chromatin decondensation, an antibody against a component of a NET, or a PAD4 inhibitor.

In certain embodiments the methods provided herein involve the use of at least one anti-NET compound. In further embodiments, the method provided herein involves the use of two or more anti-NET compounds.

In certain embodiments, the method provided herein is directed to the treatment of stored blood products and comprises contacting the blood products with an effective amount of at least one anti-NET compound. In further embodiments, the blood product can be contacted with an anti-NET compound at the time of collecting the blood, at any point during storage of the blood product, or at the time of transfusing the blood products into a patient.

In certain embodiments the anti-NET compound is contained in a composition comprising the anti-NET compound and a pharmaceutically acceptable carrier. In further embodiments the anti-NET compound can be contained in a composition comprising a pharmaceutically acceptable carrier and another compound which would be of use in prolonging the shelf-life, efficacy, or safety of a blood product.

In certain embodiments, contacting a blood product with a single administration of an anti-NET compound decreases the concentration of NETs in a blood product by at least 10%, e.g., by at least 20%, at least 30%, at least 50%, at least 75%, at least 90%, at least 95%, at least 99% or more as compared to the blood product prior to treatment with the anti-NET compound.

In certain embodiments, the anti-NET compound can be added to the blood storage product once it has been collected. In further embodiments, the anti-NET compound can be provided in a blood collection device, a blood storage device, or a blood delivery device. In further embodiments, the anti-NET compound can be administered to a patient when they receive a transfusion of blood products.

In certain embodiments, the blood products can be whole blood, red blood cells, blood plasma, or platelets.

In certain embodiments, the method provided herein is directed to prevention of transfusion-related acute lung injury (TRALI) by contacting blood products with an effective amount of an anti-NET compound.

In certain embodiments, the technology described herein relates to a device containing an effective amount of an anti-NET compound. In further embodiments, the device can be a blood collection device, blood storage device, or blood delivery device.

In certain embodiments, the blood storage device is capable of holding at least 75 mLs of blood product, e.g. at least 75 mL of blood product, at least 100 mL of blood product, at least 200 mL of blood product, at least 500 mL of blood product, at least 1000 mL of blood product, at least 2000 mL of blood product or more.

In certain embodiments, the method provided herein is directed to treatment or prevention of TRALI by administering to a patient an effective amount of anti-NET compound. In certain embodiments, the anti-NET compound is administered by inhalation.

In certain embodiments, the method provided herein is directed to treatment of acute lung injury by administering to a patient an effective amount of anti-NET compound. In certain embodiments, the acute lung injury is caused by embolism, ischemia, hyperoxia, inflammation, sepsis, pancreatitis, oleic acid, acid aspiration, sepsis, oropharyngeal aspiration, and/or exposure to ozone, polytetrafluoroethylene, nickel sulfate, and/or lipopolysaccharide. In certain embodiments, the anti-NET compound is administered by inhalation.

In certain embodiments, the method provided herein is directed to the treatment or prevention of cardiovascular conditions caused by NETs by administering to a patient an effective dose of an anti-NET compound. In a further embodiment the cardiovascular condition is stroke, ischemic reperfusion, myocardial infarction, inflammation, or thrombosis.

In certain embodiments, the effective dose of an anti-NET compound is administered to a patient prophylactically when they are at risk for a cardiovascular condition or exhibiting symptoms, indicators, or markers that a cardiovascular condition is likely to occur. In certain embodiments, the patient is at risk for thrombosis, e.g. DVT.

In certain embodiments, the effective dose of an anti-NET compound is administered to a patient repeatedly.

In certain embodiments the composition comprising at least one anti-NET compound further comprises a pharmaceutically acceptable carrier. In further embodiments, the composition comprising at least one anti-NET compound further comprises another compound which would be useful in treating or preventing a cardiovascular condition.

In certain embodiments, a single administration of an anti-NET compound to a patient decreases the concentration of NETs in the patient's bloodstream by at least 10%, e.g., by at least 20%, at least 30%, at least 50%, at least 75%, at least 75%, at least 90%, at least 95%, at least 99% or more as compared to the blood product prior to treatment with the anti-NET compound.

In one embodiment, a single administration of an anti-NET compound decreases the level of an indicator, symptom, or marker of a cardiovascular condition by at least 10%, e.g., by at least 20%, at least 30%, at least 50%, at least 75%, at least 75%, at least 90%, at least 95%, at least 99% or more as compared to the level of the indicator, symptom, or maker of a cardiovascular condition prior to treatment with the anti-NET compound.

In one embodiment, a single administration of an anti-NET compound to a group of patients decreases the incidence or severity of sepsis, stroke, thrombosis, infarction, ischemia or death by at least 10%, e.g., by at least 10%, by at least 20%, at least 30%, at least 50%, at least 75%, a at least 75%, at least 90%, at least 95%, at least 99% or more as compared to the incidence of sepsis, stroke, or death in a group of patients not administered the anti-NET compound.

In certain embodiments, the method provided herein is directed to assessing a thrombotic condition in a patient comprising determining the level of NETs in a sample obtained from a patient, wherein an increase in the level of NETs as compared to a reference is indicative that a thrombotic event has occurred or is likely to occur.

In certain embodiments, the method provided herein is directed to assessing the efficacy of the administration of an effective dose of at least one anti-NET compound comprising determining the level of NETs obtained from a patient before and after treatment with the anti-NET compound, wherein a reduction in the level of NETs following the treatment with the anti-NET compound is indicative of efficacy.

The details of various embodiments of the invention are set forth in the description below. Other features, objects, and advantages of the invention will be apparent from the description and the drawings, and from the claims.

DESCRIPTION OF THE DRAWINGS

FIG. 1A is an electron micrograph depicting platelets (Pts) attached to a fibrous meshwork of NETs (scale bar, 1 µm). FIG. 1B is an electron micrograph depicting filopods present on the platelets (Pt) attached to NETs, indicating that the platelets were activated (scale bar, 0.5 µm). FIG. 1C shows the quantification of fluorescently-labelled NETs in the presence (open circles) or absence of DNase (closed circles). The x-axis represents the time elapsed and the y-axis shows arbitrary units of NETs. DNase was added to untreated samples after 10 min (arrow). FIG. 1D shows the quantification of fluorescently-labelled platelets in the presence (open circles) or absence of DNase (closed circles). The x-axis represents the time elapsed and the y-axis shows arbitrary units of platelets. DNase was added to untreated samples after 10 min (arrow). Data presented are representative of at least three independent experiments and are shown as mean±SEM, n=3.

FIG. 2A shows the quantification of fluorescently-labelled NETs following 10 minutes of perfusion with blood in the presence or absence of heparin. The x-axis shows the heparin content of the blood and the y-axis shows arbitrary units (A.U.) of NET-DNA. FIG. 2B shows the quantification of fluorescently-labelled platelets following 10 minutes of perfusion of NETs with blood containing fluorescently labeled platelets and with or without heparin added to the blood. The x-axis shows the heparin content of the blood and the y-axis shows arbitrary units (A.U.) of platelets. For FIGS. 2A and 2B data are presented as mean±SEM, n=3; (Student's t test; *P<0.05; P<0.01). FIG. 2C shows the immunodetection of histone H2B (arrow) in the supernatant of NETs treated with DNase (DN) or various concentrations of heparin. A second band (arrowhead) may represent cross reactivity of the antibody or a proteolytic product. Data presented are representative of three independent experiments. FIG. 2D is a graph of the degree of aggregation of platelets treated with thrombin (open circles), human recombinant histone H3 (solid circles), EDTA (solid squares), and heparin (solid triangles). The x-axis shows the elapsed time and the y-axis represents the percentage of light transmission. FIG. 2E is a graph of the degree of aggregation of platelets 3 minutes after addition of various histones or thrombin (Thr). The x-axis shows the treatment and the y-axis depicts the percentage of light transmission. (ANOVA; *P<0.001 compared with histone H1).

FIG. 3A shows a red thrombus (arrow) anchored on two strings (arrowheads) in a flow chamber coated with NETs after perfusion with blood (scale bar, 500 μm). FIG. 3B is an electron micrograph showing individual RBCs attached to NETs (scale bar, 5 μm). FIG. 3C is a graph of the quantification of RBCs (as determined by hemoglobin content) attached to collagen or NETs after perfusion with our without DNase. The x-axis indicates whether the perfusion chamber was coated with collagen or NETs, the y-axis indicates the quantity of attached RBC in arbitrary units (A.U.) and the legend indicates that white bars represent perfusion without DNase while black bars represent perfusion in the presence of DNase. Data presented are representative of at least three independent experiments and presented as mean±SEM, n=3; (ANOVA; P<0.01); n.s.=not significant. FIG. 3D is a graph of the quantification of fluorescently-labelled platelets attached to collagen or NETs after perfusion with our without DNase. The x-axis indicates whether the perfusion chamber was coated with collagen or NETs, the y-axis indicates the quantity of attached platelets in arbitrary units (A.U.) and the legend indicates that white bars represent perfusion without DNase while black bars represent perfusion in the presence of DNase. Data presented are representative of at least three independent experiments and presented as mean±SEM, n=3; (ANOVA; P<0.01); n.s.=not significant.

FIG. 4 is a graph showing that markers of NETs are abundant during baboon deep vein thrombosis (DVT). The y-axis shows the quantity of plasma DNA measured in individual baboons. Baboons #1 and #3 are shown as black circles and babon #2 is shown in white circles. On the x-axis, baseline (BL) levels indicate measurements prior to inducing DVT. Also show are measurements at 6 hours (6 h), 2 days (2 d), and 6 days (6 d) after DVT induction. Bars represent the mean value of groups (n=3; Repeated measures ANOVA; **P<0.01 compared with BL).

FIGS. 5A-5B show graphs depicting that NETs are elevated in stored blood products. FIG. 5A graphs the amount of DNA in leukocyte-reduced (Leuko-R) and non leukocyte-reduced (Non-R) blood. FIG. 5B graphs the amount of nucleosomes in Leuko-R and Non-R blood. The x-axis depicts the type of blood; fresh blood (ctrl), leukocyte-reduced (Leuko-R), or non leukocyte-reduced (Non-R). The y-axis of FIG. 5A shows the amount of DNA detected while the x-axis of FIG. 5B depicts the quantity of nucleosomes detected.

FIG. 6 shows a graph indicating that DNaseII decreased the concentration of NETs in stored blood products. The x-axis shows the amount of time the blood was stored (in days) while the y-axis depicts the amount of nucleosomes detected. Blood treated with DNase is shown in black circles and a solid line while untreated blood (vehicle) is shown in white circles with dashed lines.

FIGS. 7A-7D show graphs indicating that NETs are increased after cerebral ischemia/reperfusion. FIG. 7A shows the level of nucleosomes measured before and after a sham treatment. The x-axis shows the timepoint of measurement and the y-axis shows the level of nucleosomes in arbitrary units (A.U.). Each line represents an individual animal. FIG. 7B shows the level of nucleosomes measured before and after a treatment causing a stroke. The x-axis shows the timepoint of measurement and the y-axis shows the level of nucleosomes in arbitrary units (A.U.). Each line represents an individual animal. FIG. 7C shows the level of DNA measured before and after a sham treatment. The x-axis shows the timepoint of measurement and the y-axis shows the level of DNA in arbitrary units (A.U.). Each line represents an individual animal. FIG. 7D shows the level of DNA measured before and after a treatment causing a stroke. The x-axis shows the timepoint of measurement and the y-axis shows the level of DNA in arbitrary units (A.U.). Each line represents an individual animal.

FIG. 8A shows the scoring of development of the posterior communicating arteries (PComAs). The x-axis shows the genotype of the mice; wildtype (WT) or DNase-1 knock-outs (DNase-1$^{-/-}$). The y-axis shows the development score. FIG. 8B is a graph of the percentage of regional cerebral blood flow (rCBF) before (baseline), during (occlusion), and after (reperfusion) induction of stroke. Timepoints of measurement are shown on the x-axis while the y-axis shows the percentage of regional cerebral blood flow. Wildtype (WT) mice are represented by black boxes and solid lines while DNase-1 knock-outs (DNase-1$^{-/-}$) mice are represented by white boxes and dashed lines. FIG. 8C shows the cell counts of blood from wildtype mice (WT; black bars) or DNase-1 knock-out mice (DNase-1$^{-/-}$; white bars). The cell type is shown on the x-axis. The left-hand y-axis shows the cell counts for leukocytes and neutrophils, while the right-hand y-axis shows the cell counts for platelets.

FIG. 9A shows the size of the infarction (y-axis) in wildtype mice (WT) or DNase-1 knock-out mice (DNase-1$^{-/-}$) (x-axis). FIG. 9B shows scores for neurological function tests which measure the functional severity of injury caused by stroke.

FIG. 10A shows the size of the infarction (y-axis) in control mice (vehicle) and mice treated with rhDNase-1 (rhDNase) (x-axis). FIG. 10B shows scores for neurological function tests which measure the functional severity of injury caused by stroke.

FIG. 12A shows the size of the infarction (y-axis) in control mice (vehicle), mice treated with BWA3 histone-binding antibody (BWA3), and mice treated with control IgG1 (IgG1) (x-axis). FIG. 12B shows scores for neurological function tests which measure the functional severity of injury caused by stroke.

FIGS. 13A-13F show graphs indicating DNase 1 infusion protects mice from flow restriction-induced thrombosis. Wild-type mice underwent IVC stenosis for 6 h (13A-13C) or 48 h (13D-13F). Mice received infusion of either vehicle or DNase 1 (50 1.1 g i.p. and 10 1.tg i.v.) before the surgery (13A-13F) and every 12 h thereafter (13D-13F). (13A, 13D) Thrombus weight and (13B, 13E) thrombus length are presented; horizontal lines represent median. FIGS. 13C and 13F depict the percentage of mice with a thrombus. 6 h vehicle, n=14; 6 h DNase 1, n=10; 48 h vehicle. n=8; 48 h DNase 1, n=12.

FIG. 15A shows the lung epithelium of a normal, healthy mouse lung. FIG. 15B shows the lung epithelium of a mouse in which TRALI has been induced. FIG. 15C shows the lung epithelium of a mouse in which TRALI has been induced and DNase has been administered intranasally.

FIG. 16A shows platelet counts and FIG. 16B shows the protein concentration found in bronchial alveolar lavage (BAL).

FIG. 17A shows a graph depicting quantification of H3Cit+ cells in isolated mouse neutrophils stimulated in vitro. FIG. 17B shows a graph depicting quantification of NETs in isolated mouse neutrophils stimulated in vitro. An unpaired Student's t test was performed to determine significance. Error bars represent mean+/−s.e.m., * p<0.05. PAD4±I±mice, n=4, PAD4+/− mice, n=3, PAD4−/− mice, n=4.

FIG. 18A shows a graph that depicts length of thrombi harvested from 48 h DVT in the venous stenosis model. An unpaired Student's t test was performed to determine significance. FIG. 18B shows a graph that depicts the percentage of thrombi formed in each group. A contingency table and chi-square test was performed to determine significance. Error bars represent medians, *** p<0.001. Wild-type C57Bl/6J mice, n=10, PAD4−/− mice, n=11. Mice deficient in PAD4 do not form DVT.

(FIG. 22C) Percentage of mice that developed a thrombus. Vehicle-treated mice, n=14; histone-treated mice, n=9.

FIG. 23A depicts a graph of the quantification of NETs following anti-HNA-3a antibody treatment by fluorescence microscopy analysis. HNA-3a-positive neutrophils primed with TNF-α were incubated for 180 minutes with PBS (TNF-α+PBS), control IgG purified from healthy volunteer plasma (TNF-α+Ctrl Ab), anti-HNA-3a antibody purified from two donors whose plasma induced TRALI (TNF-α+Ab1 and TNF-α+Ab2) or 25 nM PMA as a positive control (TNF-α+PMA). DNA release was visualized after DNA staining with Hoechst 33342. The experiment was independently performed nine times. Bars represent means±s.e.m. FIG. 23B depicts examples of the fluorescence images quantified in (FIG. 23A). White arrowheads point at selected cells forming NETs. White arrows point at examples of delobulated (large) neutrophil nuclei. Their presence indicates nuclear decondensation, an early step in NETosis. Scale bar, 50 µm. FIG. 23C depicts a graph of the quantification of NETs following anti-HNA-3a F(ab')$_2$ fragment treatment by fluorescence microscopy analysis. HNA-3a-positive neutrophils were incubated and analyzed in the same conditions as in (FIG. 23A) but were also treated with anti-HNA-3a F(ab')$_2$ fragments (TNF-α+F(ab')$_2$ anti-HNA-3a). The experiment was independently performed three times. Bars represent means±s.e.m.

FIGS. 26A-26C depict graphs providing evidence of circulating NET biomarkers in the mouse model of TRALI. Quantification of (FIG. 26A) DNA, (FIG. 26B) nucleosomes and (FIG. 26C) myeloperoxidase concentrations in plasma from a group of mice challenged i.p. with LPS (0.1 mg/kg) and i.v. with an isotype control antibody (1 mg/kg) (LPS+ Ctrl Ab) (n=7, 7 and 4 for FIGS. 26A, 26B and 26C respectively), and from a TRALI group that received both LPS and the anti-H-2K$^d$ antibody (1 mg/kg) (LPS+H-2K$^d$ Ab) (n=7, 7 and 4 for FIGS. 26A, 26B and 26C respectively). Blood was taken 2 hours after antibody injection. * $P<0.05$.

(FIGS. 28A, 28B) Mean (FIG. 28A) and minimum (FIG. 28B) of the arterial oxygen saturation recorded for 20 minutes 2 hours after antibody infusion in control mice (n=17), mice with TRALI (n=9), mice with TRALI that have received DNase 1 as a pretreatment 10 minutes before antibody infusion (n=7; Pre) or as a treatment 90 minutes after antibody infusion (n=9; Post). Mice with TRALI received i.n. either the vehicle-buffer or DNase 1 (50 μg/mouse). Bars represent medians. * $P<0.05$;  $P<0.01$. (FIG. 28C) Shock-like condition was determined by rectal temperature measurement in the mice monitored for arterial oxygen saturation and additional control mice (control group: n=25). Bars represent medians.  $P<0.01$; *** $P<0.005$.

DETAILED DESCRIPTION

Definitions

Figure 1B:
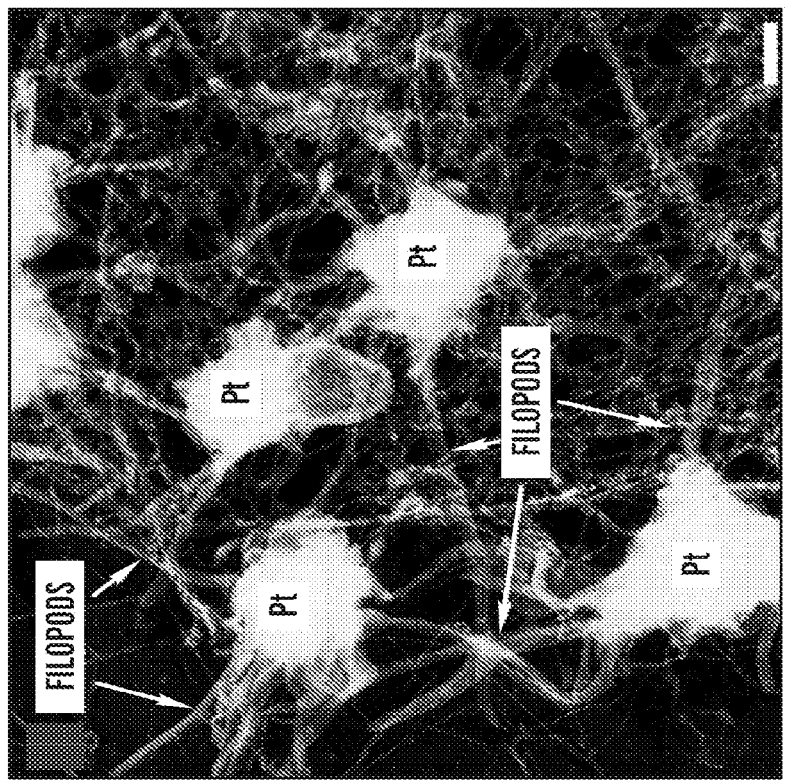
FIGS. 1A-1D show electron micrographs and graphs demonstrating that NETs provide a scaffold for platelet adhesion and aggregation and that DNase degrades NETs and inhibits platelet adhesion.

For convenience, the meaning of certain terms and phrases used in the specification, examples, and appended claims, are provided below. If there is an apparent discrepancy between the usage of a term in the art and its definition provided herein, the definition provided within the specification shall prevail.

Definitions of common terms in cell biology and molecular biology can be found in "The Merck Manual of Diagnosis and Therapy", 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are also be found in Benjamin Lewin, Genes IX, published by Jones & Bartlett Publishing, 2007 (ISBN-13: 9780763740634); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%. In some embodiments, the decrease is up to and including a 100% decrease (e.g. absent level or non-detectable level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, the phrase "contacting a blood product" refers to adding at least one anti-NET compound to a blood product or adding a blood product to at least one anti-NET compound such that the blood product and anti-NET compound can interact with one another.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, the term "antibody" refers to immunoglobulin molecules and immunologically active portions of immunoglobulin molecules, i.e., molecules that contain an antigen binding site that immunospecifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

As used herein in the context of expression, the terms "treat," "treatment," and the like, refer to an decrease in the concentration of NETs in blood products or the bloodstream or decrease in the severity or incidence of cardiovascular conditions as described herein. In the context of the present invention insofar as it relates to any of the conditions recited herein, the terms "treat," "treatment," and the like mean to relieve, alleviate, ameliorate, inhibit, slow down, reverse, or stop the progession, aggravation, deterioriation, progression, anticipated progression or severity of at least one symptom or complication associated with such condition. In one embodiment, the symptoms of a condition are alleviated by at least 5%, at least 10%, at least 20%, at least 30%, at least 40%, or at least 50%.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, the phrase "effective amount" as used in relation to anti-NET compounds in a blood product refers to the amount of anti-NET compound that provides a statistically significant decrease in the concentration of NETs in the blood product as compared to the concentration of NETs in the absence of the compound.

As used herein, the phrase "therapeutically effective amount" or "effective dose" refers to an amount that provides a therapeutic benefit in the treatment, prevention, or management of a cardiovascular condition or a condition caused by NETs in blood products, e.g. an amount that provides a statistically significant decrease in at least one symptom of a cardiovascular condition. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "pharmaceutical composition" refers to the active agent in combination with a pharmaceutically acceptable carrier of chemicals and compounds commonly used in the pharmaceutical industry. The term "pharmaceutically acceptable carrier" excludes tissue culture medium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

As used herein, a "subject" means a human or animal. In one embodiment, the animal is a vertebrate such as a primate, rodent, domestic animal, avian species, fish or game animal. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cardiovascular conditions. In addition, the methods described herein can be used to treat domesticated animals and/or pets. A subject can be male or female. A subject can be one who has been previously diagnosed with a cardiovascular condition, or a subject identified as having one or more complications related to a cardiovascular condition, and optionally, but need not have already undergone treatment for the cardiovascular condition or the one or more complications related to the cardiovascular condition. A subject can also be one who is not suffering from a cardiovascular condition. For example, a subject can be one who exhibits one or more risk factors for a cardiovascular condition, or one or more complications related to a cardiovascular condition. A subject can be asymptomatic for a cardiovascular condition or one or more complications related to a cardiovascular condition. In one embodiment, the subject is selected for having, or being at risk for having, a cardiovascular condition. A subject can also be one who has been diagnosed with or identified as having one or more complications related to a cardiovascular condition, or alternatively, a subject can be one who has not been previously diagnosed with or identified as having one or more complications related to a cardiovascular condition.

NETs

Embodiments of the technology described herein are based on the discovery that NETs provide a previously unrecognized scaffold and stimulus for thrombus formation. Upon activation, neutrophils and other cells undergo a cell death program termed "NETosis" (Fuchs et al., JCB 2007 176:231-241) and release portions of nuclear DNA in the form of nucleosomes in complex with various proteins having antimicrobial activity (Brinkmannn et al. Science 2004 303:1532-5). These complexes are termed NETs and they are capable of entangling microbes and result in degradation of virulence factors and killing of microbes (Brinkmann et al. Science 2004 303:1532-5). Release of NETs from neutrophils has been associated with inflammation during sepsis and noninfectious diseases (Brinkmann et al. Science 2004 303:1532-5; Clark et al. Nature Medicine 2007 13:463-9; Gupta et al., Hum Immnol 2005 66:1146-1154; Kessenbrock et al. Nature Medicine 2009 15:623-5).

As used herein, the term "NET" refers to extracellular complexes of nucleosomes and proteins, e.g. proteins having anti-microbial activity. The nucleosomes may be derived from neutrophils, mast cells, eosinophils, monocytes, or leukocytes.

The results described herein and by the inventors in Fuchs et al. PNAS 2010 107:15880-15885 indicate that NETs are a previously unrecognized link between inflammation and thrombosis. Described herein is the discovery that the histone component of NETs encourages thrombosis by promoting platelet adhesion, activation, and aggregation and data demonstrating that NETs recruit red blood cells, promote fibrin deposition, and induce red thrombus, a marker of venous thrombosis. Herein, it has been further demonstrated that presence of NETS in thrombosis and plasma in a baboon model of deep vein thrombosis. In addition, the studies described herein have demonstrated that DNase or heparin treatment disassembles NETs and abrogates their thrombotic stimulation properties. Accordingly, as described herein, thrombotic conditions can be treated or prevented by the disruption of NETs.

Anti-NET Compounds

Some embodiments are directed to methods and devices for the treatment of stored blood products with anti-NET compounds. Other embodiments are directed to methods for the treatment or prevention of a cardiovascular condition in a patient with anti-NET compounds. As used herein, "anti-NET compounds" can include any compound that degrades or targets for degradation any component of a NET and/or prevents the formation of NETs (e.g. PAD4 inhibitors). Also included are compounds that otherwise inhibit the activity of a NET component or impair the ability of a cell to form a NET, e.g. inhibition of PAD4, which is required for NET formation as described herein. An anti-NET compound can be a nucleic acid (DNA or RNA), small molecule, lipid, carbohydrate, protein, peptide, antibody, or antibody fragment. In some embodiments, an anti-NET compound can be an enzyme, e.g. an enzyme which cleaves and/or degrades, e.g. a nucleic acid, protein, polypeptide, or carbohydrate. As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In certain embodiments an anti-NET compound can be, but is not limited to; DNase, RNase, heparin, an antibody (i.e. an antibody to histones or to a particular histone), a histone degrading enzyme (i.e. mast cell proteinase 1 (Gene ID:1215)), plasmin (Gene ID: 5340), cathepsin D (Gene ID:1509) or activated protein C (Gene ID:5624)) or an inhibitor of chromatin decondensation (i.e. staurosporine, HDAC inhibitors (i.e. M344), PAD4 inhibitors, or elastase inhibitors (i.e. Gelin®)).

In one embodiment, the anti-NET compound is not heparin. In one embodiment, the anti-NET compound is not RNase. In some embodiments, the anti-NET compound is selected from the group consisting of DNase; a histone-degrading enzyme; an inhibitor of chromatin decondensation; an antibody against a component of a NET; an elastase inhibitor; or a PAD4 inhibitor.

Anti-NET compounds can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)). Alternatively, anti-NET compounds are available commercially e.g. Pulmozyme® (Genentech; San Francisco, Calif.), DNase (#D5319 Sigma-Aldrich; St. Louis, M0)(#90083 Thermo Scientific; Rockford, Ill.), RNAse (#R4642 Sigma-Aldrich; St. Louis, Mo.), Heparin® (Celsus; Cincinatti, Ohio), anti-histone antibodies (ab1791, ab8580, ab8898, ab6002, ab1790, ab9053, ab10158, ab71594, ab4269 Abcam; Cambridge, Mass.), mast cell proteinase 1 (5146-SE-010 R&D Systems; Minneapolis, Minn.), thrombin (HCT-0020 Haemalogic Technologies; Essex Junction, Vt.), plasmin (HCPM-0140 Haemalogic Technologies; Essex Junction, Vt.), cathepsin D (1014-AS-010 R&D Systems; Minneapolis, Minn.), activated protein C (AEZ004B Aniara; Mason, Ohio), staurosporine (S4400 Sigma-Aldrich; St. Louis, Mo.), M344 (M5820 Sigma-Aldrich; St. Louis, Mo.) or Gelin® (G0528 Sigma-Aldrich; St. Louis, Mo.).

In certain embodiments, the anti-NET compound is a monoclonal antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Monoclonal antibodies are prepared using methods well known to those of skill in the art. Typically, spleen cells from an animal immunized with a desired antigen are immortalized, commonly by fusion with a myeloma cell (see, Kohler and Milstein (1976) Eur, J. Immunol. 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies, including binding fragments and single chain versions, against predetermined fragments of a NET can be raised by immunization of animals with conjugates of the fragments with carrier proteins. Monoclonal antibodies are prepared from cells secreting the desired antibody. These antibodies can be screened for binding to NETs or their ability to disrupt NETs as described herein. These monoclonal antibodies will usually bind with at least a KD of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunology (4th ed.) Lange Medical Publications, Los Altos, Calif., and references cited therein; Harlow and Lane (1988) Antibodies: A Laboratory Manual CSH Press; Goding (1986) Monoclonal Antibodies: Principles and Practice, (2 d ed.) Academic Press, New York, N.Y.; and particularly in Kohler and Milstein (1975) Nature 256:495-497, which discusses one method of generating monoclonal antibodies. Summarized briefly, this method involves injecting an animal with an immunogen. The animal is then sacrificed any cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," Science 246:1275 1281; and Ward, et al. (1989) Nature 341:544-546. The polypeptides and antibodies of the embodiments described herein may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) Proc. Nat'l Acad. Sci. USA 86:10029-10033.

Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened for ability to disrupt NETs using e.g. methods described herein.

In some embodiments, the anti-NET agent is a PAD4 inhibitor. As used herein, "PAD4" refers to peptidylarginine deiminase 4, an enzyme that converts protein arginine residues to citrulline through a deimination reaction (e.g. SEQ ID NO: 01 (mRNA) and SEQ ID NO: 02 (protein)).

PAD4 is distinguished from other PAD family enzymes by having a nuclear localization signal and thus being able to enter the nucleus and citrullinate histones. As described herein, a loss of PAD4 activity results in decreased NET formation and decreased DVT in mice. A PAD4 inhibitor can decrease the expression or activity of PAD4.

Inhibition of PAD4 can be monitored by measuring PAD4 activity. A non-limiting example of an assay of PAD4 activity is as follows: a candidate inhibitor, in a reaction buffer comprising 100 mM HEPES (pH 7.6), 50 mM NaCl, and 0.5 mM tris(2-carboxyethyl)phosphine (TCEP) can be preincubated with PAD4 (0.2 µM) (in the presence or absence of 10 mM CaCl2) at 37° C. for 15 min prior to the addition of the substrate, N-α-benzoyl-L-arginine ethyl ester (BAEE) (10 mM final concentration) (and 10 mM CaCl2 if CaCl2 was absent in the pre-incubation) to initiate the reaction. After 15 min the reactions can be quenched by flash freezing in liquid nitrogen. For color development, 200 µL of freshly prepared COLDER solution (2.25 M $H_3PO_4$, 4.5 M $H_2SO_4$, 1.5 mM $NH_4Fe(SO_4)$, 20 mM diacetyl monoxime, and 1.5 mM thiosemicarbazide) can be added to each of the quenched reactions, vortexed to ensure complete mixing, and then incubated at 95° C. for 30 minutes. The absorbance at 540 nm can then measured and compared to a citrulline standard curve to determine the concentration of citrulline produced during the course of the reactions (PAD4 deiminates the BAEE substrate). IC50 values can be determined by fitting the concentration-response data to Eq. (1)

Fractional activity of PAD4=1/(1+([candidate inhibitor]/IC50)) (Eq. 1) The concentration of an inhibitor that corresponds to the midpoint (fractional activity=0.5) can be referred to as the IC50. Kits for measuring PAD4 activity are also commercially available, e.g. Cat No. 7000560, Cayman Chemical; Ann Arbor, Mich.

Any inhibitors of PAD4 can be used in the methods described herein. For example, in some embodiments, a PAD4 inhibitor can be a small molecule inhibitor. Small molecule inhibitors of PAD4 are known in the art (see, for example, Luo et al. Biochemistry 2006; U.S. Pat. No. 7,964,636; and U.S. Patent Publications 2007/0276040 and 2011/0142868; each of which is incorporated by reference herein in its entirety) and include, by way of non-limiting example, Cl-amidine and F-amidine. In some embodiments, the PAD4 inhibitor can be specific for PAD4. In some embodiments, the PAD4 inhibitor can be a PAD family inhibitor. PAD4 inhibitors are commercially available, e.g. Cl-amidine (Catalog number 10599, CAS 913723-61-2, Cayman Chemical; Ann Arbor, Mich.) and F-amidine (Catalog number 10610; Cayman Chemica; Ann Arbor, Mich.).

As used herein, "Cl-aminidine" refers to a compound having the structure of formula I:

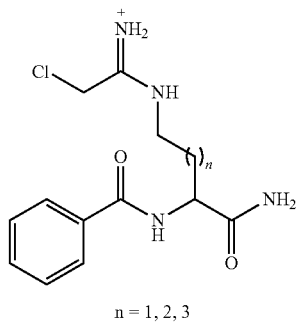

Formula I n = 1, 2, 3

As used herein, "Fl-amidine" refers to a compound having the structure of formula II:

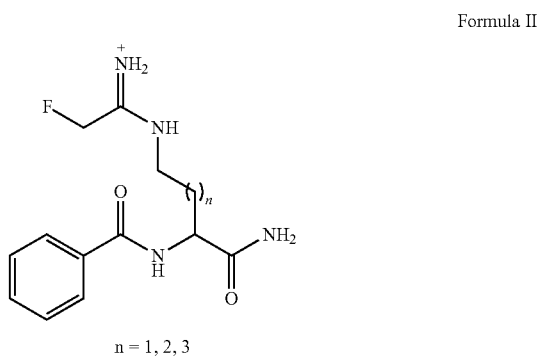

Formula II n = 1, 2, 3

In some embodiments, the PAD4 inhibitor can be an antibody, a polypeptide comprising a fragment of an antibody, or a nucleic acid. Antibodies, and methods of making them are described above herein. PAD4 inhibitors which comprise a nucleic acid can be RNAi agents and/or gene silencing agents. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99% or more of the mRNA level found in the cell without the presence of the miRNA or RNA interference molecule. In one preferred embodiment, the mRNA levels are decreased by at least about 70%, about 80%, about 90%, about 95%, about 99% or more.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the invention, are used interchangeably herein.

As used herein an "siRNA" refers to a nucleic acid that forms a double stranded RNA, which double stranded RNA has the ability to reduce or inhibit expression of a gene or target gene when the siRNA is present or expressed in the same cell as the target gene, sEH. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid which is or which encodes a PAD4 inhibitor further comprises a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. As used herein, the term "viral vector" refers to a nucleic acid vector construct that includes at least one element of viral origin and has the capacity to be packaged into a viral vector particle. The viral vector can contain the PAD4 inhibitor in place of nonessential viral genes. The vector and/or particle may be utilized for the purpose of transferring any nucleic acids into cells either in vitro or in vivo. Numerous forms of viral vectors are known in the art. Vectors useful in the methods described herein can include, but are not limited to, plasmids, retroviral vectors, adenoviral vectors, adeno-associated viral vectors, and pox virus vectors.

The term "replication incompetent" when used in reference to a viral vector means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins for packaging the virus) and viral particles cannot be formed in the patient's cells. The term "transduction" as used herein refers to the use of viral particles or viruses to introduce exogenous nucleic acids into a cell. The term "transfection" as used herein in reference to methods, such as chemical methods, to introduce exogenous nucleic acids, such as the nucleic acid sequences encoding an agent which decreases the activity and/or level of PAD4 as described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

Methods of making RNAi agents which inhibit the expression and/or activity of PAD4 are well known in the art. Sequences complementary to the mRNA encoding PAD4 (i.e. SEQ ID NO: 01) can be used to design RNAi agents as described above herein.

The disruption of NETS can be monitored in vivo or in vitro. In one embodiment, the disruption of NETS is monitored by assessing the level of NET release in stored blood in the presence and absence of a test compound, e.g. by ELISA and/or determination of DNA concentration as described herein. In one embodiment, the ability of a test compound to disrupt NETS is monitored in vivo, e.g. by determining the ability to prevent platelet adhesion and aggregation as described herein and/or determining the ability to prevent thrombosis or protect against stroke as described herein.

Treatment of Stored Blood Products

Certain embodiments are based on the further discovery by the inventors that NETs are present in stored blood products and that treatment of stored blood products with DNase reduces the accumulation of NETs in the blood product. Accordingly, in certain embodiments, provided herein are methods and devices for treating accumulations of NETs in stored blood products in order to avoid NET-induced cytotoxicity and thrombosis. In certain embodiments, provided herein are methods of preventing the release and/or accumulation of NETs and/or degrading NETs in stored blood products with anti-NET compounds.

Increased storage time has been implicated in increased incidents of mortality, pneumonia, post-injury multiple organ failure, hemorrheological disorders, serious infections, TRALI, and adverse microcirculatory hemodynamics. Numerous studies have found that leukodepletion of RBC components reduces the incidence of at least non-hemolytic transfusion reactions, graft-versus-host disease and post-transfusion purpura (Pruss et al., Transfusion and Apheresis Science 2004 30:41-6; Williamson et al., Transfusion 2007 47:1455-67) and improves outcomes in infants with *Bordatella pertussis* infections who receive transfusions (Rowlands et al., Pediatrics 2010 126:816-27). While leukodepletion is currently recognized as a best practice for blood transfusions, the costs involved are considerable and have prevented this safety measure from being universally implemented (van Aken et al. Ned Tijdschr Geneeskd 2000 144:1033-6). Some embodiments provide a cost-effective means for decreasing the risk-benefit ratio of using stored blood products for transfusion by treatment of stored blood products with at least one anti-NET compound.

In certain embodiments, the method provided herein is directed to the treatment of stored blood products and comprises contacting the blood products with an effective amount of at least one anti-NET compound. The blood product to be contacted with an anti-NET compound can be whole blood or a fraction of whole blood, e.g. plasma (platelet-rich or platelet-poor plasma), platelets, or red blood cells.

The phrase "stored blood product," as used herein, refers to a blood product from a donor. In certain embodiments, the blood product will be transfused into a recipient. The blood product can be stored in a blood collection device or blood storage device for any given period of time, e.g. minutes, hours, days, weeks, up to months, prior to use and/or transfusion. In one embodiment, the stored blood product is frozen. In one embodiment, the stored blood product is not frozen.

In certain embodiments, the method provided herein is directed to the treatment of stored blood products at the time the blood is collected. The stored blood product can be contacted with an anti-NET compound during manual or "on-line" collection of the blood product from a donor. During "on-line" collection (i.e. plateletpheresis, plasmapheresis, or leukapheresis), one blood component is removed and the remaining components are returned to the donor during the course of the donation procedure. The stored blood product can be contacted with an anti-NET compound before, during, or after the separation process of "on-line" collection.

Ideally, all blood cell preparations should be from freshly drawn blood and then immediately transfused to the recipient. Thus, in one embodiment, the blood product is treated with an effective amount of at least one anti-NET compound at the time of collecting the blood product from the donor and is shortly thereafter transfused to the recipient.

In one embodiment, the blood product is treated with an effective amount of at least one anti-NET compound at the time of collecting the blood product (e.g. whole blood, plasma, platelets, RBCs) from the donor and is subsequently stored for later use.

In alternative embodiments, the stored blood product can be contacted with an anti-NET compound at any point during storage of the blood product. Whole blood is often separated into its components (e.g. red blood cells (RBCs), platelets, and plasma) for storage.

The stored blood products can be contacted with an anti-NET compound before separation into components. In certain embodiments the stored blood products can be contacted with an effective amount of at least one anti-NET compound during separation into components. Alternatively, the stored blood products can be contacted with an effective amount of at least one anti-NET compound after separation into components. In certain embodiments, the stored blood products can be treated with an effective amount of at least one anti-NET compound prior to transfusion after the blood product has been stored for a period of time. In certain embodiments, an effective amount of at least one anti-NET compound can be added to the blood product through the storage period, e.g. added daily or weekly while the blood product is being stored. In certain embodiments, an effective amount of at least one anti-NET compound is added to RBC blood products which are stored at 1-6° C.

In certain embodiments, a composition containing at least one anti-NET compound is used to reduce the prevalence of NETs in stored blood products by at least 10%, least 20%, at least 40%, at least 50%, at least 75%, at least 90%, or more. For example, a composition containing an anti-NET compound is used to reduce the prevalence of NETs in stored blood products, thereby reducing the occurrence, severity, duration, or number of symptoms associated with one of the following, which are offered by way of example only: mortality, pneumonia, post-injury multiple organ failure, hemorrheological disorders, infections, TRALI, and adverse microcirculatory hemodynamics. By "reduce" in this context is meant a statistically significant decrease in such level. The decrease can be, for example, at least 10%, least 20%, at least 40%, at least 50%, at least 75%, at least 90%, or more.

Any anti-NET compound can be used for treatment of stored blood products. In some embodiments, the anti-NET compound is DNase. In some embodiments, the anti-NET compound is an inhibitor of PAD4.

An effective dose can also be determined by measuring a reduction in mortality, pneumonia, post-injury multiple organ failure, hemorrheological disorders, serious infections, TRALI, and adverse microcirculatory hemodynamics in a population of patients receiving blood products treated with at least one anti-NET compound as compared to patients receiving blood products not treated with an anti-NET compound. The incidence or severity of any of these conditions can be used to determine the therapeutically effective dose. It is well within the ability of one skilled in the art to monitor efficacy of treatment or prevention by measuring any one of such parameters, or any combination of parameters.

Blood products can be treated with any effective amount of an anti-NET compound. In one embodiment, blood products can be treated with about 0.1 U/mL to about 5000 U/mL, i.e., about 0.1 U/mL, about 0.5 U/mL, about 1 U/mL, about 5 U/mL, about 10 U/mL, about 20 U/mL, about 50 U/mL, about 100 U/mL, about 500 U/mL, about 1000 U/mL, or about 5000 U/mL of DNase or another anti-NET compound which is an enzyme. In one embodiment, blood products are treated with about 0.5 mg/kg, about 1.0 mg/kg, about 2.0 mg/kg, about 30 mg/kg, about 40 mg/kg, about 50 mg/kg, about 100 mg/kg, about 500 mg/kg or about 1000 mg/kg of an anti-NET compound. The treatment of the blood product can be repeated, for example, on a regular basis, such as weekly (i.e., every week) for two weeks, three week, four weeks, five weeks, or six weeks or until the blood product is used. Treatment of the blood product with the anti-NET compound can reduce levels of a NETs by at least 10%, at least 15%, at least 20%, at least 25%, at least 30%, at least 40%, at least 50%, at least 60%, at least 70%, at least 80% or at least 90% or more.

Some embodiments further relate to the use of at least one anti-NET compound or a pharmaceutical composition thereof, e.g., for treating stored blood to reduce NETs present therein, in combination with other pharmaceuticals and/or other therapeutic methods, e.g., with known pharmaceutical agents and/or known therapeutic methods, such as, for example, those which can be beneficial to enhance the safety, efficacy or shelf-life of stored blood products. The anti-NET compound and an additional agent can be administered in the same composition or the additional agent can be administered as part of a separate composition or by another method described herein.

Such agents can include anticoagulants or preservatives, for example, CPD, CP2D (Citrate Phosphate Double Dextrose), CPDA-1, CDP/ADSOL®, CDP/Optisol®, AS-3 (Additive Solution 3, Haemonetics Corp Braintree Mass.) and SAG-M. Pathogen inactivation technologies (PITs) can also be added to blood products and include S-59, methylene blue, riboflavin, S-303, and PEN110 (Inactine®). In the case of multi-bag collection and storage sets, additives can be contained in one or more of the bags of that set. In some embodiments, a composition for the treatment of stored blood products comprises an effective amount of at least one anti-NET compound and an anticoagulant, preservative, or PIT.

In certain embodiments, the blood product can be contacted with an anti-NET compound, at the time of transfusing the stored blood products into a patient. In certain embodiments, at least one anti-NET compound is administered to the transfusion patient separately from the transfusion itself.

Some embodiments are directed to a device which contains an effective amount of at least one anti-NET compound. In certain embodiments the device is a blood collection device. In certain embodiments the device is a blood storage device. In certain embodiments the device is a blood delivery device. Blood collection, storage, and delivery devices are typically sterilized.

A "blood collection device" as used herein is any equipment used to collect blood from a donor that will come into contact with the blood product. In certain embodiments the blood collection device is a blood collection bag and/or one or more plastic satellite bags which are integrally connected (e.g. a multiple blood bag system). In further embodiments the device can be, but is not limited to, needles, needle/catheter adapters, spike couplers, and tubes. Collection needles can be ultra-thin walled or normal with a diameter ranging from 15 to 25 gauge or similar. Blood collection tubes link the collection needle to the blood bag(s) and connect to the bags via a jack, coupler or port in the bag. Blood bags can be as described below. Filters can also be incorporated into blood collection devices in order to filter blood during the collection process, such as leukocyte filters for collecting leukocyte-reduced whole blood (Imuflex leukocyte reduction filter, Terumo Somerset, N.J.). In certain embodiments, the effective amount of at least one anti-NET compound can be present within the filter, needle, bag, and/or blood collection tube.

A "blood storage device" as used herein is any equipment which will contact a stored blood product during storage or manipulation of the stored blood product after collection and before transfusion. In certain embodiments, an effective amount of at least one anti-NET compound is provided within a blood storage device. In certain embodiments, the blood storage device is a blood collection bag or bags. In certain embodiments, the blood storage device is a satellite bag. As described herein, blood bags include, but are not limited to, primary or satellite blood bags, typically having volumes of 200, 300, 450, 500 or 600 mL and transfer blood bags typically having volumes of 75, 150, 300, 500, 600, 800, 1000 or 2000 mL. In one embodiment, the blood storage device has a volume to accommodate at least 75 mL, e.g. at least 75 mL of blood product, at least 100 mL of blood product, at least 200 mL of blood product, at least 500 mL of blood product, at least 1000 mL of blood product, at least 2000 mL of blood product or more. Bags can be provided as single, double, triple, quadruple, or quintuple bag sets which are connected by sterile tubing. These bags can be equipped with ports, jacks, or couplers for connecting to other bags, tubing, or for removal of blood or blood products for sampling and testing. One or more of the satellite bags can be a designated platelet storage bag. Multiple bags can be linked via tubes and jacks, couplers and/or ports. Tubes associated with blood collection or delivery bags can have a sampling pouch or diversion arm incorporated for the collection of small volumes of blood to be removed for testing. Such sampling pouches or diversion arms can be included such that the blood sample for testing is collected before or after the primary volume of blood is collected. In certain embodiments, the effective amount of at least one anti-NET compound can be present within the bag, bags, tubing, port, jack, coupler, platelet storage bag, tubes, sampling pouches, and/or diversion arms.

A "blood delivery device" as used herein is any equipment used to transfer blood or a blood product from a storage device to the recipient that will come into contact with the blood product. In certain embodiments, an effective amount of at least one anti-NET compound is provided within a blood delivery device. Blood delivery devices can include, but are not limited to, tubes, needles, needle/catheter adapters, spike couplers, and filters commonly used for the delivery of blood or blood products to a transfusion recipient. Included are 170, 195, 200 micron or smaller mesh filters. In certain embodiments, the effective amount of at least one anti-NET compound can be present within the tubes, needles, needle/catheter adapters, spike couplers, and/or filters.

The anti-NET compound can be present in any of the devices comprising blood collection devices, blood storage devices, or blood delivery devices such that the blood product will be contacted with the anti-NET compound during the normal procedures of collecting, storing, or transfusing the blood product. Some embodiments are directed to a blood bag comprising the bag and an anti-NET compound in the interior of the bag. Some embodiments are directed to a filter device comprising the filter and at least one anti-NET compound. In certain embodiments, the filter device can be integrated into a tube, port or jack of the blood collection, storage, and delivery device.

Methods for Treatment

Described herein are methods of treating conditions associated with NETs, the method comprising administering to a subject an effective amount of at least one anti-NET compound. As used herein, a condition "associated with NETs" can be a condition caused by NETs or aggravated by NETs. Non-limiting examples of conditions associated with NETs include TRALI, acute lung injury, sickle cell disease, cancer, and cardiovascular conditions (e.g. stroke; ischemic reperfusion; myocardial infarction; inflammation; thrombosis; and deep vein thrombosis).

In one embodiment, a method of preventing transfusion related acute lung injury (TRALI) is provided. The method comprises contacting a stored blood product to be used for transfusion (i.e. a blood transfusion product) with an effective amount of at least one anti-NET compound. In some embodiments, the methods described herein comprise providing a person at risk for TRALI with an inhibitor of NETS, such as PAD4, prior to transfusion. As used herein, the term "preventing" as it relates to TRALI refers to amelioration of at least one measurable symptom of TRALI. In one embodiment, the symptom is decreased by at least 10%, at least 20%, at least 30%, at least 40%, or at least 50%.

In one embodiment, a method of treating TRALI is provided. The method comprises administering to a patient an effective amount of at least one anti-NET compound. As used herein, "treating" as it relates to TRALI refers to reducing at least one measurable symptom of TRALI. In one embodiment, the method is for treating a patient with symptoms of TRALI following a transfusion. In one embodiment, the symptom is decreased by at least 10%, at least 20%, at least 30%, at least 40%, or at least 50%. In one embodiment, the anti-NET compound is administered to the bloodstream. In one embodiment, the anti-NET compound is administered intranasally.

TRALI is the leading cause of death among transfusion patients (Stubbs in Sadienberg et al. Transfusion Medicine Reviews 2010 24:305-324). Symptoms of TRALI include, but are not limited to, dyspnea, cyanosis, cough, fever, chills, bilateral pulmonary infiltration, pulmonary edema and hypotension (Stubbs in Sadienberg et al. Transfusion Medicine Reviews 2010 24:305-324). White blood cells have been associated with risk for TRALI and leukodepletion is recommended as a means of reducing the risk of TRALI. At least one study has correlated increased TRALI risk with the age of the blood product (Benjamin in Sadienberg et al. Transfusion Medicine Reviews 2010 24:305-324). Studies in rats were able to induce TRALI with plasma or lipid extracted from stored human RBCs or platelets, but not from plasma or lipid from fresh human RBCs or platelets (Looney in Sadienberg et al. Transfusion Medicine Reviews 2010 24:305-324). Some embodiments provide a means for reducing the incidence and mortality of TRALI, i.e. treatment of stored blood products with at least one anti-NET compound. Not wishing to be bound by theory, treatment of stored blood products with at least one anti-NET compound could circumvent the need to leukodeplete blood product for the prevention of TRALI or other transfusion-related complications such as shortness of breath, fever, etc.

In one embodiment, a method of treating acute lung injury is provided. The method comprises administering to a patient an effective amount of at least one anti-NET compound. As used herein, the term "acute lung injury" refers to a condition characterized by epithelial and endothelial cell perturbation and/or destruction, inflammatory cell influx to the lung tissue, compromised gas exchange, surfactant disruption, pulmonary edema, bilateral pulmonary infiltrates, normal cardiac filling pressures, atelectasis and potentially complete respiratory failure. Acute lung injury can be caused by a number of factors including, but not limited to, embolism, ischemia, hyperoxia, inflammation, sepsis, pancreatitis, oleic acid, acid aspiration, sepsis, oropharyngeal aspiration, lung infection, and/or exposure to ozone, polytetrafluoroethylene, nickel sulfate, and/or lipopolysaccharide.

As used herein, "treating" as it relates to acute lung injury refers to reducing at least one measurable symptom of acute lung injury. In one embodiment, the symptom is decreased by at least 10%, at least 20%, at least 30%, at least 40%, or at least 50%. In one embodiment, the anti-NET compound is administered to the bloodstream. In one embodiment, the anti-NET compound is administered intranasally.

Herein it is demonstrated that NETs represent a link between inflammation and thrombosis by providing a stimulus and scaffold for thrombus formation. In addition, markers of NETs were detected in a thrombus and plasma of baboons subjected to deep vein thrombosis, an example of inflammation-enhanced thrombosis. Furthermore, demonstrated herein is an increase in the level of circulating NETs during cardiovascular stress, ischemia, and reperfusion. Identification of the link of NETs to thrombosis provides NETs as a therapeutic target for treating a variety of conditions involving thrombosis. As described herein, we have determined that treatment of subjects with DNase or anti-histone antibodies reduces the level of NETs in the bloodstream and can reduce the incidence and severity of stroke and deep vein thrombosis. Accordingly, provided herein are methods for treating patients to prevent the accumulation of harmful levels of NETs or degrade existing levels of NETs, thus providing novel methods of treating a number of cardiovascular conditions.

Certain embodiments provide a method for treating or preventing a cardiovascular condition in a patient, i.e. administering a therapeutically effective dose of at least one anti-NET compound. As used herein, the phrase "cardiovascular condition" is intended to include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Also included are any diseases and conditions of the blood vessels which result in insufficient, undesired, or abnormal cardiac function e.g. stroke, thrombosis, ischemia, ischemic reperfusion, vessel occlusion, inflammation etc. As used herein, "cardiovascular condition", is not limited to those conditions resulting from arteriosclerosis. Insufficient or abnormal cardiac function can be the result of disease, injury and/or aging.

In certain embodiments, the method provided herein is directed to the treatment or prevention of cardiovascular conditions caused or contributed to, by NETs by administering to a patient an effective dose of an anti-NET compound. In a further embodiment the cardiovascular condition is stroke, ischemic reperfusion, myocardial infarction, inflammation, and thrombosis. In some embodiments, the cardiovascular condition can be induced by sickle cell disease.

In certain embodiments, the cardiovascular condition to be treated is thrombosis. Clinically, inflammation and infection are linked to thrombosis (Smeeth, L. et al. Lancet 2006 357:1075-9 and Wagner, Arterioscler Thromb Vasc Biol 2005 25:1321-4). Herein, evidence is provided that NETs contribute to this link. Accordingly, some embodiments provide methods for treating or preventing thrombosis in a patient, e.g. methods for treating or preventing cardiovascular conditions complicated by thrombosis. Thrombosis is the occurrence of an clot in a blood vessel at a site of injury to the vessel or an inappropriate blood clot in a blood vessel and depends on the adhesion, activation, and aggregation of platelets. RBCs, whose function in thrombosis is not well defined, are especially abundant in venous thrombi. Final thrombus stability requires scaffolding provided by large polymers, such as fibrin and von Willebrand factor (VWF). Deep vein thrombosis (DVT) is often linked to inflammation and infections. A complication of thrombosis is that the clot will detatch from the blood vessel wall where it formed and lodge somewhere else in the circulatory system, blocking blood flow and causing an embolism.

In certain embodiments, the cardiovascular condition to be treated is ischemia. In another embodiment, the cardiovascular condition to be treated is ischemic reperfusion. As used herein, the term "ischemia" refers to any localized tissue ischemia due to reduction of the inflow of blood. The flow of blood to a tissue can be reduced due to an abnormality in the blood vessels such as thrombosis, embolism, or vasoconstriction. The reduced flow of blood results in local anemia, reduced oxygen levels and eventually damage to the tissue. Ischemia can also be caused by myocardial infarction, acute coronary syndrome, coronary artery bypass surgery, stroke, gastrointestinal ischemia, peripheral vascular disease, and surgical procedures. However, if blood flow is restored (reperfusion) damage can still occur. For example, reperfused postischemic non-necrotic myocardium is poorly contractile and has reduced concentrations of high energy nucleotides, depressed subcellular organelle function and membrane damage that resolves only slowly. A general concern with ischemic reperfusion is that when blood flow returns, white blood cells will activate an inflammatory response upon detecting the tissue damage caused by the ischemic conditions. Furthermore, the recruitment of leukocytes and/or platelets triggered by the original tissue damage can restrict blood flow in smaller capillaries, resulting in a second wave of ischemia.

The term "myocardial ischemia" refers to a subset of ischemia that encompasses circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

In certain embodiments, the cardiovascular condition to be treated is myocardial infarction. A myocardial infarction (i.e. a heart attack) is the death of heart muscle from the sudden blockage of a coronary artery by a blood clot. Coronary arteries are blood vessels that supply the heart muscle with blood and oxygen. Blockage of a coronary artery deprives the heart muscle of blood and oxygen, causing injury to the heart muscle. Injury to the heart muscle causes chest pain and pressure. Inflammation is known to contribute to development of a myocardial infarction, particularly via formation of atherosclerotic plaques. Disruption of a plaque can cause thrombosis and lead to myocardial infarction.

In certain embodiments, the cardiovascular condition to be treated is stroke. Eighty percent of strokes are ischemic, resulting from arterial occlusion of cerebral arteries whereas the remaining 20% are due to intracerebral hemorrhage. Thromboembolic occlusion of intracerebral arteries restricts downstream blood flow, promoting secondary thrombi formation within the cerebral microvasculature.

In certain embodiments, the cardiovascular condition to be treated is thrombosis and the patient has systemic lupus erythematosus (SLE). SLE is an autoimmune disease in which the immune system attacks the patient's body, resulting in inflammation and tissue damage. DNA has been detected on the cell surface of platelets from lupus erythematosus patients (Frampton et al. Clin Exp Immunol 1986 63:621-8). Lupus patients are also prone to develop venous thrombosis (Esmon, Blood Rev 2009 23:225-9) and have a reduced ability to degrade NETs (Hakkim et al., PNAS 2010 107:9813-8). In one embodiment, the patient does not have lupus erythematosus.

In certain embodiments, the condition to be treated is sickle cell disease (SCD) is a condition in which RBCs are deformed and rigid. The altered RBCs are more likely to restrict blood flow at certain points in the circulatory system, leading to a crisis. In SCD patients, a lethal crisis is often precipitated by an infection. In light of the adhesion of RBCs to NETs, as described herein and in Fuchs et al. PNAS 2010 107:15880-15885, anti-NET compounds are contemplated as a treatment for preventing or treating painful occlusive ischemic events and/or a potentially lethal thrombotic event in SCD patients. In certain embodiments, administration of at least one anti-NET compound would be indicated by risk factors. Such risk factors can include, but are not limited to, an infection or an inflammatory condition.

Some embodiments relate to the use of at least one anti-NET compound and compositions containing at least one such anti-NET compound for the treatment of a cardiovascular condition. The compositions described herein can be administered to the patient before, during, or after the occurrence of a cardiovascular event such as a stroke. For example, a composition containing an anti-NET compound is used to reduce the severity, duration, or number of symptoms associated with one of the following, which are offered by way of example only; stoke, ischemic reperfusion, myocardial infarction, inflammation, lupus erythematosus, SCD and thrombosis. By "reduce" in this context is meant a statistically significant decrease in such level. The decrease can be, for example, at least 10%, at least 20%, at least 50%, at least 90% or more.

In some embodiments, the methods and compositions described herein relate to the treatment and/or prevention of deep vein thrombosis (DVT) in a subject, the method comprising administering to a subject an effective dose of at least one anti-NET compound. In some embodiments, the formation of a deep vein thrombosis is prevented. In some embodiments, the progression of one or more signs or symptoms of DVT is prevented, e.g. a thrombus does not increase in size. In some embodiments, the severity of one or more signs or symptoms of DVT is decreased, e.g. a thrombus decreases in size.

In some embodiments, the methods described herein relate to a method of inhibiting the formation of NETs in a subject, the method comprising administering to a patient an effective dose of at least one anti-NET compound. In some embodiments, inhibiting the formation of NETs can comprise preventing the formation of a NET and/or reducing the likelihood that a NET will form in a subject. In some embodiments, inhibiting the formation of NETs can comprise inhibiting the growth or progression of pre-existing NETs and/or reducing the likelihood that a pre-existing NET will grow or progress in a subject. In some embodiments, the method of inhibiting the formation of NETs can reduce the severity of symptoms associated with the development of NETs, e.g. thrombosis. In some embodiments, a subject receiving treatment to inhibit the formation of NETs can be a subject having or diagnosed as having a cardiovascular condition as described above herein. In some embodiments, a subject receiving treatment to inhibit the formation of NETs can be a subject having or diagnosed as having a condition selected from the group consisting of sickle cell disease, TRALI, and acute lung injury. In some embodiments, a subject receiving treatment to inhibit the formation of NETs can be a subject having or diagnosed as having a condition which makes the subject predisposed to thrombosis (i.e. prothrombotic). A condition which makes the subject prothrombotic can be any condition in which the subject is more likely to have or to form a NET as compared to a healthy subject. A non-limiting example of such prothrombotic conditions includes cancer.

Some embodiments relate to the use of at least one anti-NET compound or a pharmaceutical composition thereof as a prophylactic for any of the conditions described herein. A patient exhibiting symptoms, markers, or indications of a condition described herein can be treated with at least one anti-NET compound in order to prevent or reverse the progession of the condition or to lessen the severity of future symptoms, markers, or indicators of the condition.

In certain embodiments the methods provided herein involve the use of at least one anti-NET compound. In further embodiments, the method provided herein involves the use of two or more anti-NET compounds.

In certain embodiments, the effective dose of at least one anti-NET compound is administered to a patient repeatedly.

In certain embodiments, administering a single dose of an anti-NET compound to a patient decreases the concentration of NETs in the bloodstream by at least 10%, e.g., by at least 20%, at least 30%, at least 50%, at least 75%, at least 100%, at least 200% or more as compared to the level of NETs prior to treatment with the anti-NET compound.

In one embodiment, a single administration of an anti-NET compound to a patient decreases the level of an indicator, symptom, or marker of a condition described herein by at least 10%, e.g., by at least 20%, at least 30%, at least 50%, at least 75%, at least 90% more as compared to the level of the indicator, symptom, or maker of the condition prior to treatment with the anti-NET compound.

In one embodiment, a single administration of an anti-NET compound to a group of patients decreases the incidence or severity of stroke, thrombosis, infarction, ischemia, lung injury or death by at least 10%, e.g., by at least 10%, by at least 20%, at least 30%, at least 50%, at least 75%, at least 100%, at least 200% or more as compared to the incidence of sepsis, stroke, lung injury or death in a group of patients not administered the anti-NET compound.

In certain embodiments the composition comprising at least one anti-NET compound further comprises a pharmaceutically acceptable carrier. Some embodiments, relate to the use of at least one anti-NET compound or a pharmaceutical composition thereof, e.g., for treating a patient with a cardiovascular condition, in combination with other pharmaceuticals and/or other therapeutic methods, e.g., with known pharmaceutical agents and/or known therapeutic methods, such as, for example, those which can be beneficial to patients with a condition described herein.

In some embodiments, the further pharmaceutical agent can be an anti-thrombotic. Non-limiting examples of anti-thrombotics include heparin, tPA (e.g. alteplase, reteplase, and tenecteplase), anistreplase, streptokinase, urokinase, coumadins (e.g. warfarin, acenocoumarol, phenprocoumonal, atromentin, and phenindione), idraparinux, fondaparinux, cyclooxygenase inhibitors (e.g. aspririn), adenosine diphosphate receptor inhibitors (e.g. clopidogrel, prasugrel, ticagrelor, and ticlopidine), phosphodiesterase inhibitors (e.g. cilostazol), glycoprotein IIB/IIA inhibitors (e.g. abciximab, eptifibatide, and tirofiban), adenosine reuptake inhibitors, (e.g. dipyridamole), and thromboxane receptor antagonists (e.g. terutroban).

Agents for treating a cardiovascular condition include, without limitation, anti-inflammatory agents, anti-thrombotic agents and/or fibrinolytic agents, anti-platelet agents, lipid reducing agents, direct thrombin inhibitors, glycoprotein IIb/IIIa receptor inhibitors and agents that bind to cellular adhesion molecules and inhibit the ability of white blood cells to attach to such molecules (e.g. anti-cellular adhesion molecule antibodies), angiotensin converting enzyme inhibitor, angiotensin II receptor antagonists, calcium channel blockers, β-adrenergic receptor agonists, vasodilators, diuretics, α-adrenergic receptor antagonists or an antioxidant. One agent which can be used to reduce the risk of a future myocardial disorder in an individual testing positive for antibodies to a cardiac troponin is aspirin (acetylsalicylic acid). Another cardioprotective agent is PPADS (pyridoxal phosphate-6azophenyl-2',4'-disulphonic acid).

Agents for treating lung injury include, without limitation, nitric oxide, anti-inflammatory agents, perfluorocarbon and replacement surfactants. The anti-inflammatories used to treat acute lung injury include, without limitation, ibuprofen, N-acetylcystein, procystein, ketaconazole, methylprednisone, pentoxifylline, and lysofylline.

A number of anti-inflammatory agents are known in the art, non-limiting examples of which are Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone, Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Anti-thrombotic and/or fibrinolytic agents include Plasminogen, prekallikrein, kininogens, Factors XII, XIIIa, plasminogen proactivator, tissue plasminogen activator[TPA], Streptokinase; Urokinase: Anisoylated Plasminogen-Streptokinase Activator Complex; Pro-Urokinase; (Pro-UK); rTPA (alteplase or activase; r denotes recombinant), rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; tenecteplase, retaplase; Trifenagrel; Warfarin; Dextrans.

Anti-platelet agents include P2Y12 inhibitors, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide. Lipid reducing agents include gemfibrozil, cholystyramine, colestipol, nicotinic acid, probucol lovastatin, fluvastatin, simvastatin, atorvastatin, pravastatin, cirivastatin. Direct thrombin inhibitors include hirudin, hirugen, hirulog, agatroban, PPACK, thrombin aptamers. Glycoprotein IIb/IIIa receptor inhibitors are both antibodies and non-antibodies, and include but are not limited to ReoPro (abciximab), lamifiban, eptifibatide and tirofiban.

Angiotensin converting enzyme inhibitors include captopril, enalapril, lisinopril, benazapril, fosinopril, quinapril, ramipril, spirapril, imidapril, and moexipril.

Angiotensin II receptor antagonists include both angiotensin I receptor subtype antagonists and angiotensin II receptor subtype antagonists. Suitable antiotensin II receptor antagonists include losartan and valsartan.

Calcium channel blockers include verapamil, diltiazem, nicardipine, nifedipine, amlodipine, felodipine, nimodipine, and bepridil.

Beta-adrenergic receptor antagonists include atenolol, propranolol, timolol, and metoprolol.

Vasodilators include hydralazine, nitroglycerin, and isosorbide dinitrate.

Diuretics include furosemide, diuril, amiloride, and hydrodiuril.

Alpha-adrenergic receptor antagonists include prazosin, doxazocin, and labetalol.

Antioxidants include vitamin E, vitamin C, and isoflavones.

In certain embodiments for the treatment of stroke, tissue plasminogen activator (tPA) or ADAMTS13, a molecule that cleaves von Willebrand factor can be contemplated. In certain embodiments where a hemorrhage occurs the agent can be an antihypertensive drug, e.g., a beta blocker or diuretic drug, a combination of a diuretic drug and a potassium-sparing diuretic drug, a combination of a beta blocker and a diuretic drug, a combination of an angiotensin-converting enzyme (ACE) inhibitor and a diuretic, an angiotensin-II antagonist and a diuretic drug, and/or a calcium channel blocker and an ACE inhibitor. In another more specific embodiment, the second therapeutic agent is a calcium channel blocker, glutamate antagonist, gamma aminobutyric acid (GABA) agonist, an antioxidant or free radical scavenger.

Agents for treatment of lupus erythematosus include, but are not limited to, nonsteroidal anti-inflammatory drugs (NSAIDs), corticosteroids, antimalarials (i.e. chloroquinine), immunosuppressants (i.e. azathioprine or cyclophosphamide), heparin, aspirin, danazol (Danocrine), vincristine (Oncovin), warfarin, methylprednisolone pulse therapy, dapsone, retinoids, thalidomide (Synovir); methylprednisolone sodium succinate (A-Methapred, Solu-Medrol), methotrexate (Rheumatrex), hydroxychloroquine (Plaquenil), or triamcinolone (Aristospan).

Agents for treatment of SCD include, but are not limited to, prophylactic antibiotics, acetaminophen, NSAIDs, hydroxyurea (Droxia, Hydrea), and agents which inhibit selectins or other adhesion molecules (e.g. TB-1269, OC-229, GMI-1070, and 3-(4-methoxybenzoyl)propionic acid).

The anti-NET compound and the pharmaceutically active agent can be administrated to the subject in the same pharmaceutical composition or in different pharmaceutical compositions (at the same time or at different times). When administrated at different times, an anti-NET compound and the pharmaceutically active agent can be administered within 5 minutes, 10 minutes, 20 minutes, 60 minutes, 2 hours, 3 hours, 4, hours, 8 hours, 12 hours, 24 hours of administration of the other. When the anti-NET compound, and the pharmaceutically active agent are administered in different pharmaceutical compositions, routes of administration can be different. For example, the anti-NET compound is administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and pharmaceutically active agent is administration by a different route, e.g. a route commonly used in the art for administration of said pharmaceutically active agent. In a non-limiting example, an anti-NET compound can be administered orally, while a pharmaceutically active agent can be administrated subcutaneously.

Efficacy of treatment or prevention of disease can be assessed, for example by measuring a marker, indicator, or symptom of cardiovascular and/or pulmonary health or any other measurable parameter appropriate. It is well within the ability of one skilled in the art to monitor efficacy of treatment or prevention by measuring any one of such parameters, or any combination of parameters.

A treatment is evident when there is a statistically significant improvement in one or more parameters of cardiovascular and/or pulmonary health, or by a failure to worsen or to develop symptoms where they would otherwise be anticipated. As an example, a favorable change of at least 10% in a measurable parameter of cardiovascular and/or pulmonary health, and preferably at least 20%, 30%, 40%, 50% or more can be indicative of effective treatment. Efficacy for a given anti-NET compound or formulation of that drug can also be judged using an experimental animal model for a condition described herein as known in the art. When using an experimental animal model, efficacy of treatment is evidenced when a statistically significant increase in a marker is observed.

The dosage ranges for the administration of an anti-NET compound depend upon the form of the compound, its potency, and the extent to which symptoms, markers, or indicators of a condition described herein are desired to be reduced, for example the percentage reduction desired for apoptosis (necrosis), inflammation, or thrombus size. The dosage should not be so large as to cause adverse side effects, such as hyperviscosity syndromes, pulmonary edema, congestive heart failure, and the like. Generally, the dosage will vary with the age, condition, and sex of the patient and can be determined by one of skill in the art. The dosage can also be adjusted by the individual physician in the event of any complication.

Patients can be administered a therapeutic amount of an anti-NET compound, such as 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg or 50 mg/kg. The anti-NET compound can be administered, for example, by intravenous infusion over a period of time, such as over a 5 minute, 10 minute, 15 minute, 20 minute, or 25 minute period. The administration is repeated, for example, on a regular basis, such as hourly for 3 hours, 6 hours, 12 hours or longer or such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the anti-NET compound can reduce levels of a marker or symptom of a condition described herein, e.g., inflammation by at least 10%, at least 15%, at least 20%, at least 25%, at least 30%, at least 40%, at least 50%, at least 60%, at least 70%, at least 80% or at least 90% or more.

Before administration of a full dose of the anti-NET compound, patients can be administered a smaller dose, such as a 5% infusion, and monitored for adverse effects, such as an allergic reaction.

Owing to the effects on cardiovascular and pulmonary health, a composition according to the methods and compositions described herein or a pharmaceutical composition prepared therefrom can enhance the quality of life.

Efficacy Measurement

The efficacy of a given treatment to reduce the negative effects of NETs can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., preventing a stroke, myocardial infarction or crisis episode; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators of, for example as described below. Efficacy can be assessed in animal models of a condition described herein, for example treatment of a mouse following exposure to hypoxic conditions, and any treatment or administration of the compositions or formulations that leads to an decrease in the concentration of NETs in the bloodstream or the decrease of at least one symptom, marker, or parameter of a cardiovascular condition.

Efficacy can be measured by a reduction in any of the symptoms of a condition described herein, for example, a reduction in inflammation (including swelling, redness, or heat) a reduction in ischemia, a reduction in angina, a reduction in pain or a reduction in thrombus number and/or size. Efficacy can also be measured by a failure of an individual to worsen as assessed by hospitalization or need for medical interventions (i.e., progression of the disease is halted or at least slowed).

Another marker of the efficacy of treatment as described herein is survival. Statistical survival rates for specific conditions described herein are well established—when an individual or group of individuals treated according to the methods described herein survives beyond the expected time or at a greater than expected rate, the treatment can be considered effective.

The efficacy of treatment according to the methods described herein can be evaluated by following surrogate or indirect markers of cardiac and/or pulmonary health and function. For example, cardiac cell death, whether by necrosis or apoptosis, is generally accompanied by the release of cardiac enzymes, including cardiac creatine kinase (CK). Assays for cardiac enzymes are routinely used in the diagnosis of myocardial infarction and can be used to monitor the efficacy of cardiac protection according to the methods described herein. A decrease in cardiac enzymes (e.g., a 10% or greater decrease), or a lower level than is normally seen with an infarct of a given size, is indicative of effective treatment. Other markers include, for example, cardiac Troponin T (TnT), which is a marker of cardiac injury that is used as an alternative for CK. In addition, one can perform "echocardiographic analysis of ejection fraction" as a measure of cardiac injury, stabilization after injury or recovery after injury.

Other markers that can be determined include, one or more cardiac troponins, a natriuretic peptide or a natriuretic peptide-related marker, an inflammation marker, D-dimer, cholesterol, homocysteine, adiponectin, sCD40L, myeloperoxidase, and ischemia modified albumin, markers of acute inflammation and so-called proximal inflammatory markers.

Acute inflammatory markers known to the person skilled in the art include C-reactive protein (CRP), fibrinogen, D-dimer, serum amyloid A (SAA), pregnancy-associated polypeptide A (PAPP-A), intercellular adhesion molecules (e.g. ICAM-1, VCAM-1), IL-1-beta, IL-6, IL-8, IL-17 IL-18/IL-18b; TNF-alpha; myeloperoxidase (MPO); TF; monocyte chemoattractant protein 1 (MCP-1); P-selectin; E-selectin; platelet activating factor acetyl hydrolase (PAF-AH); von Willebrand Factor (vWF). Preferred markers of acute inflammation for use in a method described herein are CRP, fibrinogen, D-dimer and SAA, of which CRP and D-dimer are more preferably used. Proximal inflammatory markers are macromolecules situated upstream, i.e. close to or at the ethiopathogenetic origin of the disease event. In particular, they are produced at the site of the coronary heart lesion, preferably at the site of an arterial plaque. Proximal inflammatory markers are in particular associated with the risk that plaques already present in an individual will undergo inflammation, or growth, and with the probability of plaque rupture and thrombus formation. Proximal inflammatory markers are known to the person skilled in the art, and non-limiting examples include pregnancy-associated polypeptide A (PAPP-A), matrix metalloproteinases (MMPs, e.g. MMP-1, -2, -3, -4, -5, -6, -7, -9, -10, -11, -12) and lipoprotein-associated phospholipase A2 (Lp-PLA2).

Other markers, such as anti-double stranded DNA antibodies for systemic lupus erythematosus, can also be used.

The skilled artisan will appreciate that there are many ways to use the measurements of two or more markers in order to improve the diagnostic question under investigation. In a quite simple, but nonetheless often effective approach, a positive result is assumed if a sample is positive for at least one of the markers investigated. This can e.g. be the case when diagnosing an infectious disease, like AIDS, by either detecting a nucleic acid or a polypeptide of the infectious agent or by detecting antibodies to the infectious agent. Frequently, however, the combination of markers is mathematically/statistically evaluated. Preferably the values measured for markers of a marker panel, e.g. an antibody to a cardiac troponin and the level of a cardiac troponin, are mathematically combined and the combined value is correlated to the underlying diagnostic question. Preferably the diagnostic question is the relative risk of developing a cardiovascular condition in the future. Preferably the relative risk is given in comparison to healthy controls. Preferably healthy controls are matched for age and other covariates.

Marker values can be combined by any appropriate state of the art mathematical method. Well-known mathematical methods for correlating a marker combination to a disease or to the risk of developing a disease employ methods like, Discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination as described herein. Preferably the method used in correlating the marker combination described herein e.g. to the absence or presence of myocardial disease is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., J. of Computational and Graphical Statistics, 12 (2003) 475-511; Friedman, J. H., Regularized Discriminant Analysis, JASA 84 (1989) 165-175; Hastie, T., Tibshirani, R., Friedman, J., The Elements of Statistical Learning, Springer Series in Statistics, 2001; Breiman, L., Friedman, J. H., Olshen, R. A., Stone, C. J., (1984) Classification and regression trees, California: Wadsworth; Breiman, L. Random Forests, Machine Learning, 45 (2001) 5-32; Pepe, M. S., The Statistical Evaluation of Medical Tests for Classification and Prediction, Oxford Statistical Science Series, 28 (2003) and Duda, R. O., Hart, P. E., Stork, D. G., Pattern Classification, Wiley Interscience, 2nd Edition (2001).

In some embodiments, an optimized multivariate cut-off is used for the underlying combination of biological markers and to e. g. discriminate patients with low, intermediate and high risk of developing a cardiovascular condition. In this type of multivariate analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease, respectively.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/ (number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45.degree. diagonal line from the lower left corner to the upper right corner. Most plots fall in between these two extremes. (If the ROC plot falls completely below the 45.degree. diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Pharmaceutical Compositions

For administration to a subject or blood product, the compounds can be provided in pharmaceutically acceptable compositions. These pharmaceutically acceptable compositions comprise a therapeutically-effective amount of at least one anti-NET compound described above, formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally. Additionally, compounds can be implanted into a patient or injected using a drug delivery system. Coated delivery devices can also be useful. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; 6,747,014; and 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, binding agents, fillers, lubricants, coloring agents, disintegrants, release agents, coating agents, sweetening agents, flavoring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "pharmaceutically acceptable carrier" or the like are used interchangeably herein.

Many organized surfactant structures have been studied and used for the formulation of drugs. These include monolayers, micelles, bilayers and vesicles. Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S. T. P. Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al. Ann. N.Y. Acad. Sci., 1987, 507, 64; Gabizon et al. PNAS, 1988, 85, 6949; Klibanov et al. FEBS Lett., 1990, 268, 235; Sunamoto et al. Bull. Chem. Soc. Jpn., 1980, 53, 2778; Illum et al. FEBS Lett., 1984, 167, 79; Blume et al. Biochimica et Biophysica Acta, 1990, 1029, 91; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions described herein can be prepared and formulated as emulsions or microemulsions. Emulsions are typically heterogeneous systems of one liquid dispersed in another in the form of droplets usually exceeding 0.1 µm in diameter and have been described in the art. microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, LV., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

In one embodiment, the liposome or emulsion formulation comprises a surfactant. Surfactants find wide application in formulations such as emulsions (including microemulsions) and liposomes. The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285). Suitable surfactants include fatty acids and/or esters or salts thereof, bile acids and/or salts thereof. In certain embodiments, the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

In some embodiments, various penetration enhancers can be employed to effect the efficient delivery of anti-NET compounds across cell membranes. Penetration enhancers can be classified as belonging to one of five broad categories, i.e., surfactants, fatty acids, bile salts, chelating agents, and non-chelating non-surfactants all of which have been described elsewhere (see e.g., Malmsten, M. Surfactants and polymers in drug delivery, Informa Health Care, New York, N.Y., 2002; Lee et al., Critical Reviews in Therapeutic Drug Carrier Systems, 1991, p. 92; Takahashi et al., J. Pharm. Pharmacol., 1988, 40, 252; Touitou, E., et al Enhancement in Drug Delivery, CRC Press, Danvers, Mass., 2006; Muranishi, Critical Reviews in Therapeutic Drug Carrier Systems, 1990, 7, 1-33; El Hariri et al., J. Pharm. Pharmacol., 1992, 44, 651-654; Brunton, Chapter 38 in: Goodman & Gilman's The Pharmacological Basis of Therapeutics, 9th Ed., Hardman et al. Eds., McGraw-Hill, New York, 1996, pp. 934-935; Swinyard, Chapter 39 In: Remington's Pharmaceutical Sciences, 18th Ed., Gennaro, ed., Mack Publishing Co., Easton, Pa., 1990, pages 782-783; Yamamoto et al., J. Pharm. Exp. Ther., 1992, 263, 25; Yamashita et al., J. Pharm. Sci., 1990, 79, 579-583; Jarrett, J. Chromatogr., 1993, 618, 315-339; Katdare, A. et al., Excipient development for pharmaceutical, biotechnology, and drug delivery, CRC Press, Danvers, Mass., 2006; Buur et al., J. Control Rel., 1990, 14, 43-51)

Oral formulations and their preparation are described in detail in U.S. Pat. No. 6,887,906, US Publn. No. 20030027780, and U.S. Pat. No. 6,747,014, each of which is incorporated herein by reference. Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran. The suspension can also contain stabilizers.

A composition comprising at least one anti-NET compound can be administered directly to the airways of a subject in the form of an aerosol or by nebulization. For use as aerosols, an anti-NET compound in solution or suspension may be packaged in a pressurized aerosol container together with suitable propellants, for example, hydrocarbon propellants like propane, butane, or isobutane with conventional adjuvants. An anti-NET compound can also be administered in a non-pressurized form such as in a nebulizer or atomizer.

An anti-NET compound can also be administered directly to the airways in the form of a dry powder. For use as a dry powder, an anti-NET compound can be administered by use of an inhaler. Exemplary inhalers include metered dose inhalers and dry powdered inhalers.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The compositions described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions described herein, such as dyes, flavoring agents, preservatives, antioxidants, opacifiers, thickening agents and stabilizers. However, such materials, when added, should not unduly interfere with the biological activities of the components of the compositions described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the anti-NET compound(s) of the formulation.

As used herein, the phrase "subject in need of at least one anti-NET compound" refers to a subject who is diagnosed with or identified as suffering from, having or at risk for developing a cardiovascular condition or one or more complications related to a cardiovascular condition.

A subject in need of at least one anti-NET compound can be identified using any method used for diagnosis of, e.g. a cardiovascular condition. For example, Doppler ultrasonography can confirm a diagnosis of deep vein thrombosis. Parameters for diagnosis of cardiovascular conditions are known in the art and available to skilled artisan without much effort.

In some embodiments, the methods described herein further comprise selecting a subject identified as being in need of an anti-NET compound. A subject in need of treatment with an anti-NET compound can be a subject having, diagnosed as having, or exhibiting the signs, symptoms, or markers of a condition associated with, caused by, or aggravated by NETs. Non-limiting examples of such conditions include, a cardiovascular condition as described herein (e.g. stroke; ischemic reperfusion; myocardial infarction; inflammation; thrombosis; and deep vein thrombosis), sickle cell disease, TRALI, acute lung injury, and cancer.

A subject in need of an anti-NET compound can be selected based on the symptoms presented, such as symptoms of stroke, thrombosis, or ischemia. Symptoms and markers of cardiovascular conditions are described herein.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred. Murine genetics and surgical techniques have generated a number of mouse models for the study of cardiovascular conditions or mice impaired in the ability to limit the concentration of NETs. Such models can be used for in vivo testing of anti-NET compounds, as well as for determining a therapeutically effective dose. A suitable mouse model is, for example, the DNase$^{-/-}$ mouse described herein or the mouse model of stroke described herein.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The amount of an anti-NET compound which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

The dosage can be determined by a physician and adjusted, as necessary, to suit observed effects of the treatment. Generally, the compositions are administered so that the anti-NET compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. . . . It is to be further understood that the ranges intermediate to the given above are also within the scope of the methods and compositions described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the anti-NET compound. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The desired dose can be administered using continuous infusion or delivery through a controlled release formulation. In that case, the anti-NET compound contained in each sub-dose must be correspondingly smaller in order to achieve the total daily dosage. The dosage unit can also be compounded for delivery over several days, e.g., using a conventional sustained release formulation which provides sustained release of the anti-NET compound over a several day period. Sustained release formulations are well known in the art and are particularly useful for delivery of agents at a particular site, such as could be used with the agents described herein. In this embodiment, the dosage unit contains a corresponding multiple of the daily dose.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the anti-NET compounds described herein can be made using conventional methodologies or on the basis of in vivo testing using an appropriate animal model, as described elsewhere herein.

In some embodiments, pharmaceutical compositions described herein include (a) one or more anti-NET compounds and (b) one or more pharmaceutically effective compounds as described herein.

Assessing a Thrombotic Event

As described herein, the inventors have found that increased levels of NETs are associated with and/or cause hypoxia, stroke, thrombosis, embolism, and lung injury. Accordingly, some embodiments are generally related to assays and methods for assessing whether a patient has experienced or is likely to experience a thrombotic event. As used herein, the term "thrombotic event" refers to a condition caused at least in part, by blood clotting. Such conditions include but are not limited to, stroke, embolism, ischemia, ischemic reperfusion, myocardial infarction, thrombosis, TRALI or acute lung injury. In certain embodiments, the assays and methods are directed to determination of the level of NETs in a biological sample of a subject.

In certain embodiments, the subject may be exhibiting signs or symptoms of a thrombotic event. In certain embodiments, the subject may not be exhibiting signs or symptoms of a thrombotic event but be at risk of developing a thrombotic event due to transfusion, inflammation, infection or other risk factors described herein.

The methods and assays described herein include determining the level of NETs in a sample obtained from a patient and comparing the amount of the NETs in the sample obtained from a patient to an amount of a reference, wherein if the amount of the NETs in the sample obtained from a patient is greater by a statistically significant amount from that of the amount of the reference, the subject has experienced a thrombotic event or is likely to experience a thrombotic event.

The sample obtained from a patient can include, but is not limited to blood or blood products. Blood products in the context of samples obtained from a patient can include, but are not limited to, any component of a patient's blood (e.g. plasma) and/or blood or a component thereof that has been treated or processed (e.g. with an anti-coagulant or preservative).

In some embodiments, the reference can be the level of NETs in a normal healthy subject with no symptoms or signs of a thrombotic event. For example, a normal healthy subject has normal cardiovascular and pulmonary lung function, has not received a transfusion, has no symptoms of inflammation, does not have an infection, and/or is not diagnosed with one of the conditions described herein. The reference can also be a control sample, a pooled sample of control individuals or a numeric value or range of values based on the same. In certain embodiments, wherein the progression of thrombotic event(s) or risk of thrombotic event(s) in a subject is to be monitored over time, the reference can also be a sample taken from the subject at an earlier date. The reference sample can be, but is not limited to blood or blood products. Blood products can include, but are not limited to, any component of a subject's blood (e.g. plasma) and/or blood or a component thereof that has been treated or processed (e.g. with an anti-coagulant or preservative).

In certain embodiments, the patient is determined to have experienced a thrombotic event or be likely to experience a thrombotic event if the level of NETs in the sample obtained from the patient is greater by a statistically significant amount than the level of NETs in a reference. In certain embodiments, the patient is determined to have determined to have experienced a thrombotic event or be likely to experience a thrombotic event if the level of NETs in the sample obtained from the patient is great by at least about 50%, at least about 75%, at least about 100%, at least about 200%, at least about 500%, at least about 1000% or more.

Methods of determining the level of NETs in a sample are described elsewhere herein. In certain embodiments, the level of NETs is determined using labeled DNA detection reagents (i.e. Hoechst 33258 or SytoxGreen), immunodetection of histones, detection of nucelosomes and/or components thereof (i.e. Cell death detection kit, Roche), or electrophoresis of plasma DNA.

In certain embodiments, immunochemical techniques can be used. Immunochemistry is a family of techniques based on the use of an antibody, wherein the antibodies are used to specifically target molecules of interest (i.e. histones or double stranded-DNA). The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

Methods to measure the levels of target molecules detected by immunochemical techniques are well known to a skilled artisan. Such methods to measure target molecule levels include ELISA (enzyme linked immunosorbent assay), western blot, immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques.

A Method of Assessing Efficacy of Anti-NET Treatments

As described herein, the inventors have found that increased levels of NETs are associated with and/or cause hypoxia, stroke, thrombosis, embolism, and lung injury and have provided methods of treating or preventing these disorders by administering one or more anti-NET compounds. Accordingly, some embodiments are generally related to assays and methods for assessing the efficacy of the administration of one of more anti-NET compounds. In certain embodiments, the assays and methods are directed to determination of the level of NETs in a biological sample of a subject.

The methods and assays described herein include determining the level of NETs in samples obtained from a patient before and after treatment with one or more anti-NET compounds, wherein a reduction in the level of NETs following the treatment with the anti-NET compound is indicative of efficacy.

The sample obtained from a patient can include, but is not limited to, blood or blood products. Blood products in the context of samples obtained from a patient can include, but are not limited to, any component of a patient's blood (e.g. plasma) and/or blood or a component thereof that has been treated or processed (e.g. with an anti-coagulant or preservative).

In certain embodiments, the sample obtained from the patient prior to treatment with one or more anti-NET compounds can be obtained at any time prior to administration of the anti-NET compound, for example, about 1 minute prior to treatment, about 10 minutes prior to treatment, about 1 hour prior to treatment, about 1 day prior to treatment, about 1 week prior to treatment, about 2 weeks prior to treatment, about 1 month prior to treatment, or earlier. In certain embodiments, the sample obtained from the patient after treatment with one or more anti-NET compounds can be obtained at any time after administration of the anti-NET compound, for example, about 10 minutes after treatment, about 1 hour after treatment, about 1 day after treatment, about 1 week after treatment, about 2 weeks after treatment, or later.

In certain embodiments, the treatment is determined to have been efficacious if the level of NETs after treatment is lower by a statistically significant amount than the level of NETs prior to treatment. In certain embodiments, the treatment is determined to have been efficacious if the level of NETs is reduced by at least about 10%, at least about 20%, at least about 30%, at least about 40%, at least about 50%, at least about 60%, at least about 70%, at least about 80%, at least about 90%, at least about 95%, at least about 98% or more.

Methods of determining the level of NETs in a sample are described elsewhere herein.

Some embodiments of the technology described herein can be defined as any of the following numbered paragraphs:

1. A device which contains an effective amount of at least one anti-NET compound wherein the device is selected from the group consisting of: a blood collection device, a blood storage device, and a blood delivery device.
2. The device of paragraph 1, wherein the anti-NET compound is DNase.
3. The device of paragraph 1, wherein the anti-NET compound is a PAD4 inhibitor.
4. The device of paragraph 3, wherein the PAD4 inhibitor is selected from the group consisting of:
   Cl-amidine and F-amidine.
5. The device of any of paragraphs 1-4 wherein the device is a blood bag having an interior volume of at least 75 mL and not greater than 2000 mL.
6. The device of any of paragraphs 1-5 wherein the device is a filter contained in a tube which provides a means to move blood to or from a blood bag.
7. A method of treating stored blood products, comprising contacting a blood product with an effective amount of at least one anti-NET compound.
8. The method of paragraph 7, wherein the anti-NET compound is selected from the group consisting of:
   DNase; RNAse; a histone-degrading enzyme; an inhibitor of chromatin decondensation; an antibody against a component of a NET; an elastase inhibitor; and
   a PAD4 inhibitor.
9. The method of paragraph 8, wherein the PAD4 inhibitor is selected from the group consisting of:
   Cl-amidine and F-amidine.
10. The method of any of paragraphs 7-9, wherein the blood product is to be used for transfusion and is not frozen.
11. The method of any of paragraphs 7-10, wherein the blood product is contacted with an effective amount of an anti-NET compound at the time of collecting said blood product from a donor.
12. The method of any of paragraphs 7-11, wherein the effective amount of an anti-NET compound is provided within a blood storage device or blood collection device.
13. The method of any of paragraphs 7-12, wherein the blood product is contacted with an effective amount of an anti-NET compound while the blood product is stored.
14. The method of any of paragraphs 7-13, wherein the effective amount of an anti-NET compound is provided within a blood storage device.
15. The method of any of paragraphs 7-14, wherein the blood product is contacted with an effective amount of an anti-NET compound during the process of transfusing said blood products into a patient.
16. The method of any of paragraphs 7-15, wherein the effective amount of an anti-NET compound is provided within a blood storage device or a blood delivery device.
17. The method of any of paragraphs 7-16, wherein the contacting with an effective amount of an anti-NET compound occurs in vivo by separate delivery of said blood product and said anti-NET compound to the patient's bloodstream.
18. The method of any of paragraphs 7-17, wherein the blood product is selected from the group consisting of: whole blood, red blood cells, blood plasma and platelets.
19. A method of preventing transfusion-related acute lung injury (TRALI), the method comprising contacting blood transfusion products with an effective amount of an anti-NET compound.
20. The method of paragraph 19, wherein the anti-NET compound is selected from the group consisting of:
    DNase; RNAse; a histone-degrading enzyme; an inhibitor of chromatin decondensation; an antibody against a component of a NET; an elastase inhibitor; and
    a PAD4 inhibitor.
21. The method of paragraph 20, wherein the PAD4 inhibitor is selected from the group consisting of:
    Cl-amidine and F-amidine.
22. A method of treating or preventing a condition associated with NETs comprising administering to a patient an effective dose of at least one anti-NET compound.
23. The method of paragraph 22, wherein the anti-NET compound is selected from the group consisting of:
    DNase; RNAse; a histone-degrading enzyme; an inhibitor of chromatin decondensation; an antibody against a component of a NET; an elastase inhibitor; and
    a PAD4 inhibitor.
24. The method of paragraph 23, wherein the PAD4 inhibitor is selected from the group consisting of:
    Cl-amidine and F-amidine.
25. The method of any of paragraphs 22-24, wherein said condition is a cardiovascular condition selected from the group consisting of:
    stroke; ischemic reperfusion; myocardial infarction; inflammation; thrombosis; and
    deep vein thrombosis.
26. The method of any of paragraphs 22-24, wherein said condition is a condition selected from the group consisting of:
    sickle cell disease, TRALI and acute lung injury.
27. The method of any of paragraphs 22-26, wherein said effective dose of anti-NET compound is administered prophylactically.
28. The method of any of paragraphs 22-27, wherein said effective dose of anti-NET compound is given repeatedly.
29. The method of any of paragraphs 22-28, wherein the subject is further administered an anti-thrombotic treatment.
30. The method of paragraph 29, wherein the anti-thrombotic treatment is selected from the group consisting of:

heparin; tPA; anistreplase; streptokinase; urokinase; a coumadin; warfarin;
idraparinux; fondaparinux; aspririn; a adenosine diphosphate receptor inhibitor; a
phosphodiesterase inhibitor; a glycoprotein IIB/IIA inhibitor; a adenosine reuptake inhibitor; and a thromboxane receptor antagonist.

31. A method for treating or preventing deep vein thrombi in a subject, the method comprising:
administering to a subject an effective dose of at least one anti-NET compound.

32. The method of paragraph 31, wherein the anti-NET compound is selected from the group consisting of:
DNase; RNAse; a histone-degrading enzyme; an inhibitor of chromatin decondensation; an antibody against a component of a NET; an elastase inhibitor; and
a PAD4 inhibitor.

33. The method of paragraph 32, wherein the PAD4 inhibitor is selected from the group consisting of:
Cl-amidine and F-amidine.

34. The method of any of paragraphs 31-33, wherein said effective dose of anti-NET compound is administered prophylactically.

35. The method of any of paragraphs 31-34, wherein said effective dose of anti-NET compound is given repeatedly.

36. A method of any of paragraphs 31-35, wherein the subject is further administered an anti-thrombotic treatment.

37. The method of paragraph 36, wherein the anti-thrombotic treatment is selected from the group consisting of:
heparin; tPA; anistreplase; streptokinase; urokinase; a coumadin; warfarin;
idraparinux; fondaparinux; aspririn; a adenosine diphosphate receptor inhibitor; a
phosphodiesterase inhibitor; a glycoprotein IIB/IIA inhibitor; a adenosine reuptake inhibitor; and a thromboxane receptor antagonist.

38. A method of inhibiting the formation of NETs in a subject, the method comprising administering to a patient an effective dose of at least one anti-NET compound 39. The method of paragraph 38, wherein the anti-NET compound is selected from the group consisting of:
DNase; RNAse; a histone-degrading enzyme; an inhibitor of chromatin decondensation; an antibody against a component of a NET; an elastase inhibitor; and
a PAD4 inhibitor.

40. The method of paragraph 39, wherein the PAD4 inhibitor is selected from the group consisting of:
Cl-amidine and F-amidine.

41. The method of any of paragraphs 38-40, wherein the subject has a cardiovascular condition selected from the group consisting of:
stroke; ischemic reperfusion; myocardial infarction; inflammation; thrombosis; and
deep vein thrombosis.

42. The method of any of paragraphs 38-41, wherein the subject has a condition selected from the group consisting of:
sickle cell disease, TRALI and acute lung injury.

43. The method of any of paragraphs 38-41, wherein the subject has cancer.

44. The method of any of paragraphs 38-43, wherein said effective dose of anti-NET compound is administered prophylactically.

45. The method of any of paragraphs 38-44, wherein said effective dose of anti-NET compound is given repeatedly.

46. The method of any of paragraphs 38-45, wherein the subject is further administered an anti-thrombotic treatment.

47. The method of paragraph 46, wherein the anti-thrombotic treatment is selected from the group consisting of:
heparin; tPA; anistreplase; streptokinase; urokinase; a coumadin; warfarin;
idraparinux; fondaparinux; aspririn; a adenosine diphosphate receptor inhibitor; a
phosphodiesterase inhibitor; a glycoprotein IIB/IIA inhibitor; a adenosine reuptake inhibitor; and a thromboxane receptor antagonist.

48. A method of assessing a thrombotic condition in a patient comprising determining the level of NETs in a sample obtained from a patient, wherein an increase in the level of NETs as compared to a reference is indicative that a thrombotic event has occurred or is likely to occur.

49. A method of assessing the efficacy of the administration of an effective dose of at least one anti-NET compound comprising determining the level of NETs in a sample obtained from a patient before and after treatment with the anti-NET compound, wherein a reduction in the level of NETs following the treatment with the anti-NET compound is indicative of efficacy.

EXAMPLES

Example 1

NETs Promote Thrombosis

The interaction between NETs and blood was studied using NETs isolated from human neutrophils. Blood samples were obtained from healthy donors who had not taken any medication for at least 10 day. Platelets and neutrophils were prepared from ACD-blood (Brill A, et al. Cardiovasc Res 2009 84(1):137-144) or EDTA-blood (Fuchs et al., J Cell Biol 2007 176:231-241), respectively. Neutrophils were seeded into flow chambers (μ-Slide IV, IBIDI) at 0.5 to $1 \times 10^7$ cells/mL. NET formation by the majority of cells was induced by phorbol 12-myristate 13-acetate (PMA, 50 nM, 4 h; Sigma Aldrich) or glucose oxidase (GO, 1 U/mL, 4 h; Worthington Biochem), as previously described (Brill A, et al. Cardiovasc Res 2009 84(1):137-144). PMA-induced NETs were used for initial observations. Other experiments were done with GO-induced NETs. NETs were washed and blocked with 1% BSA (Calbiochem). NET-DNA was stained with 1 μg/mL Hoechst 33258 (Invitrogen) for 15 min at 37° C. or SytoxGreen (1 μM, Invitrogen). Washed platelets were loaded with fluorescent Calcein-AM (2.5 μg/mL, 10 min, 37° C.; Invitrogen) or platelets in whole blood were labeled with Rhodamine 6G (5 μg/mL, 10 min, 37° C.; Sigma). Fluorescent images were acquired by a Zeiss Axiovert 200 inverted fluorescence microscope in conjunction with a monocrom camera (AxioCam MRm). Colors for fluorescence channels were assigned using Axiovision software. Fluorescent areas in images were quantified using ImageJ software.

NETs were induced on glass coverslips and perfusion was performed using a parallel-plate flow chamber system (Glycotech). NETs were perfused with platelets suspended in plasma at a shear rate of 200/s or 900/s and 37° C. using a peristaltic pump and observed to be avidly adhering platelets. NETs were washed and fixed with 2.5% glutaraldehyde and electron microscopy was performed. Electron micrographs showed platelet accumulation (labelled Pts in FIG.

Figure 1A:
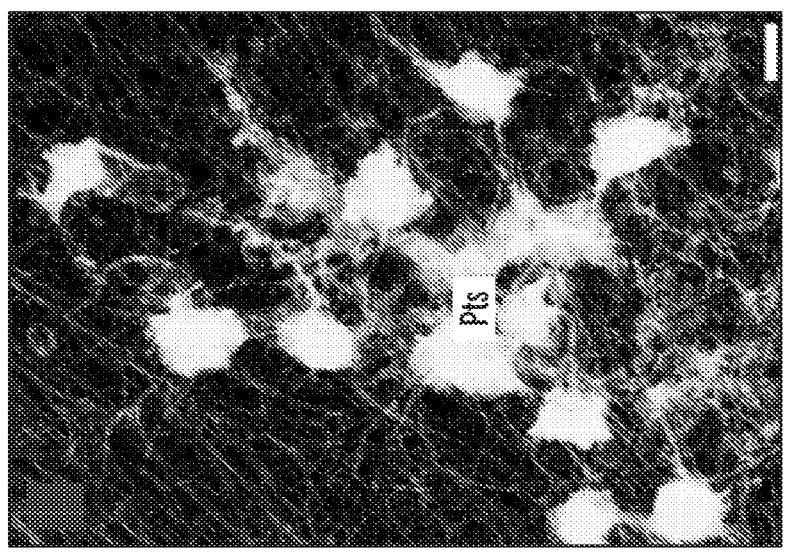

1A) on a fibrous meshwork of NETs (FIG. 1A; scale bar=1 µm) and filopod formation indicated that platelets (labelled Pt in FIG. 1B) adherent on NETs were activated (FIG. 1B; scale bar=0.5 µm). NETs were also perfused with ACD-anticoagulated blood supplemented with the irreversible thrombin inhibitor PPACK-Dihydrochloride (100 µM; Calbiochem) and recalcified by addition of 2 mM $CaCl_2$. Perfusion at high shear rates (900/s) or low, typically venous shear rates (200/s) resulted in time-dependent platelet aggregation. Cells firmly attached to collagen or NETs were lysed with 100 µL of 0.5% Triton ×100 in water. Hemoglobin content was measured using the method of Drabkin (Drabkin PNAS 1971 68:609-13). To quantify platelets, Rhodamine-6G fluorescence of the sample was analyzed using a fluorometer.

Figure 1C:
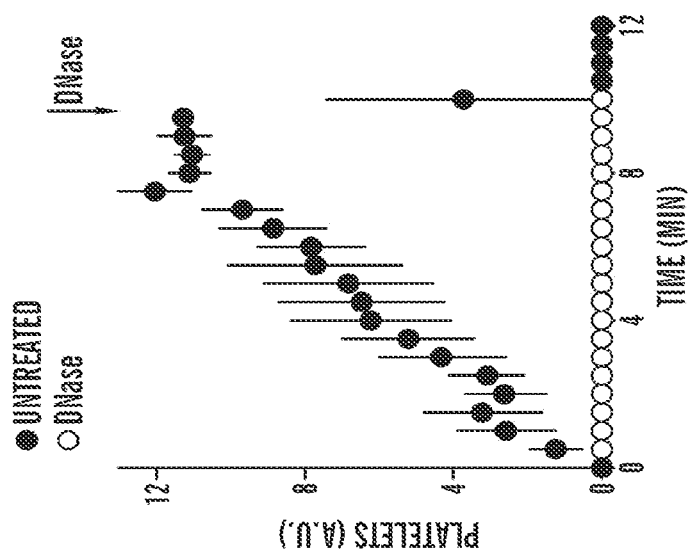
Figure 1D:
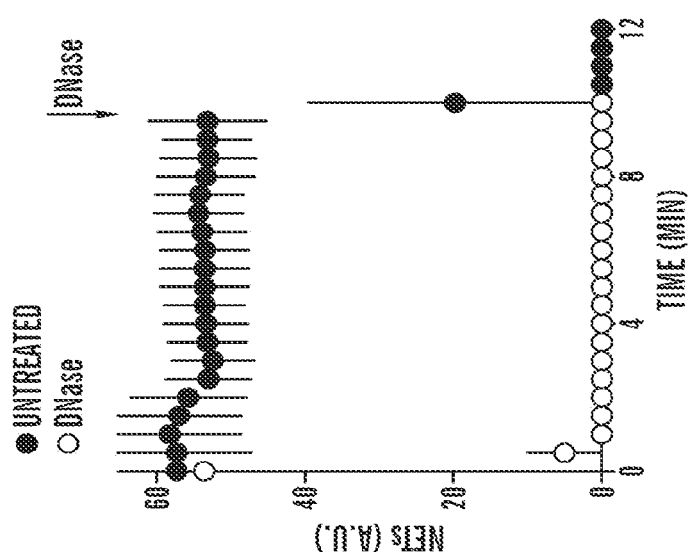

Strings of NETs aligned in the direction of flow and, importantly, NETs were not a static surface but moved in three dimensions. Within 1 min from onset of perfusion, small platelet aggregates appeared on NETs. Platelet adhesion and aggregation on NETs increased over the next 9 min. DNase (100 U/mL; Worthington Biochem) simultaneously removed NETs and platelets, indicating that platelets were indeed attached to NETs. Quantification showed that areas covered by NETs were constant (FIG. 1C; closed circles), whereas platelets adhered and aggregated in a time-dependent manner (FIG. 1D; closed circles). Both platelet aggregates and NETs were removed by DNase and 10 minutes after the beginning of perfusion (FIGS. 1C and 1D). When blood was supplemented with DNase at the beginning of the perfusion, NETs were degraded rapidly (FIG. 1C; open circles) and platelet aggregates did not form (FIG. 1D; open circles). Thus, NETs were the only prothrombotic substrate in these experiments. FIGS. 1C and 1D show data that are representative of at least three independent experiments and are shown as mean±SEM, n=3. AU means arbitrary units.

Figures 2A, 2B, 2C:
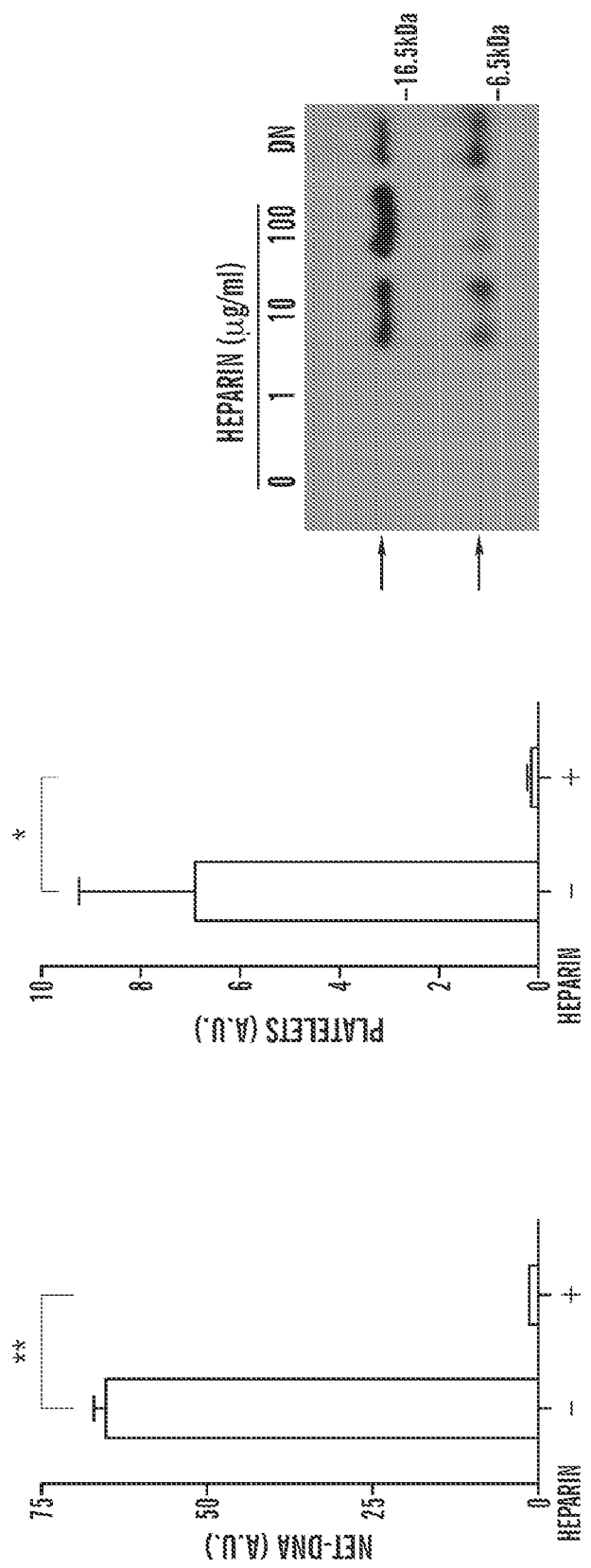
FIGS. 2A-2E shows graphs and a western blot demonstrating that heparin dismantles NETs and prevents histone induced platelet aggregation.

Heparin (100 µg/mL; Sigma) almost completely dismantled NETs when the NETs were perfusion with heparinized blood (FIG. 2A). In addition, heparin (10 µg/mL, Sigma) removed platelet aggregates from NETs (FIG. 2B) as efficiently as DNase (in FIGS. 2A-2B, data are presented as mean±SEM, n=3; Student's t test; *P<0.05; **P<0.01). The effect of heparin was also observed in medium, indicating a direct interaction of heparin with the NETs. Heparin has high affinity for histones (Pal et al., Thromb Res 1983 31:69-79) and releases histones from chromatin (Napirei et al. FEBS J 2009 276:1059-1073). Consequently, incubation of NETs under static conditions with heparin or DNase alone released histones to the culture supernatant (FIG. 2C; arrow indicates H2B; arrowhead may represent cross reactivity; DN=DNase). This result indicates that heparin removes histones from the chromatin fibers that built the backbone of NETs and this leads to the destabilization of NETs.

Figure 2E:
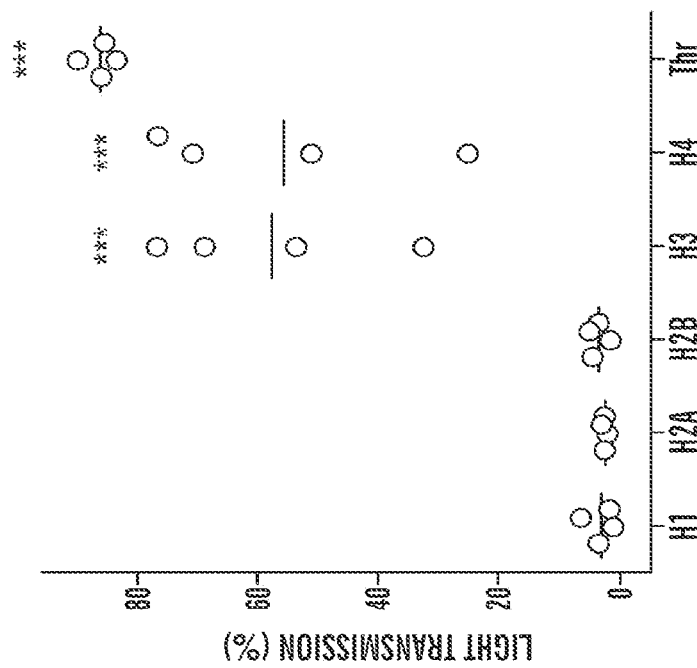
Figure 2D:
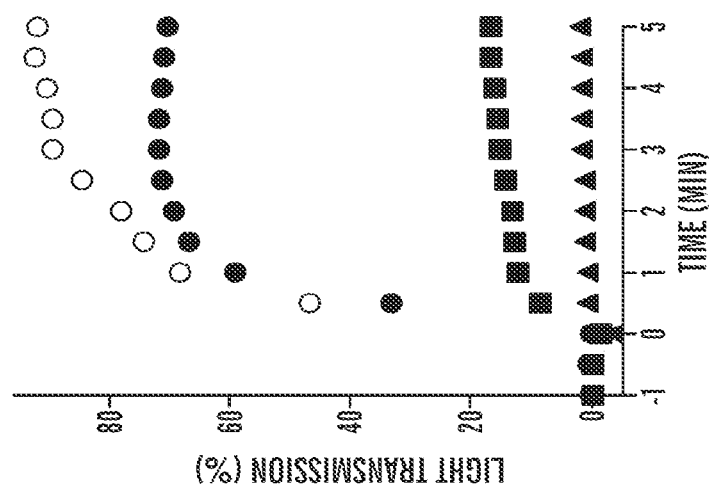

The possibility of a direct interaction between platelets and histones was examined. As shown in FIGS. 2D and 2E, histones were sufficient to induce platelet aggregation. Incubation of platelets with histones H3 (5 µg/mL; NEB; solid circles; FIG. 2E) and H4 stimulated aggregation, whereas histones H1, H2A, and H2B had no such effect (FIG. 2E). Thrombin (0.5 U/mL; open circles in FIG. 2D) and heparin (solid triangles in FIG. 2D) served as a positive control in these experiments. Aggregation in response to histone H3 (FIG. 2D) and H4 (data not shown) was inhibited by EDTA (5 mM; solid squares in FIG. 2D) which excluded platelet agglutination caused by the positive charge of histones. Heparin completely abolished platelet response to these histones (FIG. 2E; ANOVA; ***P<0.001 compared with histone H1). Dissociating NETs and inhibiting histones could add to the antithrombotic effects of heparin.

Figure 3B:
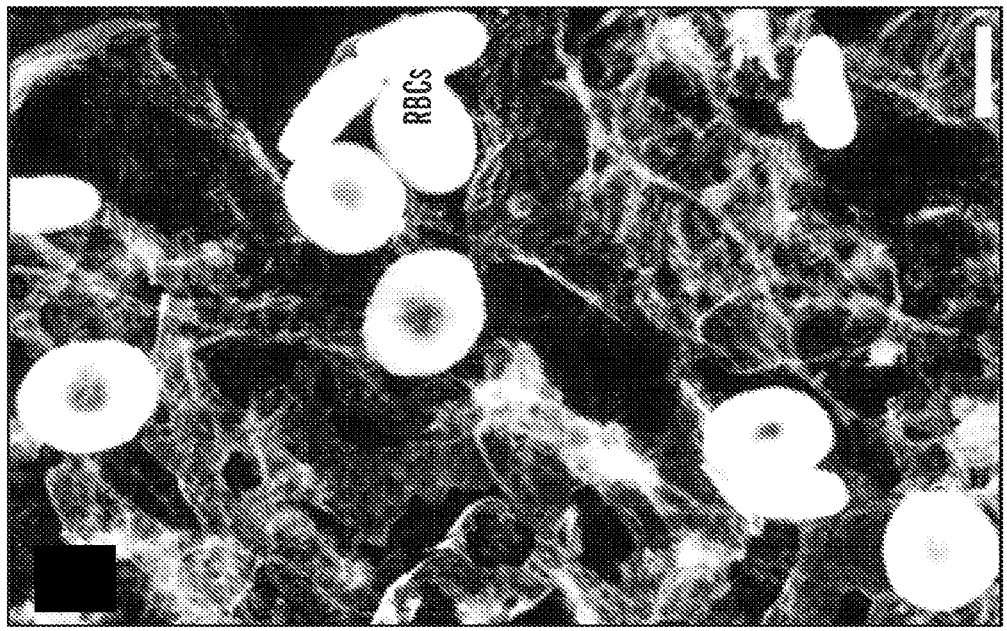
FIGS. 3A-3D show light microscopy, electron microscopy, and graphs demonstrating that NETS provide a scaffold for red blood cell (RBC)-rich thrombi.
Figure 3A:
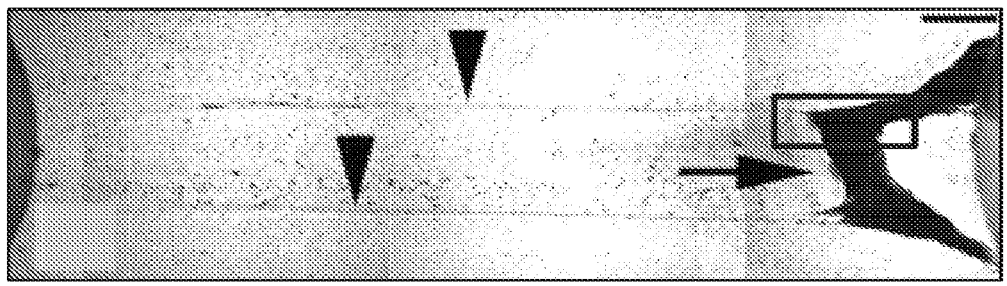
Figure 3D:
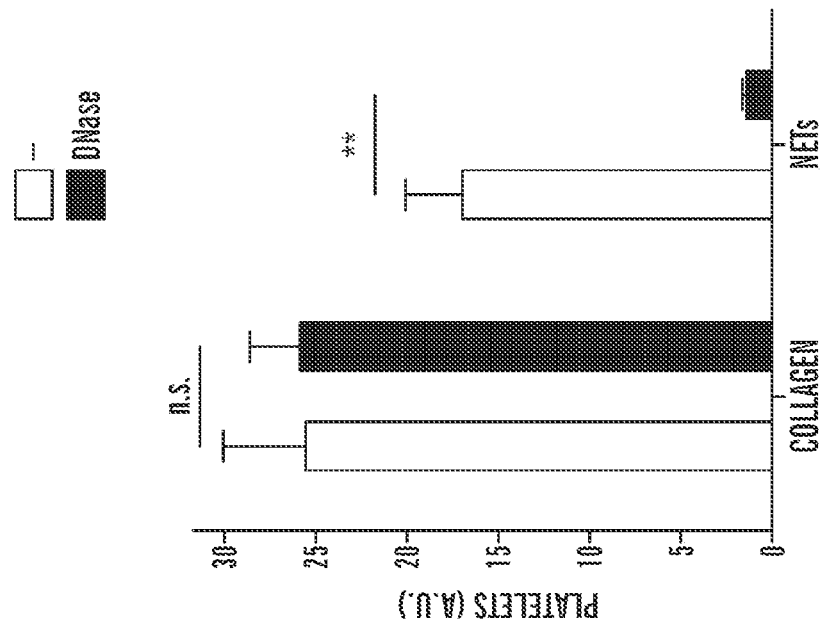
Figure 3C:
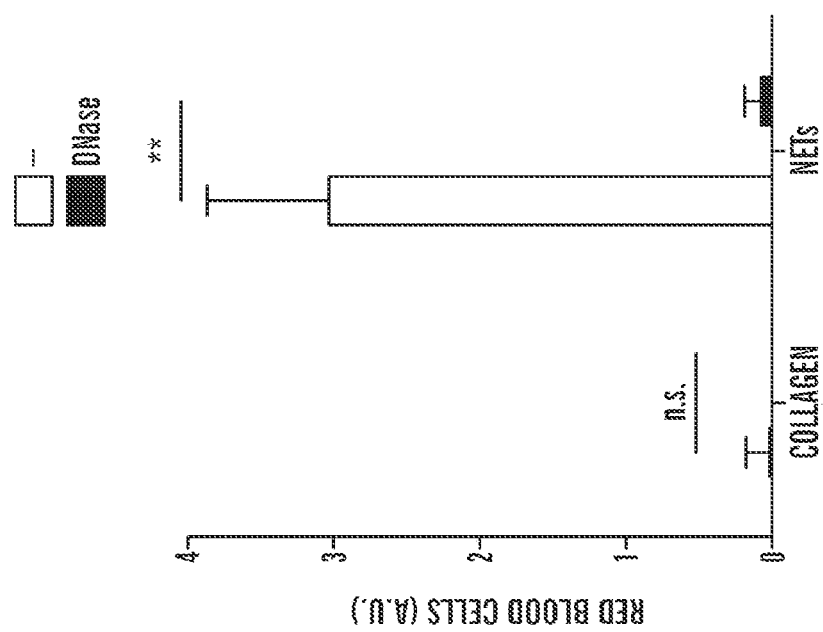

When NETs were washed after perfusion with blood and observed macroscopically a red thrombus was detectable (FIG. 3A). Shown in FIG. 3A is a flow chamber coated with NETs after perfusion with blood. Light microscopy of a red thrombus (arrow) anchored on two strings (arrowheads). FIG. 3A is a composite of multiple photographs of the flow chamber. (Scale bar, 500 µm). DNA staining revealed a scaffold of DNA and electron microscopy showed the presence of intact RBCs (FIG. 3B; scale bar, 5 µm). Quantification of RBC hemoglobin in flow chambers coated with NETs or collagen and perfused with blood showed that RBCs bound to NETs but not collagen (FIG. 3C), although platelets bound to both substrates (FIG. 3D). RBC adhesion to NETs was prevented when blood was supplemented with DNase, confirming that RBCs were attached to NETs. DNase had no effect on platelet adhesion to collagen-coated chambers, but prevented platelet adhesion to NETs (FIG. 3D). In summary, these data show that NETs provide a scaffold not only for platelets but also for RBC adhesion. Data presented are representative of at least three independent experiments and presented as mean±SEM, n=3; (ANOVA; **P<0.01); n.s.=not significant.

Figure 19A:
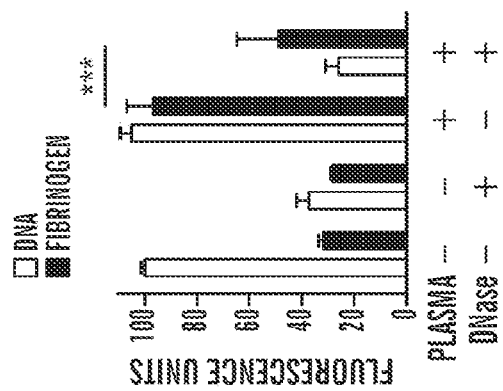
FIGS. 19A-19C depict graphs of the binding of von Willebrand factor (VWF), fibronectin, and fibrinogen to neutrophil extracellular traps (NETs). Human NETs were incubated with human plasma for 30 min, washed, and stained for VWF (19A), fibronectin (19B), or fibrinogen (19C). Quantification showed that all three proteins were binding to NETs in a DNase-sensitive manner. Data are presented as mean±SEM, n=3; (Student's t test); P<0.01; *P<0.001.
Figure 19B:
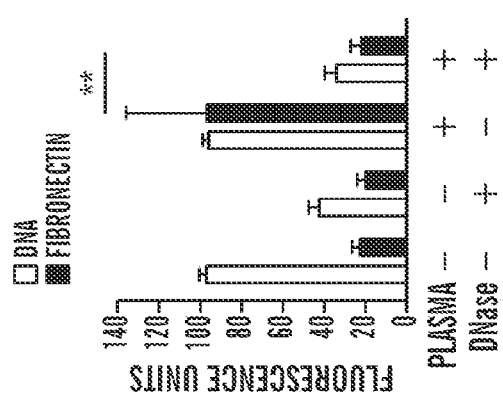
Figure 19C:
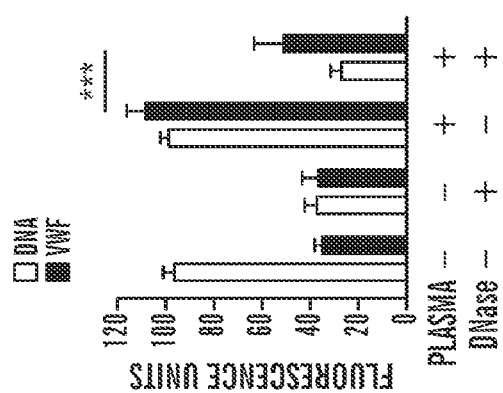

Whether NETs can concentrate plasma proteins that promote and stabilize thrombi (Frenette and Wagener NEJM 1996 335:43-5) was determined. Immunocytochemistry of NETs incubated with plasma showed that VWF and fibronectin, as well as fibrinogen, bound to NETs (FIGS. 19A-19C). After the activation, NETs were incubated with 1% BSA for 1 h at 37° C. NETs were washed and incubated with 50% plasma in PBS for 30 min at 37° C. Next, NETs were washed and treated with DNaseI (100 U/mL, 10 min). After another wash, cells were fixed with paraformaldehyde (2%, 1 h at 37° C.) and unspecific binding sites were blocked with BSA (3%, 1 h at 37° C.). Primary antibodies were used at 1 µg/mL in PBS supplemented with 1% BSA and 0.1% Triton ×100 [mouse-antifibrinogen, rabbit-antifibronectin (both Sigma); rabbit-anti-VWF, (Chemicon)]. After incubation at 37° C. for 1 h, samples were washed with PBS and fluorescently conjugated secondary antibodies (Invitrogen) were applied at 10 µg/mL for 30 min at 37° C. These findings are corroborated by previous reports that VWF and fibrinogen interact with histones (Ward et al. Thromb Res 1997 86:469-77; Gonias et al., Thromb Res 1985 39:97-116) and that fibronectin bears a DNA-binding domain (Pande et al., J Biol Chem 1985 260:2301-6). The interaction of fibrinogen with NETs and its ability to promote fibrin deposition was determined. NETs were perfused with recalcified blood supplemented with fluorescent fibrinogen (100 µg/mL; Invitrogen) and 20 mM $CaCl_2$ at the beginning of the perfusions. Fibrinogen was detected along NET-DNA strings and the deposition drastically increased with perfusion time until the large fluorescent clot "embolized" together with the NETs. Thrombin was inhibited in parallel samples to prevent fibrinogen conversion to fibrin and polymerization. Under these conditions, just traces of fibrinogen were found on NETs and NETs remained stable during the entire perfusion period. Taken together, these experiments show that NETs support platelet-adhesion molecule deposition and thrombin-dependent fibrin formation.

Figure 20:
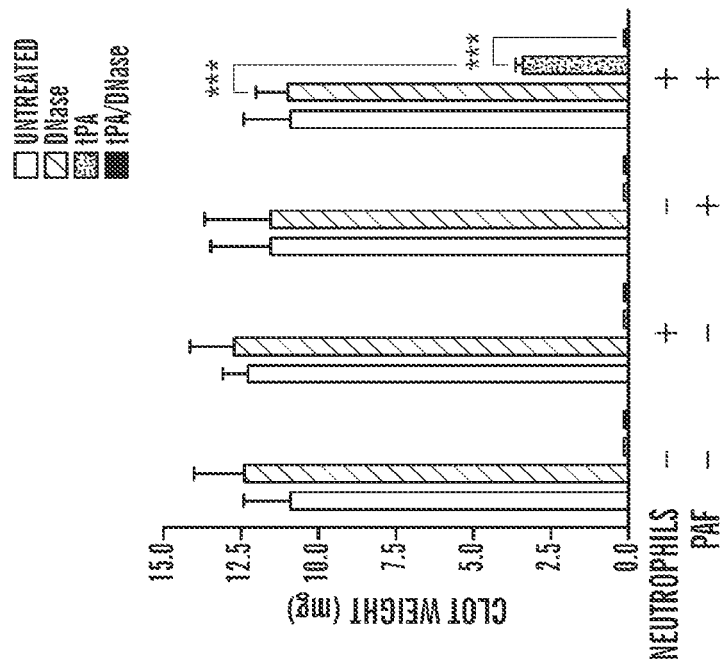
FIG. 20 depicts a graph demonstrating that NETs intercalate within a fibrin clot and generate a tissue plasminogen activator- (tPA) resistant scaffold. Fibrin polymerization was induced in blood by recalcification and incubated either in the absence (medium) or presence of neutrophils preactivated by PAF to induce NET formation (neutrophils+PAF). Samples were treated with DNase to digest extracellular traps or tPA for fibrin digestion. In the absence of activated neutrophils, clots were rich in RBCs, coincubation with DNase had no effect, and tPA alone, or together with DNase prevented clot formation. In the presence of activated neutrophils, blood clot appearance and size did not change even in the presence of DNase. The tPA reduced clot size and prevented clot formation only in combination with DNase. (Scale bar, 1 cm.) The graph presents quantification of the clots by weighing. The presence of PAF or unstimulated neutrophils alone did not produce a tPA-resistant clot. Data are presented as mean±SEM, n=4; (ANOVA; ***P<0.001). The first bar in each x-axis category represents the untreated samples, the second bar represents the samples treated with DNase, the third bar represents the samples treated with tPA, and the fourth bar represents the samples treated with tPA and DNase.

The relative susceptibility of NETs and fibrin to serve as scaffolds for blood clots to thrombolysis was examined (FIG. 20). Neutrophils were prestimulated with platelet-activating factor to release NETs with recalcified blood under stirring conditions. Two-hundred-fifty microliters of $5\times10^6$ neutrophils per milliliter in RPMI medium were activated by platelet activating factor (50 µM, Calbiochem) at 37° C. under static conditions to induce NET formation. Control samples were 250 µL medium alone, 250 µL of unstimulated neutrophils, or 250 µL of 50 µM PAF in medium. After 10 min, 250 µL of recalcified (40 mM $CaCl_2$) ACD anticoagulated blood was added. The mixture was incubated under stirring conditions (1,000 rpm) at 37° C. using an Eppendorf Thermomixer. Indicated samples were supplemented with tPA (25 µg/mL, Baxter) or DNase 1 (100 U/mL, Worthington Biochem). After 20 min, the blood was passed through a 100-µm cell strainer to isolate the clot. Images were acquired and the clot was determined. Thereafter, 10-µm frozen sections of the clot were prepared and stained for fibrinogen (mouse-antihuman-fibrinogen, Sigma) and VWF (rabbit-antihuman-VWF, Chemicon). Isotype control antibodies were used to determine background staining and DNA was labeled fluorescently by Hoechst 33258 (Invitrogen).

A single clot in which DNA intercalated with fibrin formed under these conditions. Samples were treated with DNase to digest NETs or tissue plasminogen activator (tPA) for fibrin digestion. The tPA removed fibrin but did not prevent clot formation. In tPA-resistant clots, RBCs and platelets were held together by a DNA scaffold of NETs. Consequently, clot formation in the presence of activated neutrophils could be prevented only by simultaneous treatment with tPA and DNase. Thus, NETs may provide a clot scaffold independent from fibrin.

Red thrombi, as well as leukocyte recruitment, are characteristics of DVT (Esmon Blood Rev 2009 23:225-9). Thus, whether NETs are formed in experimental DVT in baboons was determined. In brief, anesthetized juvenile male baboons underwent iliac vein thrombosis by temporary balloon catheter occlusion (6 h). Six days postthrombosis, the animal was humanely killed and both the thrombosed and nonthrombosed iliac veins were harvested. The iliac vein samples were then fixed and paraffin-embedded for immunohistochemical analysis.

Plasma was collected before and during DVT and analyzed for circulating DNA (FIG. 4; BL=baseline), a marker of intravascular NET formation in sepsis (Margraf et al., Shock 2008 30:352-8). Blood was drawn from the left iliac vein using a 22-G vacutainer needle with a 4.5-mL sodium citrate vacutainer. After centrifugation at 3,350×g for 15 min at room temperature, aliquots were flash-frozen in liquid nitrogen and stored in −80° C. Time-points included: before (baseline), 6 h, 2 d, and 6 d postthrombus induction. Plasma was diluted 10-fold in PBS and mixed diluted plasma with an equal volume of 1 µM of the fluorescent DNA dye SytoxGreen (Invitrogen) in PBS. Fluorescence was determined by a fluorescence microplate reader (Fluoroskan, Thermo Scientific). Samples were normalized to the mean of values obtained from plasma collected before induction of DVT (baseline).

Plasma DNA levels were low before and after the 6 h-DVT induction; thus, the surgical procedure did not increase this marker. Elevated plasma DNA levels were detected 2 d after thrombus induction and remained increased at 6 d postinduction (FIG. 4; bar represents the mean value of the groups; Repeated measures ANOVA; **$P<0.01$ compared with BL). It is interesting that the kinetics of the appearance of the fibrin degradation product D-dimer in plasma of baboons subjected to the same model is very similar (Meier et al., Thromb Haemost 2008 99:343-51).

Baboon DVT was also analyzed using a blood vessel staining kit (Millipore) with a different set of antibodies. The following primary antibodies were used: mouse-antihistone H2A/H2B/DNA complex (42), rabbit-anti-VWF (Chemicon), and rabbit-antihistone H3 (Abcam). Primary and isotype control antibodies were employed at 1 µg/mL; fluorescently conjugated secondary antibodies (Invitrogen) at 10 µg/mL DNA was labeled with Hoechst 33342 (1 µg/mL, Invitrogen), or SytoxGreen (1 µM, Invitrogen).

DNA staining of the thrombosed iliac vein showed the circular vessel wall and within the lumen a dispersed punctuate staining, indicating nuclei from leukocytes as well as a dense DNA core. This image comprised two distinct DNA patterns: the dotted staining of nuclei and a diffuse staining of extracellular DNA, reminiscent of NETs. Positive staining using an antibody specific for DNA/histone complex showed that the DNA was of nuclear rather than mitochondrial origin. Immunolocalization of VWF revealed abundant VWF strings within the DNA core and in the area between the DNA core and the vessel wall. The DNA pattern often overlapped with that of VWF. As a control, the right iliac vein from the same baboon was analyzed. No indications of NETs were observed in this tissue. Areas within the thrombus lacking visible extracellular DNA were abundant in histones, indicating the degradation of extracellular DNA presumably by nucleases in plasma. In summary, markers of NETs are present in plasma and within the thrombus of baboons subjected to DVT.

NETs are a unique link between inflammation and thrombosis which provide a stimulus and scaffold for thrombus formation and markers of NETs are abundant in DVT. Inhibition of leukocyte infiltration in the baboon model of DVT produces unstable thrombi (Meier et al., Thromb Haemost 2008 99:343-51). One way leukocytes can promote thrombus stability is by producing NETs. The results described herein show that NETs colocalize with fibrin in vitro.

Ischemia results in the production of IL-8 and reactive oxygen species. IL-8 is capable of inducing NETs (Brinkmann et al., Science 2004 303:1532-5) and is considered a risk factor for venous thrombosis. In vitro stimulation of neutrophils with exogenous reactive oxygen species is sufficient to induce NETs (Fuchs et al., J Cell Biol 2007 176:231-41). Mechanistically, NETs provide a scaffold for platelet and RBC adhesion and concentrate effector proteins involved in thrombosis.

DNA has been detected on the cell surface of platelets from patients with systemic lupus erythematosus (Frampton et al., Clin Exp Immunol 1986 63:621-8). Lupus patients are prone to develop venous thrombosis (Esmon Blood Rev 2009 23:225-9) and were recently described to have impaired NET degradation (Hakkim et al. PNAS 2010 107:9813-8). RBC adhesion to NETs could also play a role in sickle-cell disease, where a lethal crisis is often precipitated by infection (Booth et al., Int J Infect Dis 2010 14:e2-e12).

Statistical analysis included mean±SEM, ANOVA, Student's t test, and repeated measures ANOVA. Results were considered significant at $P<0.05$.

Example 2

NETs in Blood Storage Products

In order to determine if some of the toxicity associated with non-leukocyte depleted blood products was due to the accumulate of NETs during blood storage, the levels of NETs in blood bank samples were determined. Plasma DNA concentrations of two blood bags, one with leukocytes and one depleted of leukocytes (leuko-reduced) were determined. Blood was stored in the blood bank at Brigham and Women's Hospital & Dana Faber Cancer Institute, Boston for more than 42 days in blood transfusion bags. Plasma was separated from blood cells by two centrifugations. Blood was centrifuged at 3000 g for 10 min. The platelet poor plasma was collected and spun again at 10000 g for 5 min. Aliquots of double-centrifuged plasma were stored at −80° C. Plasma was then diluted 1:10 in phosphate buffered saline (PBS). Fifty µl of diluted plasma was mixed with 50 µl of PBS containing 2 µM SytoxGreen (Invitrogen) to label DNA and fluorescence was recorded in a fluorometer (Fluoroskan, Thermo Fisher Scientific). Auto-fluorescence was considered as background and determined in samples mixed with PBS without SytoxGreen. Plasma from non-leukoreduced blood had high levels of plasma DNA (4255 ng/ml) compared to plasma from leuko-reduced blood (138 ng/ml). These results indicated that leukocytes release DNA into plasma during blood storage.

During a second round of experimentation, the blood bank provided additional blood bags. Quantification of plasma DNA showed that the average DNA levels in 10 non-leukoreduced blood (Non-R in FIGS. 5A-5B) were approximately 100-fold higher that in plasma of fresh blood taken from 10 healthy donors (control) (FIG. 5A). Low levels of DNA were detected in plasma from 14 bags depleted of leukocytes (Leuko-R in FIG. 5A). These experiments suggest that leukocytes commonly release high levels of NETs during blood storage.

The release of NETs in stored blood was examined by detecting histones. An ELISA assay (Cell death detection kit; Roche) was used in which two antibodies are employed; one which will recognize histones H2A, H2B, H3, and H4 (all of which are present in NETs) and a second antibody specific for double-stranded DNA. One unit of nucleosomes was defined as the average amount of nucleosomes quantified in plasma from fresh blood controls. Again, stored plasma from blood bags containing leukocytes (Non-R) showed higher levels of NETs that fresh blood (control) or stored leukocyte-depleted plasma (Leuko-R) (FIG. 5B). This confirmed the conclusion that leukocytes release NETs during storage of blood products.

In order to rule out the possibility that apoptotic cells were releasing DNA, total plasma DNA from three samples of non-leukocyte depleted blood was subjected to gel electrophoresis. DNA was isolated from plasma using a DNA isolation kit according to manufacturer's instructions (Omega bio-tek, Norcross, Ga.), subjected to 2% agarose gel electrophoresis in the presence of ethidium bromide and visualized using a gel documentation system (BioRad, Hercules, Calif.). Apoptotic DNA is highly degraded, whereas the DNA associated with NETs is not degraded. Electrophoresis of the plasma DNA revelaed undegraded, high-molecular weight DNA, confirming that earlier assays were detecting NETs and not apoptotic DNA.

In order to determine if an anti-NET compound could be used to treat stored blood products, the effects of DNaseII on NET release during blood storage was tested. Blood collected from healthy donors was stored for up to three days and mixed with Citrate-Phosphate-Dextrose (CPD) to prevent coagulation. Blood was stored at room temperature on a rotary mixer. During storage NET release into plasma was quantified by the ELISA (FIG. 6). If blood was supplemented with 10 U/mL DNaseII (Worthington Biochem), no NETs were detected in plasma. These results indicated that NETs can be degraded by an anti-NET compound during blood storage. It is noteworthy that blood is stored in the absence of divalent cations and at acidic pH. Most nucleases require calcium and magnesium ions to degrade DNA and would therefore not function in stored blood. DNaseII cleaves DNA without divalent cations and functions optimally at low pH.

In all cases statistical analysis included mean±SEM, analysis of variance (ANOVA). Results were considered significant at $P<0.05$.

Example 3

Anti-NET Compounds in the Treatment of Stroke

Data are expressed as mean plus or minus SEM. All statistical analysis was performed using Prism 4 (version 4.0b, Graphpad Software, Inc., La Jolla, Calif.). Infarct volumes and neurologic scores were analyzed using the unpaired 2-tailed Student t test. P values less than 0.05 were considered statistically significant.

In order to determine if NETs were released during cardiovascular stress, the level of NETs was determined in plasma samples of wild-type C57BL/6 mice kept under normoxic (room air) and hypoxic (hypoxia chamber with 6% 02) conditions for 24 hours. Wild type C57Bl/6 mice were purchased form Jackson Laboratory (Bar Harbor, Me.). All animals used in this work were 8-10 weeks old males (except for hypoxia experiments in which females were used). Animals were provided with free access to standard laboratory chow and water and were kept on a light/dark cycle of 12 h. Mice were exposed to normobaric hypoxia at 6% oxygen for 24 hours or were housed at normal air room pressure. For hypoxia treatment, animals were placed in a controlled atmosphere animal chamber (A-15274-P, Biospherix, Lacona, N.Y.). Hypoxia was achieved by substituting nitrogen for oxygen using a Pro:ox model 110 compact oxygen controller (Biospherix, Lacona, N.Y.). Hypoxic animals had significantly increased nucleosome levels that were approximately 5 times higher than nomioxic mice.

Next, the question of whether cerebral ischemia/reperfusion injury effects circulating levels of NETs was addressed. Wild-type C57BL/6 mice were subjected to 2 hours of transient middle cerebral artery occlusion (tMCAO), followed by 22 hours of reperfusion. Focal cerebral ischemia was induced by 60 or 120 min tMCAO. Mice were anesthetized with 2% isoflurane/oxygen mixture. Following a midline skin incision in the neck, the proximal common carotid artery, and the external carotid artery were ligated, and a standardized silicon rubber-coated 6.0 nylon monofilament (6021; Doccol Corp., Redlands, Calif.) was inserted and advanced via the right internal carotid artery to occlude the origin of the right MCA. Operation time per animal did not exceed 15 minutes. The intraluminal suture was left in situ during the complete occlusion time. Then animals were re-anesthetized, and the occluding monofilament was withdrawn to allow reperfusion. In animals undergoing a sham treatment, the exact same procedure was followed except that the monofilament was only inserted three quarters of the normal distance that is necessary to occlude the MCA, after which it was immediately withdrawn. Some animals were exclusively used for laser-Doppler flowmetry (Periflux 5000, Perimed, Kings Park, N.Y.) to monitor regional cerebral blood flow (rCBF) in the MCA territory.

Before the surgical procedure and after reperfusion, blood samples were collected and plasma was prepared. Sham-operated animals underwent the same surgery but without occlusion of the right MCA. Levels of circulating DNA and nucleosomes were determined in the plasma samples (FIGS.

7A-7D). To measure nucleosome and DNA levels in plasma, blood was collected from the retro-orbital sinus using 0.5M EDTA as anticoagulant. Plasma was prepared by centrifuging anticoagulated whole blood for 5 min at 2300×g. Plasma supernatant was carefully removed and centrifuged again for 5 min at 2300×g to remove any contamination with blood cells. The plasma was stored at −80° C. until analysis. Nucleosome levels were measured using the Cell Death Detection ELISA$^{PLUS}$ (Roche, Indianapolis, Ind.). Plasma was diluted 1:10 (V:V) in phosphate buffered saline. Fifty µl of diluted plasma was mixed with 50 µl of PBS containing SytoxGreen (final concentration 2 µM, Invitrogen) to label DNA and fluorescence was recorded in a fluorometer (Fluoroskan, Thermo Fisher Scientific). Auto-fluorescence was considered as background and determined in samples mixed with phosphate buffered saline without SytoxGreen. FIGS. 7A and 7B show the levels of extraceullular nucleosomes in, respectively, sham and stroke-induced animals. FIGS. 7C and 7D show the levels of extracellular DNA in, respectively, sham and stroke-induced animals. The sham procedure increased both nucleosome and DNA levels. This 3.07±0.79 and 1.32±0,.16 fold over baseline levels respectively most likely reflects cell death caused by the invasive surgery. However, in animals that experienced stroke, levels of circulating nucleosomes and DNA were significantly more increased to 7.65±1.85 and 4.88±1.68 times baseline levels respectively ($p<0.05$). These results show that cerebral ischemia/reperfusion injury results in the generation of NETs.

As shown herein, the ability of DNase-1 to cleave DNA/platelet strings limits the extent of extracellular DNA trap-mediated platelet adhesion and aggregation. It was therefore hypothesized that this enzyme may prevent excessive platelet adhesion and aggregation induced by extracellular chromatin generated by ischemic stroke. To test the role of DNase-1 in stroke, DNase-1$^{-/-}$ mice were used in the tMCAO model. DNase1$^{-/-}$ mice were generated in a mixed 129×C57BL/6 genetic background and back-crossed into the pure C57BL/6 genetic background for ten generations. The gene knockout was performed by classical genetic methods including the physical mapping of the gene locus by restriction site analysis, identification of the gene locus at chromosome 16 by FISH-analysis and isolation of a HindIII genomic DNA-fragment from a bacteriophage library. At the time when the DNase1 knockout was generated and published no other gene was described to be located in the vicinity of the DNase1 gene locus. However, due to the sequencing of the murine genome it became clear recently that the deletion of the DNase1 gene affects another gene located partly in the 3'-untranslated (3'-UTR) and -flanking region (3'-FR) of the DNase1 gene. The original gene knockout scheme was amended by the location of exons 13 to 18 of the Trap1/Hsp75 (TNF type I receptor-associated protein 1/heat shock protein 75) gene, whose reading-frame is located on the opposite DNA-strand than that of the DNaseI gene. Due to the deletion of a 2886 Bp long EcoRI/SmaI genomic DNA-fragment of the DNaseI gene locus parts of the coding region and the complete 3'-UTR of exon 18 of the Trap1 gene were deleted in addition.

Figure 8A:
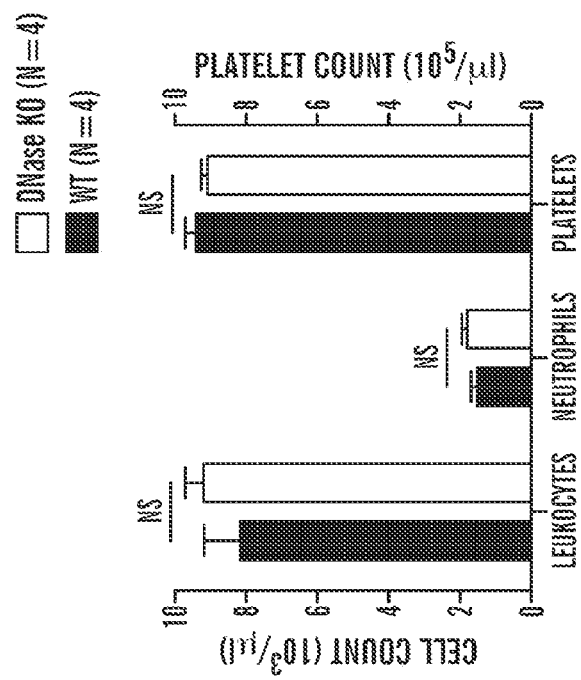
FIGS. 8A-8C show graphs depicting the cerebral structure and blood counts of DNase-1$^{-/-}$ mice.
Figure 8B:
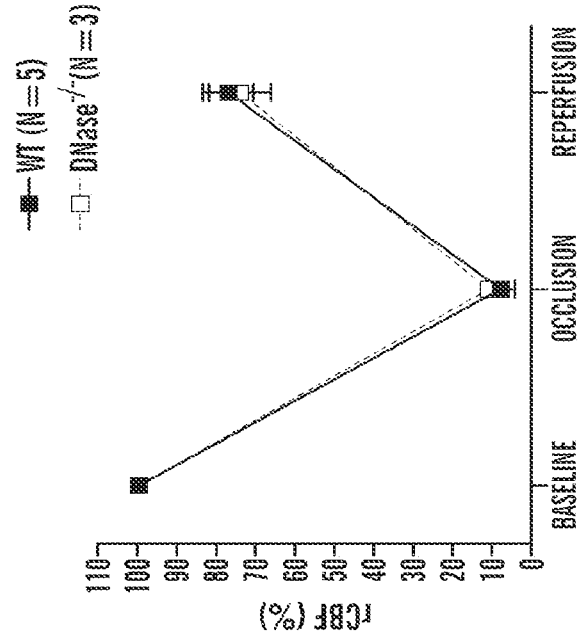
Figure 8C:
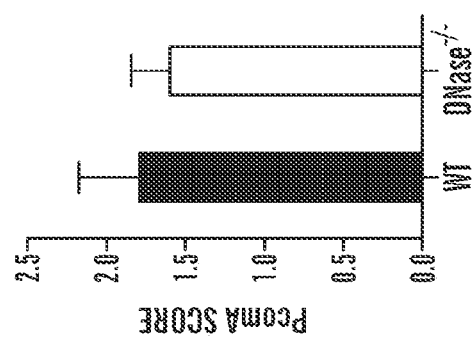

The cerebral vasculature of WT and DNase-1$^{-/-}$ mice showed no major anatomic differences that could influence stroke outcome (FIG. 8A, 8B). For assessment of the cerebral vasculature, animals were deeply anesthetized with isoflurane and transcardially perfused with phosphate buffered saline, followed by 5 ml black ink. Brains were carefully removed, fixed in 4% PFA and the Circle of Willis and major arteries were examined under a dissecting microscope. The development of the posterior communicating arteries (PComAs) was examined and scored as described (Murakami et al. Stroke 1997 28: 1797-1804). The circle of Willis and the distribution of the MCA trunk and branch appeared to be anatomically identical between the genotypes. In addition, the score assessing formation of the posterior communicating arteries of both hemispheres, which can influence susceptibility to tMCAO, did not differ significantly in WT and DNase-1$^{-/-}$ mice (1.80±0.37 versus 1.60±0.24 respectively, $p>0.05$, FIG. 8A). No differences were found in the regional cerebral blood flow (rCBF) in the right MCA territory (FIG. 8B). WT and DNase-1$^{-/-}$ mice showed a comparable decrease in rCBF during tMCAO (7.71±3.74% of baseline versus 10.27±0.65% of baseline respectively, $p>0.05$) and a comparable degree of reperfusion (76.82±6.51 of baseline versus 74.04±7.69% of baseline respectively, $p>0.05$). No differences in cell blood counts could be detected between the two genotypes (FIG. 8C).

Figures 9A, 9B:
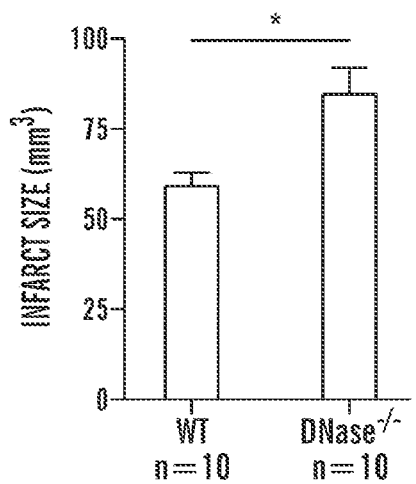
FIGS. 9A-9B show graphs and scores indicating that DNase-1$^{-/-}$ mice are more prone to ischemic stroke.

Interestingly, DNase-1$^{-/-}$ mice were more prone to ischemic stroke (FIGS. 9A-9B). Wild type (WT) and DNase-1$^{-/-}$ mice were subjected to 1 h of tMCAO and 23 h of reperfusion after which mice and brains were analyzed. Mice were killed 24 hours after initiation of tMCAO. Brains were quickly removed and cut into 2-mm-thick coronal sections using a mouse brain slice matrix. The slices were stained with 2% 2,3,5-triphenyl-tetrazolium chloride (TTC; Sigma-Aldrich, St. Louis, Mo.) in PBS to visualize the infarctions. Sections were photographed with a digital Nikon D70 camera and infarct areas (white) were measured blindly using Image J software (National Institutes of Health). Brain infarct volumes were measured by planimetry (FIG. 9A). Compared to the wild-type controls, DNase-1$^{-/-}$ mice developed larger brain infarctions (84.10±7.24 mm$^3$ versus 58.50±4.04 mm$^3$, $p<0.05$, FIG. 9A).

This difference in infarct size was functionally relevant as both the Bederson score and the grip test (FIG. 9B) score were significantly worse in DNase-1$^{-/-}$ mice (*$P<0.05$). Neurological function was assessed, blinded for the mouse genotype 24 h, after initiation of tMCAO, using the modified Bederson score (Bederson et al., Stroke 1986 17:472-6). This test determines global neurological function according to the following scoring system: 0, no deficit; 1, forelimb flexion; 2, decreased resistance to lateral push; 3, unidirectional circling; 4, longitudinal spinning; 5, no movement. The grip test was performed as described (Moran et al., PNAS 1995 92:5341-5). A mouse was placed on a wooden bar (3 mm in diameter, 40 cm long) that is attached to two vertical supports 40 cm above a flat surface. When placing the mouse at a point midway between the supports, the experiment was rated according to the following system: 0, falls off; 1, hangs onto bar by two forepaws; 2, as for 1, but attempts to climb onto bar; 3, hangs onto bar by two forepaws plus one or both hindpaws; 4, hangs onto bar by all four paws plus tail wrapped around bar; 5, escape (where mouse was able to work its way to one of the supports). To assess behavior in the corner test (Zhang et al., J Neurosci Methods 2002 117:207-214), a mouse was placed on a flat surface between two vertical boards that are arranged in an angle of 30° with a small opening along the joint between the two boards to encourage entry into the corner. The mouse was placed between the two angled boards facing the corner and half way to the corner. When entering deep into the corner, the mouse rears forward and upward, then turns back to face the open end. The non-ischemic mouse turns either left or right, but the ischemic mouse preferentially turns toward the non-impaired, ipsilateral (right) side. The turns in one versus the other direction were recorded from ten trials for each test. Turning movements that were not part of a rearing movement were not scored. Mice that were not able to walk (Bederson score 4 or 5) were excluded. These data indicate that DNase-1 can have a protective effect in ischemic stroke. Since DNase-1 deficiency is accompanied in this strain by a reduced expression of TRAP-1, it was decided to corroborate the results by infusion of recombinant human DNase-1 (rhDNase-1) in wild-type mice.

Figures 10A, 10B:
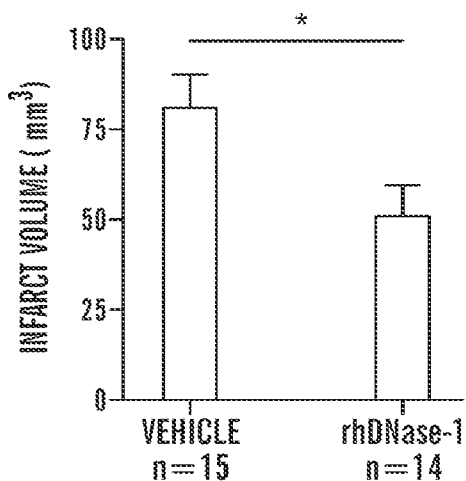
FIGS. 10A-10B show graphs and scores indicating that infusion of rhDNase-1 protects mice from ischemic stroke.

To further investigate the possible protective role of DNase-1 in ischemic stroke, WT animals were treated with recombinant human DNase-1 (rhDNase-1)(Dornase alpha, Pulmozyme®, Genentech Inc. San Francisco, Calif.) during a 1 h tMCAO and 23 h of reperfusion. Fifteen minutes before surgery, 50 µg of rhDNase-1 was given intra-peritoneally and this was repeated 12 h later. In addition, five minutes before reperfusion, 10 µg of rhDNase-1 was given via retro-orbital intravenous injection. infarct size and volume was determined as described herein. Compared to vehicle-treated animals, mice receiving rhDNase-1 developed approximately 40% smaller infarcts ($81.45 \pm 9.08$ mm$^3$ versus $50.67 \pm 8.74$ mm$^3$, $p<0.05$, FIG. 10A). Treatment of mice with rhDNase-1 also led to dramatic improvement in functional outcome as shown by tests assessing neurologic and motoric behavior. Compared to vehicle-treated mice, the Bederson test score, the grip test score and the corner test result were all significantly better in rhDNase-1 treated mice ($p<0.05$, FIG. 10B).

Figure 11:
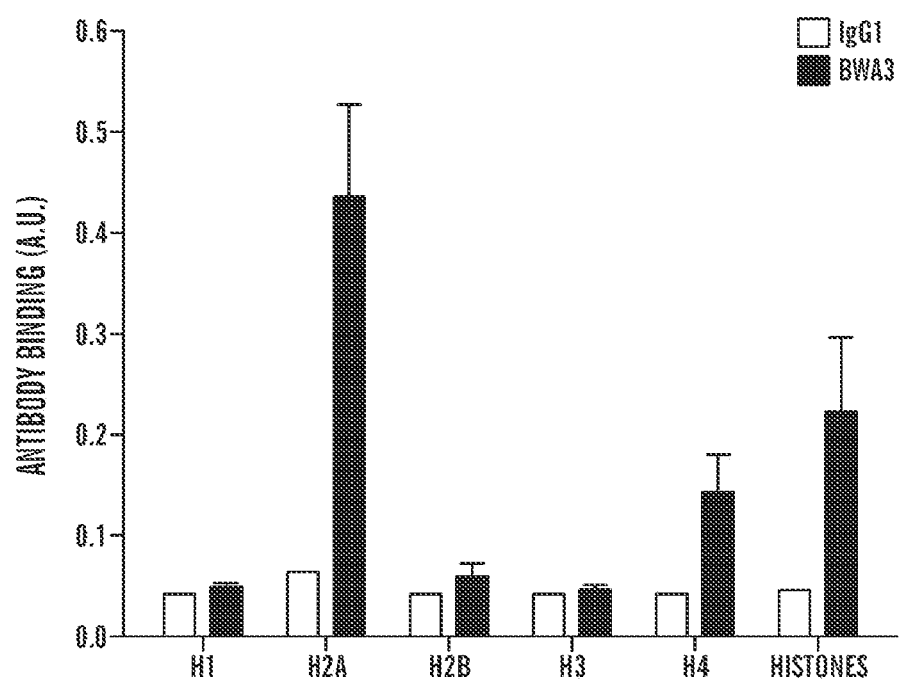
FIG. 11 shows the characterization of the BWA3 antibody's binding to different histones. The x-axis lists different histones or a mixed population of histones (histones). The y-axis listing the degree of antibody binding in arbitrary units (A.U.). BWA3 binding is shown in black bars while the control IgG1 binding is shown in white bars.
Figures 12A, 12B:
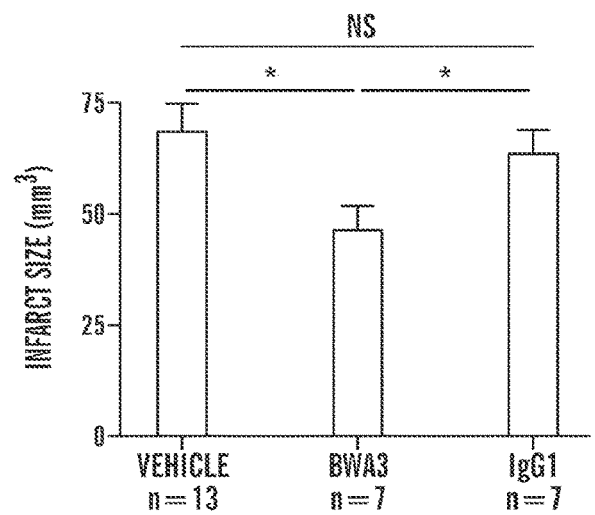
FIGS. 12A-12B show graphs and scores indicating that histone neutralization is protective during ischemic stroke.

Nucleosomes, key constituents of NETs, are basically segments of DNA wrapped around a histone protein core. Extracellular histones have been shown to be cytotoxic toward. endothelium, to be able to induce intravascular thrombosis and even to cause death when administered in sufficient amount to mice. To assess whether extracellular histories are also of pathological significance in the progression of ischemic stroke, histone-neutralizing antibody (BWA3, 10 mg/kg) was infused 5 min before reperfusion (FIGS. 12A-B). Antibodies against histone H4 were isolated from cell culture supernatants of hybridoma clone BWA3 by affinity chromatography on protein G columns. Purified antibodies were dialyzed against saline and were characterized by testing for binding to purified histones H1, H2A, H2B, H3, H4 and a mixture of all histones in an ELISA set-up. BWA3 antibodies bound to H2A and H4 and consequently also to the histone mix. IgG1 did not bind to histones (FIG. 11). Administration of the histone-neutralizing antibody resulted in a protective effect: when compared to animals treated with either vehicle or IgG1 isotype control antibody, infarct volumes of BWA3 treated mice were significantly smaller ($46.00 \pm 5.82$ mm$^3$ versus $68.15 \pm 6.58$ mm$^3$ (vehicle, $p<0.05$) or $63.43 \pm 4.29$ mm$^3$ (isotype control, $p<0.05$, FIG. 12A). Treatment with histone-neutralizing antibody (BWA3) consisted of a single intravenous retroorbtial bolus injection of antibody (BWA3 or IgG1 isotype control antibody) at a concentration of 10 mg/kg five minutes before reperfusion. Neurologic/motoric outcome as measured by the Bederson and grip test score (FIG. 12B) was better in BWA3-treated mice, reaching statistical significance for the grip test score (compared to vehicle-treated animals). The protective effect of this histone-neutralizing antibody indicates that histones (H4 and H2B) are a major mediator of ischemic stroke in mice.

The data shown herein indicate that NETs are increased after ischemic stroke. DNase-1 appears to have a protective role in ischemic stroke since the absence of DNase-1 aggravates stroke outcome whereas infusion of rDNase-1 improves stroke outcome. Moreover, neutralization of histones using an anti-histone antibody also had a protective effect in this stroke model. Taken together, the data suggest an important role of NETs in the development of ischemic stroke.

Experimental ischemic stroke results in a significant increase of both DNA and nucleosome levels in the circulation. Interestingly, significantly elevated concentrations of DNA and nucleosomes have also been found in stroke patients (Geiger et al., Cerebrovascular Diseases 2006 21:32-7; Lam et al., Resuscitation 2006 68:71-8; Rainer et al., Clin Chem 2003 49:562-9; Tsai et al., Clinica chimica acta 2001 412:476-9). In these patients, DNA/nucleosome levels correlated strongly with stroke severity and were associated with morbidity, mortality and degree of disability. In one study, comparison with other biomarkers such as S100 protein, neuron-specific enolase, C-reactive protein and leukocytes, nucleosomes on day 3 after stroke were the only independent prognostic biomarker for recovery after one year (Geiger et al., Cerebrovascular Diseases 2006 21:32-7). Liberation of chromatin and its degradation products from damaged cells seems a plausible mechanism for increased DNA/nucleosome levels during and after stroke. However, with increased circulating DNA/nucleosome levels as a non-specific cell death indicator and with ischemic cell damage being considered to be a dynamic process with considerable inter-individual variation, the striking association between circulating DNA/nucleosome levels and stroke severity has always been surprising. Inflammatory responses, in particular the recruitment of neutrophils, can lead to significant chromatin release by forming NETs. Indeed, while stroke causes neutrophilia, and an increase in the number of circulating monocytes (Wang et al., J Neuroimmunol 2007 184:53-68) a recent study shows that the level of plasma DNA in patients with acute ischemic stroke correlates positively with white blood cell count (Tsai et al., Clinica chimica acta 2001 412:476-9). In addition, myeloperoxidase levels, a marker for neutrophil activation, were found to be increased after stroke (Barone et al., J Neurosci Res 1991 29:336-345; Barone et al., Molecular and chemical neuropathology 1995 24:13-30; Cojocaru et al., Romanian Journal of Internal Medicine 2010 48:101-4). It is well established that inflammatory responses and recruitment of neutrophils play an important role in the pathophysiology of ischemic stroke. Neutrophil depletion, inhibition of neutrophil adhesion and inhibition of neutrophil function are all strategies that have been shown to reduce infarct volume and improve stroke outcome. The detrimental effect of neutrophils has classically been attributed to the no-reflow phenomenon (obstruction of the microcirculation) and release of toxic agents such as oxygen free radicals and proteolytic enzymes. However, as shown herein, NETs released by neutrophils also promote thrombosis and bind red blood cells. These NETs, formed by a special cell-death program that involves internal membrane dissolution, chromatin decondensation and cytolysis (Fuchs et al., Journal of Cell Biology 2007 176:231-241), are able to adhere, activate and aggregate platelets as shown herein. Interestingly, besides neutrophils, also mast cells and eosinophils release NET-like structures in response to inflammatory stimuli and reactive oxygen species (von Kockritz-Blickwede et al., Blood 2008 111:3070-3080; Yousefi et al., Nature Medicine 2008 14:949-953).

As demonstrated herein, nucleosomes are externalized during ischemic brain injury. The data presented herein show that mice deficient for DNase-1 are more susceptible to ischemic stroke and that wild-type mice treated with rhDNase-1 are protected from stroke; suggesting a protective effect of DNase-1 in ischemic brain injury. Indeed, as shown herein, in in vitro flow chambers, DNase-1 was able to remove DNA/platelet complexes from the surface, preventing DNA-mediated platelet adhesion and aggregation.

It is shown herein that histones are a potent platelet aggregation agonist and that pharmacological targeting of histone H2A/H4 leads to a significant protective effect in ischemic stroke, suggesting that histones contribute to ischemic brain injury during stroke. Pharmacological blocking of histone mediated platelet activation/aggregation and endothelial dysfunction can thus also help to attenuate ischemic stroke progression.

In conclusion, these data indicate that NETs are an important mediator of ischemic stroke in mice and that anti-NET compounds, particularly DNase, could be useful as a therapeutic agent in stroke management. As demonstrated herein, removal of excess chromatin in brain vessels could limit obstructive events mediated by NETs and preventing local accumulation of toxic and platelet-activating histones. DNase-1 is a readily available drug that is currently used for treatment of cystic fibrosis to reduce sputum viscosity by digesting DNA released from neutrophils (Lieberman, JAMA 1968 205:312-3).

Example 4

Anti-NET Compounds in the Treatment of Deep Vein Thrombosis

The role of NETs in deep vein thrombosis (DVT) was also examined using the DVT model of flow restriction in the inferior vena cava. Mice were anesthetized by isoflurane-oxygen mixture and placed in a supine position. After laparotomy, intestines were exteriorized and warm sterile saline was applied during the whole procedure to prevent drying. After gentle separation from aorta, IVC was ligated over a 30G needle by a 7.0 polypropylene suture immediately below the renal veins (towards the tail) and then the needle was removed. The needle was placed outside the vessel so that piercing or any other injury to the IVC wall was completely avoided. This procedure allows for standardized flow restriction without endothelial injury. All visible side branches (usually 1 or 2) were also ligated. After surgery, peritoneum and skin were closed by monofilament absorbable suture and 6.0 silk, respectively. Mice were euthanized after 6 h or 48 h and thrombi developed in the IVC below the suture (towards the tail) were taken for analysis.

All mice were treated with DNaseI (Pulmozyme®) immediately after surgery and mice with 48 h IVC stenosis received 3 additional injections every 12 hours. The dose of every injection was 50 µg i.p. (50 µl of non-diluted Pulmozyme) and 10 µg i.v. (in 50 µl of sterile saline) in retro-orbital plexus. Control mice were injected with the same volume of DNase buffer (8.77 mg/ml sodium chloride and 0.15 mg/ml calcium chloride in sterile water for injections).

In the 6 h IVC stenosis model, half (7 of 14) of the vehicle-treated mice produced a thrombus whereas in mice that received DNase I, only 1 mouse of 10 formed a thrombus (P<0.05 by the chi-square test; FIG. 13C). Sixty two percent (5 of 8) of control mice produced a thrombus 48 h after flow restriction application. In contrast, only 17% (2 of 12) of DNase I-treated mice developed a thrombus (P<0.04; FIG. 13F). Weights (FIG. 13A, D) and lengths of thrombi (FIG. 13B, E) were also significantly reduced in DNase I-treated mice in both the 6 h and 48 h IVC stenosis experiments.

Example 5

Anti-NET Compounds in the Treatment of Pulmonary Embolism

To further investigate whether prophylactic treatment with an anti-NET compound could prevent cardiovascular conditions, mice were administered DNase prior to pulmonary embolisms being induced. Male C57Bl/6J mice (22-26 g body weight, 7 weeks old) were injected with DNaseI (50 mg) or II (600 U) intraperitoneally. Thirty min later, mice were put to sleep by intraperitoneal injection of avertin (2.5%). Fifty min after the initial DNase injection, mice received intravenous infusion of DNaseI (10 mg) or DNaseII (120 U) in 50 ml buffer. Control mice were injected with the buffer at the same time points.

One hour after initial DNase or buffer injection, mice received intravenous infusion of the mixture of 0.8 mg/kg collagen (Nicomed) and 60 mg/kg epinephrine (Phoenix) in 100 ml sterile PBS. Mice were monitored for 1 h. All mice had an episode of breath insufficiency which proves that the injection of collagen/epinephrine mixture was successful. Data were compared statistically using the Chi-square test.

Figure 14:
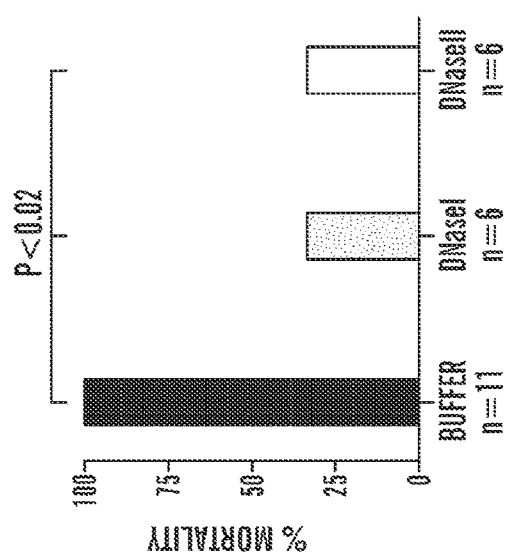
FIG. 14 shows a graph indicating that DNase protects mice from pulmonary embolism. The x-axis indicates whether mice were treated with control solutions (buffer), or administered the anti-NET compounds DNaseI or DNaseII. The number of mice in each group (n) is also specified. The y-axis shows the % morality for each group following chemical induction of pulmonary embolism.

As shown in FIG. 14, a large proportion of mice which received prophylactic doses of DNaseI or DNaseII were able to survive the injection of collagen/epinephrine while mice receiving the control injections experienced 100% mortality.

Example 6

Anti-NET Compounds in the Treatment of TRALI

In order to determine the effect of anti-NET compounds as a treatment for TRALI, a mouse model of the 2-hit TRALI model was utilized. BALB/c male mice (8-10 week-old) were primed with an intraperitoneal injection of lipopolysaccharide (LPS) (0.1 or 0.5 mg/kg) 24 hours prior to challenge with anti-H2K$^d$mAb (clone 34-1-2s1, 1 mg/kg) or isotype control injected retro-orbitally. Before each injection mice were shortly anesthetized by inhalation of isoflurane. To measure the effect of DNaseI treatment on mice experiencing TRALI, mice received intranasal DNaseI (50 µg/mouse, 1 µg/ul) or 50 µl of the buffer-vehicle 10 minutes prior to the antibody injection.

Figure 15C:
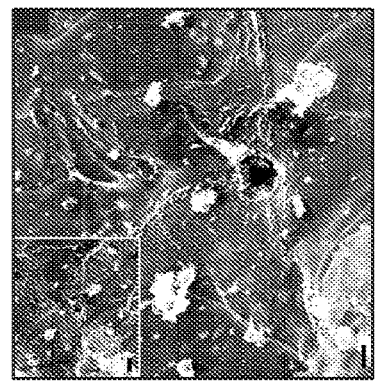
FIGS. 15A-15C show scanning electron microscopy images illustrating the effect of DNase treatments on TRALI-associated DNA-fibrous networks at the alveoli surface. Scale bar is 1 µm, insets show low magnification views where scale bar is 2 µm Alveolar sacs (a) and ducts (d) are marked.
Figure 15B:
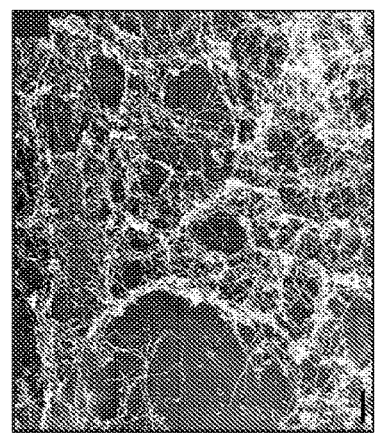
Figure 15A:
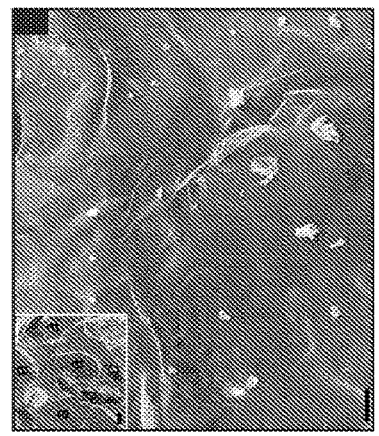
Figure 16B:
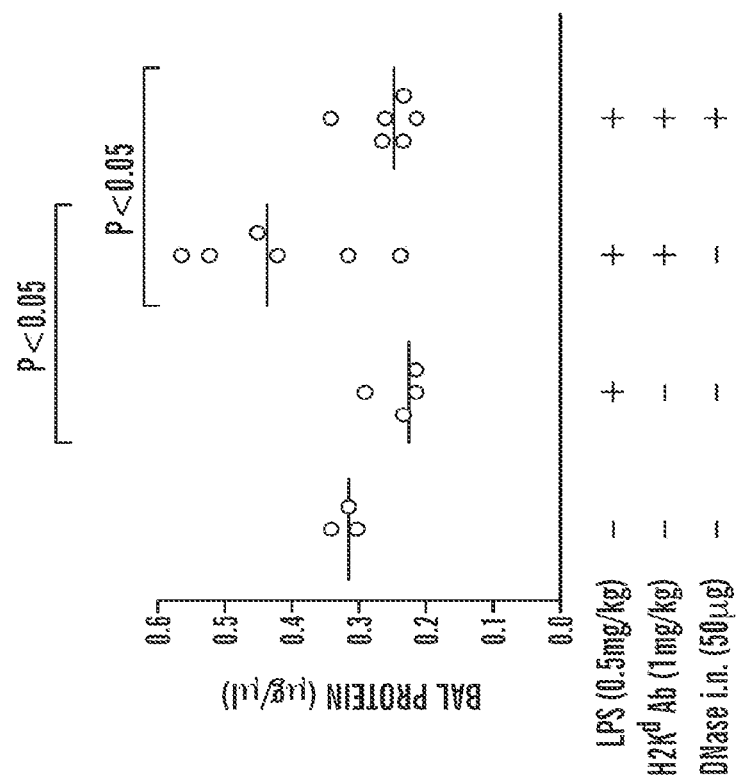
FIGS. 16A-16B show graphs indicating that DNaseI treatment is protective during TRALI. DNaseI or a vehicle control was administered intranasally 10 min prior to anti-H2K$^d$ antibody administration.
Figure 16A:
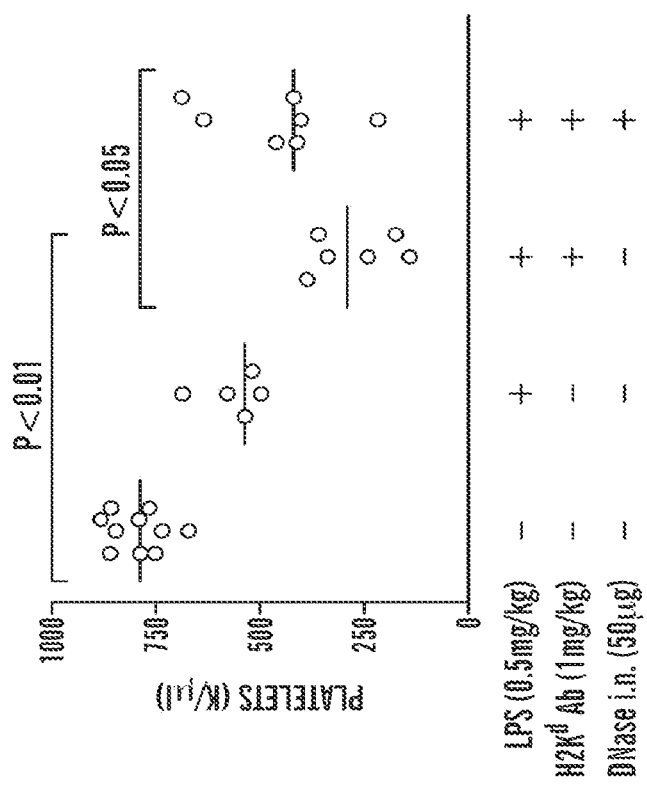
Figure 17A:
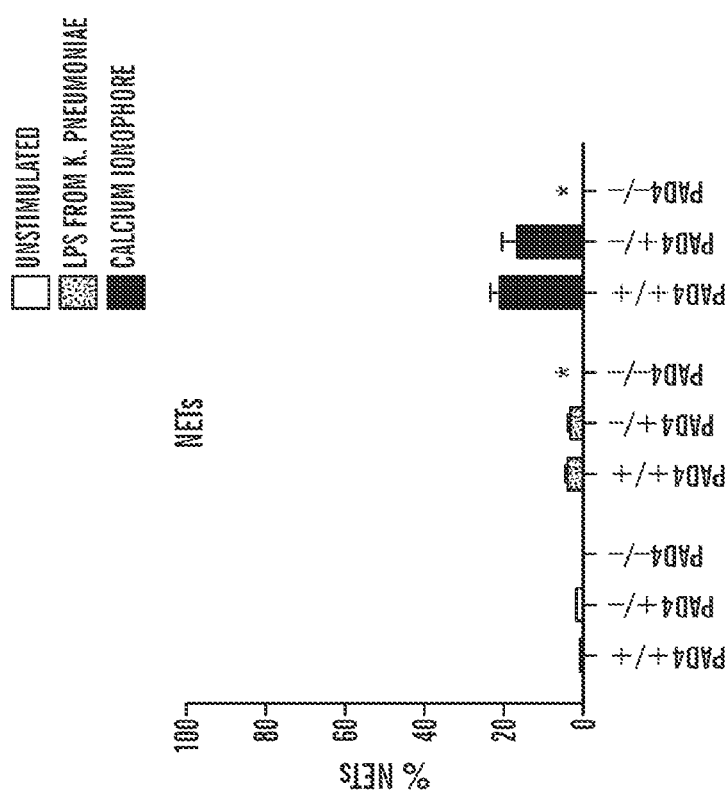
FIGS. 17A-17B show graphs that depict NETosis assays in PAD4-deficient mice and their littermates. Neutrophils were isolated from peripheral blood and stimulated with either LPS from *Klebsiella pneumoniae* (10 µM, grey bars), calcium ionophore (4 µM ionomycin, black bars), or vehicle control (RPMI+10 mM HEPES, white bars). After two hours, cells were fixed with 2% paraformaldehyde overnight and immunostaining was performed using anti-histone H3 (citrulline 2,8,17) antibody paired with ALEXA FLUOR® 488-conjugated goat anti-rabbit IgG. DNA was counterstained with Hoeschst 33342. Fluorescent images were acquired using a Zeiss AXIOVERT™ 200 inverted widefield fluorescence microscope in conjunction with a Zeiss AXIOCAM MRM™ monochromatic CCD camera and Zeiss AXIOVISION™ software. Images were quantified using IMAGEJ™ software. The x-axes indicate whether the cells were isolated from wild-type mice (PAD4+/+), PAD4-deficient mice (PAD4−/−) or mice heterozygous for PAD4 (PAD4+/−).
Figure 17B:
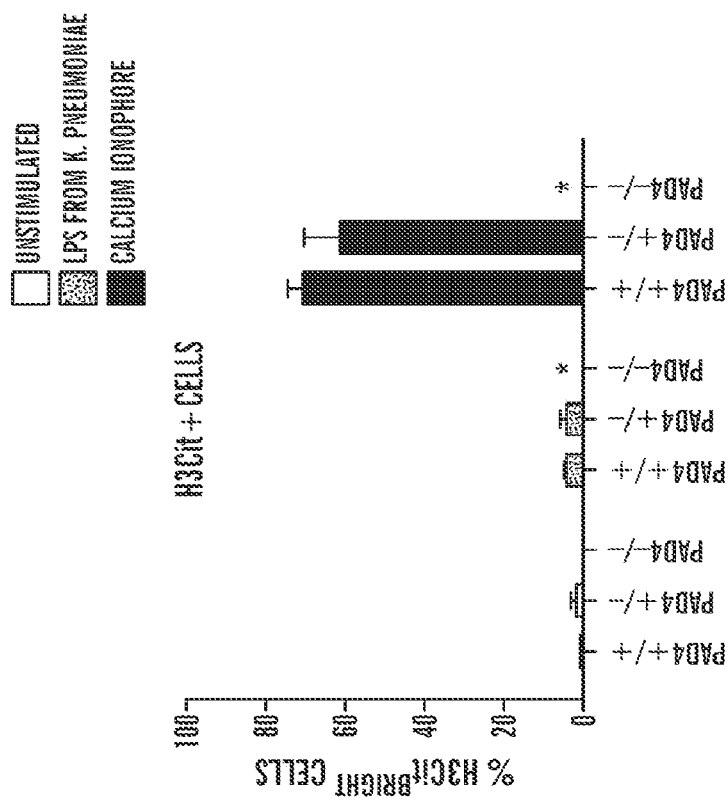

Induction of TRALI by administration of LPS and anti-H2K$^d$ mAb caused damage to the epithelium of the lungs and a dense coat of fibrous material was detectable (FIG. 15B). The fibrous material was absent in lungs from untreated mice (FIG. 15A) and in the lungs of mice with TRALI which received DNase 1 treatment (FIG. 15C). The progression of MALI was also measured by determining the platelet counts and the protein concentration found in bronchial alveolar lavage (BAL) of the mice. Whereas mice suffering from TRALI and receiving control treatments were found to have decreased platelets (FIG. 16A) and increased BAL protein levels, (FIG. 16B), these effects were diminished if the mice received intranasal administration of DNaseI (FIGS. 16A-16B).

Example 7

PAD4 and DVT

First described by Brinkmannn et al. in 2004, there is a rapidly growing literature showing that NETs play an important role in the innate immune response, particularly by their entrapment of extracellular pathogens (Brinkmannn et al. Science 2004). Furthermore, NETs are involved in the promotion of thrombus formation (Fuchs et al. PNAS 2010) and can induce coagulation (Massberg et al. Nat. Med. 2010). While little is currently known about the molecular mechanisms involved in the process of NET formation, histone hypercitrullination by the enzyme peptidylarginine deiminase 4 (PAD4) has been demonstrated in the NET formation process (Neeli et al. J Immunol 2008, Wang et al. J Cell Biol 2009). PAD4 is a member of the PAD family of enzymes, which convert protein arginine residues to citrulline through a deimination reaction. PAD4 is the only PAD family member with a nuclear localization signal and therefore can enter the nucleus to modify histones (Nakashima et al. J Biol. Chem. 2002) In PAD4$^{-/-}$ mice, a complete loss of NETs formation was seen in vitro along with a resulting impairment in innate immune responses to bacterial infection in vivo (Li et al. J Exp. Med. 2010). Therefore, the role of this histone modification in the process of NET formation is of great interest.

Described herein is data indicating PAD4 involvement in several models involving neutrophils in the lab as seen by immunofluorescence staining of tissue and isolated neutrophils for citrullinated histone H3, a product of PAD4 activity.

Using mouse models of deep vein thrombosis (DVT), we have investigated the role of PAD4 and NETs in vivo. As described elsewhere herein, the inventors have previously demonstrated that biomarkers of NETs are abundant in baboon and mouse DVT. Pretreatment of mice with DNaseI, which degrades NETs, greatly reduces the incidence of thrombosis in wild-type mice. Described in this Example herein, is a venous stenosis model of DVT in mice in which PAD4$^{-/-}$ mice are being studied. Briefly, the inferior vena cava is ligated to induce a 90% restriction in blood flow. This results in the formation of a thrombus that is similar in composition to human deep vein thrombi: a platelet-rich white portion distal to the ligation site and an erythrocyte-rich red portion proximal to the ligation site, with neutrophils present throughout the thrombus. Neutrophils with citrullinated histones and extracellular H3Cit were identified in these thrombi at 48 hours after ligation (data not shown).

Figure 18A:
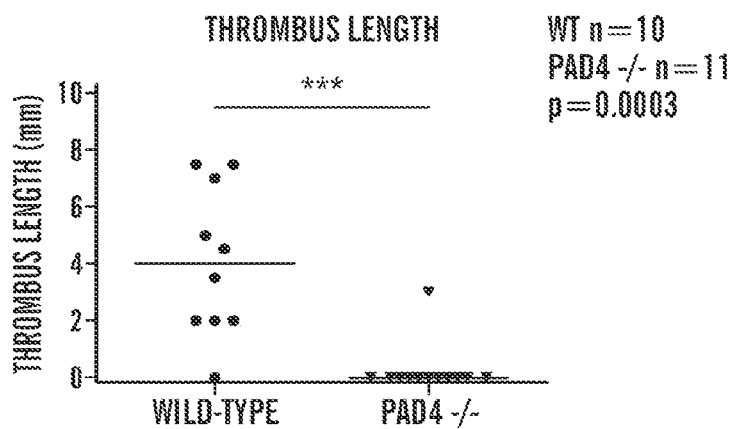
FIGS. 18A and 18B show graphs depicting decreased thrombus size and frequency of formation in PAD4−/− mice compared to wild-type C57Bl/6J mice from 48 h DVT in the venous stenosis model. The inferior vena cava was surgically exposed 48 h after ligation and the IVC opened between the renal and iliac veins to expose thrombi for harvest.

A lack of NET formation in these mice should result in reduced thrombus size and/or frequency of formation. Since PAD4-deficient mice do not form NETs in vitro, it was hypothesized that NET formation would be greatly impaired in these mice and this would either prevent or delay thrombus formation in these mice. Therefore, the IVC stenosis model of DVT was examined in PAD4$^{-/-}$ mice with C57Bl/6 mice (wld type) as controls. Mice were anesthetized with isoflurane and given buprenorphine as an analgesic prior to beginning surgery. A midline laparotomy was performed and the inferior vena cava exposed. Side branches of the IVC below the renal veins were completely ligated and the IVC was ligated in the presence of a 30 g spacer immediately below the renal veins. The inventors have previously seen that this results in a 90% reduction in vessel diameter. The mice were then sutured and monitored over a 48-hour period. At 48 hours, mice were anesthetized and 300 microliters of blood was collected through the retroorbital sinus. The midline incision was re-opened and the IVC exposed. Presence or absence of a thrombus was determined by cutting open the IVC between the renal veins and the iliac vein. Thrombi were collected, washed, measured for length and then immediately frozen for further analysis (FIG. 18A).

Figure 18B:
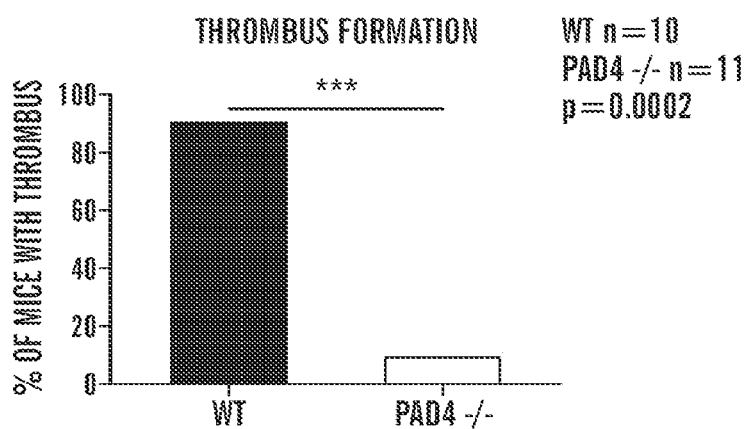

While a majority of wild-type mice (9/10) form a thrombus at 48 hours, the incidence of thrombus formation was greatly reduced in PAD4 mice (1/11) at this time point (FIG. 18B). These results indicate that these mice can be used to further study NETs involvement in thrombosis pathogenesis in vivo, and that PAD4 inhibitors will be beneficial in preventing deep vein thrombosis in humans.

Inhibitors of PAD4 have been previously described (Luo et al. Biochemistry 2006). They have been studied in vitro with primary human neutrophils and a human granulocyte precursor cell line (HL-60 cells). Cl-amidine has been shown in vivo in mouse models of arthritis (Willis et al. JI 2011) and colitis (Chumanevich et al. Am J Physiol Gastrointest Liver Physiol 2011) to reduce clinical signs in both conditions. Two of these, Cl-amidine and F-amidine, have recently become commercially available through Cayman Chemical (Cl-amidine: Catalog number 10599, CAS 913723-61-2, F-amidine: Catalog number 10610). These inhibitors bind to cysteine 645 in the active site of the enzyme, irreversibly inhibiting enzyme activity. These inhibitors are not selective and also inhibit other PAD family members.

References for Example 7

Brinkmannn et al. Science 2004, 303:1532-1535.
Fuchs et al. PNAS 2010 107:15880-15885.
Massberg et al. Nat. Med. 2010, 16:887-896.
Neeli et al. J Immunol 2008, 180:1895-1902.
Wang et al. J Cell Biol 2009, 184: 205-213.
Nakashima et al. J Biol. Chem. 2002, 277:49562-49568.
Li et al. J Exp. Med. 2010, 207:1853-1862.
Luo et al. Biochemistry 2006, 45:11727-11736.
Willis et al. Journal of Immunology 2011, 186:4396-4404.
Chumanevich et al. Am J Physiol Gastrointest Liver Physiol 2011, 300:G929-38.

Example 8

Nets Promote Deep Vein Thrombosis in Mice

Upon activation, neutrophils can release nuclear material known as neutrophil extracellular traps (NETs), which were initially described as a part of antimicrobial defense. Extracellular chromatin was recently reported to be prothrombotic in vitro and to accumulate in plasma and thrombi of baboons with experimental deep vein thrombosis (DVT). Described herein is the exploration of the source and role of extracellular chromatin in DVT using an established murine model of DVT induced by flow restriction (stenosis) in the inferior vena cava (IVC). It is demonstrated herein that the levels of extracellular DNA increase in plasma after 6 h IVC stenosis, compared with sham-operated mice. Immunohistochemical staining revealed the presence of Gr-1-positive neutrophils in both red (RBC-rich) and white (platelet-rich) parts of thrombi. Citrullinated histone H3 (CitH3), an element of NETs' structure, was present only in the red part of thrombi and was frequently associated with the Gr-1 antigen. Immunofluorescent staining of thrombi showed proximity of extracellular CitH3 and von Willebrand factor (VWF), a platelet adhesion molecule crucial for thrombus development in this model. Infusion of Deoxyribonuclease 1 (DNase 1) protected mice from DVT after 6 h and also 48 h IVC stenosis. Infusion of an unfractionated mixture of calf thymus histones increased plasma VWF and promoted DVT early after stenosis application. Extracellular chromatin, likely originating from neutrophils, is a structural part of a venous thrombus and both the DNA scaffold and histones contribute to the pathogenesis of DVT in mice. NETs provide new targets for DVT treatment.

Material and Methods

Mice. Wild-type C57BL/6J (WT) mice were from Jackson Laboratory (Bar Harbor, Me., USA). All mice were 7-9-week-old males weighing 22-26 g.

Flow restriction model. The murine model of DVT was performed as described [22]. In brief, mice were anesthetized by isoflurane-oxygen, intestines were exteriorized and the inferior vena cava (IVC) was diligently separated from aorta. A suture was placed on the IVC just below the renal veins over a spacer (diameter of 0.26 mm) and then the spacer was removed. This procedure has been shown to decrease vascular lumen by about 90% and avoid endothelial injury. All visible IVC side branches were also sutured. Thereafter, peritoneum and skin were closed, mice were sacrificed after 1-48 h and thrombi formed in the IVC were harvested. Sham-operated mice were opened and IVC sutured similarly to the experimental mice, but the suture was removed immediately after ligation.

Histone infusion. A mixture of all histones isolated from calf thymus (Worthington, Lakewood, N.J., USA) was dissolved in sterile saline and infused intravenously in mice immediately before IVC stenosis application. The dose used (10 mg kg$^{-1}$) is known to produce a 25% decrease in platelet count 10 min after infusion [6]. The infused solution of histone mix was essentially endotoxin-free (<0.025 EU mL$^{-1}$; measured using the endotoxin detection kit [Lonza, Walkersville, Md., USA] according to the manufacturer's instructions). Control mice received infusion of sterile saline. Mice were sacrificed 1 h after surgery and thrombus formation was examined.

DNase 1 infusion. DNase 1 (PULMOZYME®, Genentech, San Francisco, Calif., USA) was diluted in sterile saline and injected immediately after surgery (50 µg intraperitoneally and 10 µg intravenously). In experiments with 48 h IVC stenosis, injections were repeated three more times after every 12 h. Control mice were injected with the PULMOZYME™ vehicle buffer (8.77 mg mL$^{-1}$ sodium chloride and 0.15 mg mL$^{-1}$ calcium chloride) diluted in sterile saline.

Determination of extracellular DNA in plasma. Blood (100 µL) was drawn from the periorbital eye plexus and stabilized with 5 µL of 0.51 M EDTA. Time points for blood drawing were: 24 h before (all mice) and then either 6, 24 and 48 h after DVT (three mice) or sham surgery (four mice), or 6 and 48 h after DVT (three mice) or sham surgery (four mice). Plasma was obtained by centrifugation at 2300 g, diluted 50-fold with PBS containing 0.1% BSA, mixed with an equal volume of 1 µM of the fluorescent DNA dye SYTOXGREEN™ (Invitrogen, Carlsbad, Calif., USA) and fluorescence of dye bound to DNA was immediately determined by a fluorescence microplate reader (Fluoroskan, Thermo Scientific, Waltham, Mass., USA) as described [4]. Background fluorescence of PBS-plasma mixture (without SYTOXGREEN™) was subtracted from all samples.

Frozen sections. Thrombi with or without the surrounding IVC wall or sham IVC (IVC fragment of 6-8 mm ligated at both ends with blood remaining inside) were harvested, embedded in Optimal Cutting Temperature (OCT) compound (Sakura Finetek, Torrance, Calif., USA) and then cryosectioned into 10-µm sections.

Immunohistochemistry. Immunohistochemistry was performed as previously described [24]. Briefly, anti-mouse Gr-1 antibody (dilution 1:500, clone RB6-8C5; BD Pharmingen, Franklin Lakes, N.J., USA) and rabbit polyclonal [CitH3] antibody to citrullinated histone H3 (dilution 1:300, citrulline 2+8+17; ab5103, Abcam, Cambridge, Mass., USA) were used as first antibodies. HISTOFINE SIMPLE STAIN MOUSE MAX PO™ for rat (414311F) and rabbit (414351F), respectively, purchased from Nichirei Corporation (Tokyo, Japan), were used as secondary antibodies. Diaminobenzidine (DAB) substrate kit (Vector Laboratories, Burlingame, Calif., USA), containing DAB and DAB-Ni, was used for visualization of staining. Finally, sections were counterstained with Nuclear Fast Red (Sigma-Aldrich, St Louis, Mo., USA). No first antibodies were applied in control sections.

Immunofluorescent staining. Sections were incubated with zinc fixative for 15 min, washed in PBS, and permeabilized with 0.1% Triton X-100, 0.1% sodium citrate on ice. After washing and blocking with 3% bovine serum albumin (BSA, Sigma-Aldrich), the sections were incubated for 16 h at 4° C. in 0.3% BSA in PBS with 0.3 µg mL$^{-1}$ rabbit polyclonal anti-CitH3 (citrulline 2+8+17; ab5103, Abcam), and sheep polyclonal anti-VWF (1:50 dilution of IgG fraction; ab11713, Abcam). For longitudinal sections of isolated thrombi, anti-CitH3 Ab was applied overnight and anti-VWF Ab for 90 min. After washing, sections were incubated with the following ALEXA FLUOR™-conjugated secondary antibodies (all from Invitrogen) in 0.3% BSA in PBS: ALEXA FLUOR 488 donkey anti-rabbit IgG and ALEXA FLUOR 568 donkey anti-sheep IgG (2 µg mL$^{-1}$ for all Abs) for 2 h at room temperature. DNA was labeled with 1 µg mL$^{-1}$ Hoechst 33342 (Invitrogen). Fluorescent images for cross-sections were acquired using an AXIOVERT™ 200 inverted widefield fluorescence microscope (Zeiss, Thornwood, N.Y., USA) in conjunction with a Zeiss AXIOCAM MRM™ monochromatic CCD camera. Mosaic reconstruction of entire cross-sections was performed with MosaicJ™ [25] for ImageJ™ software (National Institutes of Health, Bethesda, Md., USA; available on the world wide web at http://rsbrreb/nih/gov/iji) and consists of two to six fields of view per image shown. Images for longitudinal sections were obtained by a widefield fluorescence microscope using an AXIOPLAN™ microscope (Zeiss) with color HRc Zeiss camera. Images were ANALYZED WITH Axiovision™ SOFTWARE (ZEISS).

Plasma VWF measurement. The assay was performed as described [22]. The level of VWF in pooled plasma of 20 C57BL/6J WT mice was used as a reference standard.

Statistics. Results obtained on the same animal at different time points (difference in plasma DNA levels between baseline and 6 h and plasma VWF content) were compared using paired Student's t-test. Plasma DNA levels in mice with IVC stenosis and sham-operated animals were compared by Mann-Whitney test. Difference in thrombi prevalence between different groups of mice was compared using a contingency table and the chi-square test. Differences were considered significant at P<0.05.

Results

Flow Restriction in the IVC Promotes Plasma DNA Accumulation

Figure 21:
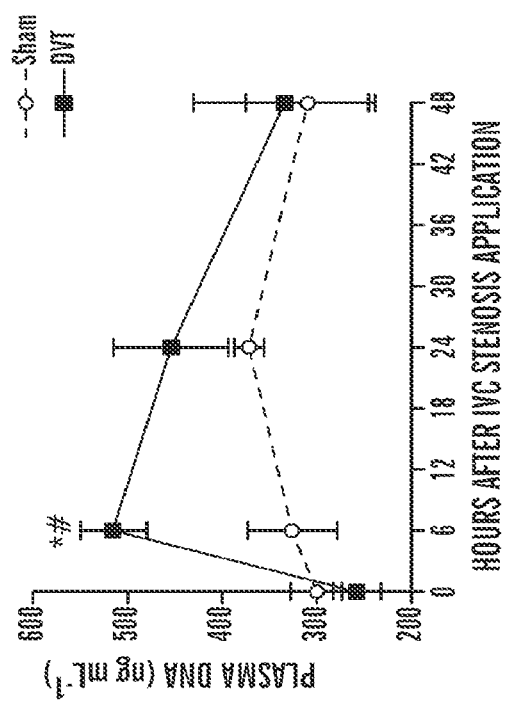
FIG. 21 depicts a graph demonstrating that plasma DNA level is elevated 6 h after IVC stenosis application. Blood was drawn from wild-type mice before and 6, 24 and/or 48 h after IVC stenosis application (DVT) or sham surgery. Plasma was prepared and DNA levels determined by SYTOXGREEN™ dye; n=3-8 per time point. *P<0.003 vs. the same mice at baseline (paired t-test). #P<0.03, 6 h DVT vs. sham-operated mice (Mann-Whitney test). Error bars represent SEM.

IVC stenosis was performed in WT mice. Blood was drawn 24 h before and 6, 24 and 48 h after surgery and plasma DNA levels were measured. Plasma of non-operated mice contained 284±18.9 ng mL$^{-1}$ DNA. Stenosis of the IVC led to an increase in plasma DNA levels 6 h post surgery (FIG. 21) to 515±34.7 ng mL$^{-1}$ (P<0.003 vs. baseline and P<0.03 vs. sham-operated mice). This effect did not result from the surgical procedure because sham-operated mice had plasma DNA levels similar to non-operated animals (326±47.4 ng mL$^{-1}$, P=0.9). The concentration of DNA in plasma 48 h after surgery returned to baseline and was not different in DVT- and sham-operated mice. Appearance of DNA in plasma 6 h after stenosis application, when about half of the mice form visible thrombi (as described in the text), indicates that chromatin release occurs early in the thrombotic process.

Venous Thrombi Contain CitH3 Located Predominantly in the Red Part of the Thrombus.

Besides neutrophils, other cell types can release chromatin [8-10]. Histone citrullination by PAD4 occurs in activated granulocytes and is necessary for the formation and release of NETs [14-16,26]. To assess the presence of NETs in venous thrombi, thrombi developed in mice after 48 h IVC stenosis were stained for CitH3. The white part of the thrombus (the platelet-rich part remote from the suture) contained numerous Gr-1-positive cells but was essentially devoid of CitH3 (data not shown). Gr-1 is an antigen present on polymorphonuclear leukocytes and also on plasmacytoid dendritic cells and a small subset of monocytes (reviewed in [27]). The large red part of the thrombus (the RBC-rich part proximal to the suture) contained loci heavily stained for either Gr-1 only (or both Gr-1 and CitH3 with substantial overlap of the two antigens (data not shown). Some Gr-1-positive cells formed extracellular fiber-like structures that strongly stained for CitH3, probably representing NETs.

VWF can play a role in venous thrombosis initiation [22]. As described above herein, in baboon DVT thrombi, extracellular DNA was shown to co-localize with VWF. Immunofluorescent staining for VWF in murine venous thrombi was often associated with extracellular CitH3 staining in the red part of thrombi (data not shown). Multiple CitH3-positive cells were also revealed by the immunofluorescent staining in the core of the red part of thrombi, confirming the immunohistochemical data described above herein (data not shown). No substantial CitH3 staining was observed in the white part of thrombi, IVC wall, sham-operated IVC, and in control sections stained without first antibody. Thus, histones present in murine IVC thrombi are likely to originate from neutrophils releasing NETs predominantly in the red part of thrombi. In mice, similar to baboon, thrombi extracellular chromatin frequently co-distributes with VWF.

Histones Increase Plasma VWF Levels and Promote DVT.

Extracellular histones are cytotoxic to endothelial cells and activate platelets in vitro; histone infusion at a high dose of 75 mg kg$^{-1}$ is lethal to mice [4,28]. Therefore a lower dose (10 mg kg$^{-1}$) of histone mix, a dose that produces only mild thrombocytopenia [6], was used to test whether it renders mice more prone to venous thrombosis. Only two of 14 vehicle-treated mice (14%) produced thrombi after 1 h IVC stenosis (FIGS. 22A-22C), while five of nine mice that received histones prior to the surgery (55%) developed a thrombus (P<0.04).

Histones have been shown to cause Ca$^{2+}$ influx in different cell types [6,29,30]. Increase in intracellular Ca$^{2+}$ level triggers VWF secretion from endothelial cells and platelets, with some of the VWF remaining associated with the plasma membrane of these cells [31]. Platelet recruitment mediated by VWF is a key step in the initiation of venous thrombosis in this model of DVT [22]. Therefore stimulation of VWF secretion could be one of the mechanisms responsible for the prothrombotic effect of histones. Indeed, histone infusion increased plasma VWF levels compared with baseline (Table 1). In contrast, VWF plasma levels in vehicle-treated mice remained unchanged. Thus, histone infusion increases plasma concentration of VWF, which could contribute to the effect of histones on DVT in the flow restriction setting.

DNase 1 Infusion Protects Mice from DVT

Based on the presence of histones, DNA and NET-like structures in deep vein thrombi in baboons and mice (as described herein) and on the ability of DNase 1 to disassemble NET-induced thrombi in a flow chamber, it was hypothesized that DNase 1 might prevent DVT in vivo. To test this possibility, DNase 1 was infused in mice immediately after surgery and thrombosis examined after 6 or 48 h of IVC stenosis (in 48-h DVT experiments, infusions were repeated every 12 h). In the 6-h model, half (seven of 14) of the vehicle-treated mice produced a thrombus (FIGS. 13A-13F), whereas in mice that received DNase 1, only one mouse of 10 formed a thrombus (P<0.05). In the 48-h IVC stenosis model, mice treated with control buffer developed a thrombus in 63% of cases (five of eight), whereas thrombus prevalence in mice treated with DNase 1 was 17% (two of 12, P<0.04). These data suggest that extracellular chromatin may play a role in flow restriction-induced thrombosis and DNase 1 infusion is protective against thrombosis in this model.

Several cell types have been shown to release extracellular chromatin upon activation. The role of the nuclear material originating from neutrophils, NETs, in antimicrobial defense has been convincingly demonstrated [2]. Described herein is data implicating extracellular chromatine in thrombosis because NETs can form a scaffold able to recruit both platelets and RBCs in vitro. Perfusion of blood over NETs in a flow chamber results in the formation of a red thrombus, which was entirely NET-dependent as DNase 1, which destroys NETs, prevented recruitment of both cell types. This suggested a mechanistic link between NETs and DVT because (i) recruitment of platelets is one of the early events pivotal for thrombus initiation in mice and (ii) DVT thrombi are rich in RBCs. Thrombi developed in the murine flow restriction model of DVT also consist of a large RBC-rich red part and a smaller platelet-rich white part with both parts containing fibrin. Thus, thrombi formed in this murine model share close morphological similarity to human DVT thrombi, which also include white and red parts.

Thrombi obtained in an experimental DVT model in baboons have been shown herein to contain extracellular DNA, H3 and DNA/H2A/H2B complex. It is further demonstrated herein that histone H3 is also abundantly present in murine DVT thrombi. Histone H3 was citrullinated, indicating that it is likely to have originated from neutrophils forming NETs. PAD4, the enzyme responsible for arginine conversion to citrulline, is abundantly expressed in granulocytes [15,16]. Staining for Gr-1, a neutrophil marker, revealed neutrophil presence in both red and white parts of the murine venous thrombi. Neutrophil-specific staining in the red part of thrombi was frequently associated with CitH3, with CitH3 being either confined to nuclei or localized extracellularly. Without wishing to be bound by theory, this suggests that here neutrophils are at different stages of NETosis. Interestingly, little CitH3-positive staining was observed in the white part of thrombi despite abundant presence of Gr-1-positive cells. As NETosis is an irreversible process, one may speculate that neutrophils in the white part have spent less time in the thrombus compared with the red part neutrophils. This may suggest that the white part, originally adjacent to the stenosis site where thrombus growth begins, has a role in recruiting neutrophils from the surrounding blood. This is likely to be through binding to the activated platelets. Later on, these neutrophils may also become activated and form NETs, which in turn would contribute to recruitment of RBCs and the formation of red thrombus.

The model described herein corroborates the reported ability of stimulated platelets to bind neutrophils and induce formation and release of NETs [3,5]. In addition, flow restriction may create hypoxic conditions in the vessel wall and cells buried inside a thrombus are exposed to even more severe hypoxia due to isolation from the blood stream. Hypoxia potentiates the release of ROS [32]. Besides neutrophils, platelets also can generate ROS, such as superoxide [33]. It has been shown that ROS not only directly contribute to thrombosis [34] but also can trigger formation of NETs [13,35]. Therefore, the adherent neutrophils exposed to two major triggers of NETs production, activated platelets and ROS, release extracellular chromatin, which then contributes to further thrombus development.

At the early stages of flow restriction, massive recruitment of both platelets and leukocytes to the endothelium occurs simultaneously [22]. It has recently been reported that co-culture of neutrophils with activated endothelial cells can also induce NET formation, which in turn promotes endothelial damage [36]. As the activation state of the endothelium is critical for DVT initiation [22], it is possible that NETs-endothelial interactions could be involved in thrombus initiation. This fits with the observation made herein that NETs biomarkers accumulate in plasma within hours after flow restriction induction and that histones cause an increase in plasma VWF levels, probably from the activated endothelium.

As NETs are generated during the early stage of thrombus initiation and are also abundantly present in mature thrombi, it would be reasonable to hypothesize that NETs degradation might affect thrombosis. Here, infusion of DNase 1 protected mice from flow restriction-induced DVT regardless of the length of stenosis (6 or 48 h, FIG. 13A-13F). Without wishing to be bound by theory, as no visible thrombus was detected in most DNase 1-treated mice, DNase 1 apparently cleaves NETs early, disrupting the pathways of cellular activation and preventing the cascade of events leading to thrombosis. Without wishing to be bound by theory, the anti-thrombotic effect of DNase 1 is likely to be mediated by removal of NETs generated locally at the site of stenosis, similar to cleavage of endothelium-bound VWF by ADAMTS13. Similar to ADAMTS13, DNase 1 infusion may not reduce the amount of circulating DNA but rather affect its size and local concentration.

It is known that blood coagulation contributes to DVT and hypercoagulable states are considered risk factors for the disease [19-21]. The murine DVT model used herein recapitulates this feature of human DVT because fibrin could be detected throughout the thrombus [22]. Although anticoagulants have not been tested in this model, a procoagulant state, such as in mice with high plasma levels of soluble P-selectin [38], is associated with increased DVT induced by stasis in the IVC [39].

As described herein, strings of extracellular CitH3 frequently co-localized with VWF in the thrombi produced by IVC stenosis. This finding corroborates in vitro observations that histone [40] and NETs bind VWF [4]. Secretion of VWF from Weibel-Palade bodies (WPBs) to the surface of endothelial cells appears required for the development of DVT in mice [22].

Interestingly, VWF expression is downregulated in the venous valvular sinus, which experiences stasis and hypoxia, likely to maintain a thromboresistant phenotype at this thrombosis-susceptible site [41]. In thrombi, VWF may originate not only from endothelium but also from platelets, in which it is stored in alpha-granules. VWF and NETs may form a mutually supportive network that contributes to VWF A1 domain activation [31] and to growth and stabilization of a venous thrombus.

Figure 22C:
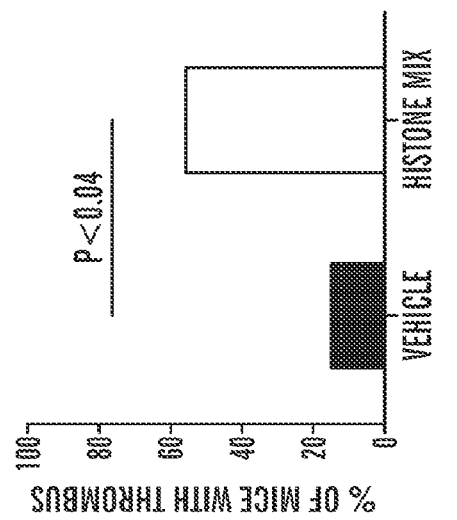
FIGS. 22A-22C depict graphs demonstrating that histone infusion promotes flow restriction-induced thrombosis in mice. Histone mix (10 mg kg$^{-1}$) was infused into WT mice immediately before DVT surgery. Mice were sacrificed after 1 h stenosis and thrombi developed in the IVC were examined and harvested. Values for weight (FIG. 22A) and length (FIG. 22B) of the thrombi are shown with medians (horizontal bars).
Figure 22B:
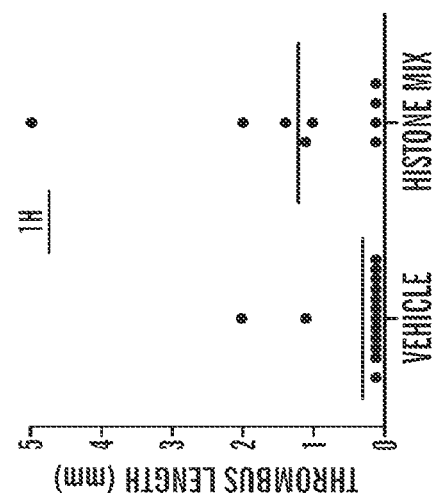
Figure 22A:
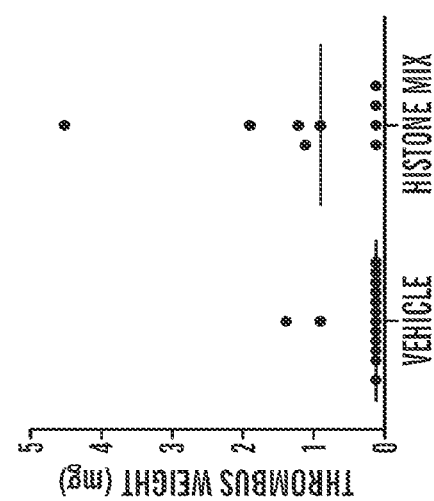

Histones also are likely to participate in the process of thrombus initiation. Infusion of histone mix facilitated thrombosis in mice (FIGS. 22A-22C). This may result from the observed deleterious effect of histones on endothelium in vitro [28], which at a lower dose in vivo might activate endothelium and stimulate the release of VWF as observed herein (Table 1). Another prothrombotic effect of histones could result from activation of platelets [4,6]. Activated platelets can stimulate NETs production [3,5] and promote release of WPBS [42], leading to further recruitment of platelets and leukocytes. In either case, histones would contribute to the process of thrombus initiation and propagation.

In conclusion, it is demonstrated herein that NETs have an important functional role of NETs in DVT induced by flow restriction, thereby providing targets for treatment of DVT References for Example 8

1. Brinkmann V, Zychlinsky A. Beneficial suicide: why neutrophils die to make NETs. *Nat Rev Microbiol* 2007; 5: 577-82.
2. Brinkmann V, Reichard U, Goosmann C, Fauler B, Uhlemann Y, Weiss DS, Weinrauch Y, Zychlinsky A. Neutrophil extracellular traps kill bacteria. *Science* 2004; 303: 1532-5.
3. Clark SR, Ma AC, Tavener SA, McDonald B, Goodarzi Z, Kelly MM, Patel KD, Chakrabarti S, McAvoy E, Sinclair GD, Keys EM, Allen-Vercoe E, Devinney R, Doig CJ, Green FH, Kubes P. Platelet TLR4 activates neutrophil extracellular traps to ensnare bacteria in septic blood. *Nat Med* 2007; 13: 463-9.
4. Fuchs TA, Brill A, Duerschmied D, Schatzberg D, Monestier M, Myers DD Jr, Wrobleski SK, Wakefield TW, Hartwig JH, Wagner D D. Extracellular DNA traps promote thrombosis. *Proc Natl Acad Sci USA* 2010; 107: 15880-5
5. Massberg S, Grahl L, von Bruehl ML, Manukyan D, Pfeiler S, Goosmann C, Brinkmann V, Lorenz M, Bidzhekov K, Khandagale AB, Konrad I, Kennerknecht E, Reges K, Holdenrieder S, Braun S, Reinhardt C, Spannagl M, Preissner KT, Engelmann B. Reciprocal coupling of coagulation and innate immunity via neutrophil serine proteases. *Nat Med* 2010; 16: 887-96
6. Fuchs TA, Bhandari AA, Wagner DD. Histones induce rapid and profound thrombocytopenia in mice. *Blood* 2011; 118: 3708-14
7. Semeraro F, Ammollo CT, Morrissey JH, Dale GL, Friese P, Esmon NL, Esmon CT. Extracellular histones promote thrombin generation through platelet-dependent mechanisms: involvement of platelet TLR2 and TLR4. *Blood* 2011; 118: 1952-61
8. von Kockritz-Blickwede M, Goldmann O, Thulin P, Heinemann K, Norrby-Teglund A, Rohde M, Medina E. Phagocytosis-independent antimicrobial activity of mast cells by means of extracellular trap formation. *Blood* 2008; 111: 3070-80
9. Chow OA, von Kockritz-Blickwede M, Bright AT, Hensler ME, Zinkernagel AS, Cogen AL, Gallo RL, Monestier M, Wang Y, Glass CK, Nizet V. Statins enhance formation of phagocyte extracellular traps. *Cell Host Microbe* 2010; 8: 445-54
10. Yousefi S, Gold JA, Andina N, Lee JJ, Kelly AM, Kozlowski E, Schmid I, Straumann A, Reichenbach J, Gleich GJ, Simon H U. Catapult-like release of mitochondrial DNA by eosinophils contributes to antibacterial defense. *Nat Med* 2008; 14: 949-53
11. Gupta AK, Hasler P, Holzgreve W, Gebhardt S, Hahn S. Induction of neutrophil extracellular DNA lattices by placental microparticles and IL-8 and their presence in preeclampsia. *Hum Immunol* 2005; 66: 1146-54
12. Kessenbrock K, Krumbholz M, Schonermarck U, Back W, Gross W L, Werb Z, Grone HJ, Brinkmann V, Jenne D E. Netting neutrophils in autoimmune small-vessel vasculitis. *Nat Med* 2009; 15: 623-5
13. Fuchs TA, Abed U, Goosmann C, Hurwitz R, Schulze I, Wahn V, Weinrauch Y, Brinkmann V, Zychlinsky A. Novel cell death program leads to neutrophil extracellular traps. *J Cell Biol* 2007; 176: 231-41
14. Wang Y, Li M, Stadler S, Correll S, Li P, Wang D, Hayama R, Leonelli L, Han H, Grigoryev SA, Allis CD, Coonrod SA. Histone hypercitrullination mediates chromatin decondensation and neutrophil extracellular trap formation. *J Cell Biol* 2009; 184: 205-13
15. Nakashima K, Hagiwara T, Yamada M. Nuclear localization of peptidylarginine deiminase V and histone deimination in granulocytes. *J Biol Chem* 2002; 277: 49562-8
16. Li P, Li M, Lindberg MR, Kennett MJ, Xiong N, Wang Y. PAD4 is essential for antibacterial innate immunity mediated by neutrophil extracellular traps. *J Exp Med* 2010; 207: 1853-62
17. Heit JA. The epidemiology of venous thromboembolism in the community. *Arterioscler Thromb Vasc Biol* 2008; 28: 370-2
18. Ammollo CT, Semeraro F, Xu J, Esmon NL, Esmon CT. Extracellular histones increase plasma thrombin generation by impairing thrombomodulin-dependent protein C activation. *J Thromb Haemost* 2011; 9: 1795-803
19. Griffin JH, Evatt B, Zimmerman TS, Kleiss AJ, Wideman C. Deficiency of protein C in congenital thrombotic disease. *J Clin Invest* 1981; 68: 1370-3
20. Dahlback B, Carlsson M, Svensson PJ. Familial thrombophilia due to a previously unrecognized mechanism characterized by poor anticoagulant response to activated protein C: prediction of a cofactor to activated protein C. *Proc Natl Acad Sci USA* 1993; 90: 1004-8
21. Bertina RM, Koeleman BP, Koster T, Rosendaal FR, Dirven RJ, de Ronde H, van der Velden PA, Reitsma PH. Mutation in blood coagulation factor V associated with resistance to activated protein C. *Nature* 1994; 369: 64-7
22. Brill A, Fuchs TA, Chauhan AK, Yang JJ, De Meyer SF, Kollnberger M, Wakefield TW, Lammle B, Massberg S, Wagner DD. von Willebrand factor-mediated platelet adhesion is critical for deep vein thrombosis in mouse models. *Blood* 2011; 117: 1400-7
23. Sevitt S. The structure and growth of valve-pocket thrombi in femoral veins. *J Clin Pathol* 1974; 27: 517-28
24. Savchenko AS, Hasegawa G, Naito M. Development and maturation of thymic dendritic cells during human ontogeny. *Cell Tissue Res* 2006; 325: 455-60
25. Thevenaz P, Unser M. User-friendly semiautomated assembly of accurate image mosaics in microscopy. *Microsc Res Tech* 2007; 70: 135-46
26. Neeli I, Khan SN, Radic M. Histone deimination as a response to inflammatory stimuli in neutrophils. *J Immunol* 2008; 180:1895-902
27. Egan CE, Sukhumavasi W, Bierly AL, Denkers EY. Understanding the multiple functions of Gr-1(+) cell subpopulations during microbial infection. *Immunol Res* 2008; 40: 35-48
28. Xu J, Zhang X, Pelayo R, Monestier M, Ammollo CT, Semeraro F, Taylor FB, Esmon NL, Lupu F, Esmon CT. Extracellular histones are major mediators of death in sepsis. *Nat Med* 2009; 15: 1318-21
29. Gamberucci A, Fulceri R, Marcolongo P, Pralong WF, Benedetti A. Histones and basic polypeptides activate $Ca^{2+}$/cation influx in various cell types. *Biochem J* 1998; 331 (Pt 2): 623-30
30. Kleine TJ, Lewis PN, Lewis S A. Histone-induced damage of a mammalian epithelium: the role of protein and membrane structure. *Am J Physiol* 1997; 273: C1925-36
31. Wagner DD. Cell biology of von Willebrand factor. *Annu Rev Cell Biol* 1990; 6: 217-46
32. Guzy RD, Schumacker PT. Oxygen sensing by mitochondria at complex III: the paradox of increased reactive oxygen species during hypoxia. *Exp Physiol* 2006; 91: 807-19
33. Marcus AJ, Silk ST, Safier LB, Ullman HL. Superoxide production and reducing activity in human platelets. *J Clin Invest* 1977; 59:149-58
34. Jin RC, Mahoney CE, Coleman Anderson L, Ottaviano F, Croce K, Leopold JA, Zhang YY, Tang SS, Handy DE, Loscalzo J. Glutathione peroxidase-3 deficiency promotes platelet-dependent thrombosis in vivo. *Circulation* 2011; 123: 1963-73
35. Nishinaka Y, Arai T, Adachi S, Takaori-Kondo A, Yamashita K. Singlet oxygen is essential for neutrophil extracellular trap formation. *Biochem Biophys Res Commun* 2011; 413: 75-9
36. Gupta AK, Joshi MB, Philippova M, Erne P, Hasler P, Hahn S, Resink TJ. Activated endothelial cells induce neutrophil extracellular traps and are susceptible to NETosis-mediated cell death. *FEBS Lett* 2010; 584: 3193-7
37. Hakkim A, Furnrohr BG, Amann K, Laube B, Abed UA, Brinkmann V, Heiiniann M, Voll RE, Zychlinsky A. Impairment of neutrophil extracellular trap degradation is associated with lupus nephritis. *Proc Natl Acad Sci USA* 2010; 107: 9813-8
38. Andre P, Hartwell D, Hrachovinova I, Saffaripour S, Wagner DD. Pro-coagulant state resulting from high levels of soluble P-selectin in blood. *Proc Natl Acad Sci USA* 2000; 97: 13835-40
39. Myers DD, Hawley AE, Farris DM, Wrobleski SK, Thanaporn P, Schaub RG, Wagner DD, Kumar A, Wakefield T W. P-selectin and leukocyte microparticles are associated with venous thrombogenesis. *J Vasc Surg* 2003; 38: 1075-89
40. Ward CM, Tetaz TJ, Andrews RK, Berndt MC. Binding of the von Willebrand factor A1 domain to histone. *Thromb Res* 1997; 86:469-77
41. Brooks EG, Trotman W, Wadsworth MP, Taatjes DJ, Evans MF, Ittleman FP, Callas PW, Esmon CT, Bovill EG. Valves of the deep venous system: an overlooked risk factor. *Blood* 2009; 114: 1276-9
42. Dole VS, Bergmeier W, Mitchell HA, Eichenberger SC, Wagner DD. Activated platelets induce Weibel-Palade-body secretion and leukocyte rolling in vivo: role of P-selectin. *Blood* 2005; 106: 2334-9

TABLE 1

Histone infusion elevates plasma VWF levels. Blood was drawn 24 h before and 1 h after infusion of saline or histone mix (10 mg kg$^{-1}$). P value was calculated by the paired t-test. Saline-injected mice, n = 8; histone-injected mice, n = 6

| Saline | | Histone mix | |
|---|---|---|---|
| Baseline | 1 h after infusion | Baseline | 1 h after infusion |
| 83 ± 2.7% | 78 ± 5.2% | 78 ± 4.2% | 94 ± 6.7% |
| — | P = 0.43 | — | P < 0.003 |

Example 9

Extracellular DNA Traps are Formed during TRALI

Transfusion-related acute lung injury (TRALI) is the leading cause of transfusion-related death. The biological processes contributing to TRALI are poorly understood. All blood products can cause TRALI, and no specific treatment is available. A "two-event model" has been proposed as the trigger. The first event may include surgery, trauma or infection; the second involves the transfusion of anti-leukocyte antibodies or bioactive lipids within the blood product. Together, these events induce neutrophil activation in the lungs, causing endothelial damage and capillary leakage. Neutrophils, in response to pathogens or under stress, can release their chromatin coated with granule contents, thus forming neutrophil extracellular traps (NETs). Although protective against infection, these NETs are injurious to tissue. It is demonstrated herein that NET biomarkers are present in TRALI patients' blood and that NETs are produced in vitro by primed human neutrophils when challenged with anti-HNA-3a antibodies previously implicated in TRALI. NETs are found in alveoli of mice experiencing antibody-mediated TRALI. DNase 1 inhalation prevents their alveolar accumulation and improves arterial oxygen saturation even when administered 90 minutes after TRALI onset. Accordingly, NETs can be targeted to prevent or treat TRALI.

TRALI is a rare but serious complication of blood transfusion that occurs within 6 hours of transfusion and is characterized by hypoxemia, respiratory distress and pulmonary infiltrates.[1] Over the past years prevention measures have resulted in a significant reduction in cases. However, TRALI is still the leading cause of transfusion-related mortality and its prevalence is likely underestimated; one study suggested that over 2% of cardiac surgery patients are affected.[2] Only supportive treatment is available to the patient, including mechanical ventilation and oxygen supplementation. Many of the severe cases have been linked to the presence of anti-neutrophil antibodies in the transfused product.[3,4] These antibodies bind to the recipients' neutrophils, activate them and induce sequestration in the pulmonary capillaries, resulting in tissue injury.[5] Activated neutrophils can release neutrophil extracellular traps (NETs)[6] that are composed of DNA fibers decorated with histones and antimicrobial proteins[7] originally contained in the neutrophil granules. The structure and the composition of NETs allow them to trap and prevent the spread of pathogens and also to kill Gram-negative and Gram-positive bacteria, as well as yeast.[6] NET formation follows a specific pattern characterized by histone hypercitrullination,[8] chromatin decondensation, dissolution of the granular and nuclear membranes and cytolysis.[9] Despite NETs' beneficial antimicrobial function,[6,10] their formation at the wrong time, in the wrong place or in the wrong amount can have a negative effect on the host. NETs and their components can be injurious to tissue[11-13] and they have been shown to contribute to the pathology of several inflammatory diseases.[12-17]

The purpose of the experiments described in this Example was to determine whether NETs are formed in patients with TRALI and contribute to TRALI in a mouse model. Antibodies implicated in severe TRALI and directed against the human neutrophil alloantigen-3a (HNA-3a) have been identified and shown to bind to choline-like transporter 2 (CLT-2) on the recipients' neutrophils.[18,19] It was evaluated herein whether the antibody enhances NET formation in vitro in human neutrophils expressing HNA-3a. Also investigated herein was whether NETs were formed in the lungs of mice with TRALI.

Methods

Human Samples. Blood samples from five patients with TRALI, three blood donors whose plasma caused TRALI and eleven healthy control subjects were included in the study. TRALI was diagnosed in patients according to the international consensus definition.[1] Studies involving human subjects were approved by the Institutional Review Boards of the Immune Disease Institute and the Blood Center of Wisconsin. The investigation conforms to the principles outlined in the Declaration of Helsinki.

Experimental Mice. Experiments were performed using 8-10 week old BALB/c male mice purchased from the Jackson Laboratory. All mice were housed in the animal facility at the Immune Disease Institute. Experimental procedures performed on the mice were approved by the Animal Care and Use Committee of the Immune Disease Institute.

Two-Event TRALI Model. The model was adapted from Looney et al. (2009).[20] Male BALB/c mice (8-10 week old) were primed with an i.p. injection of LPS (0.1 or 0.5 mg/kg, as indicated in the text) 24 hours prior to challenge with anti-H-2K$^d$ mAb (clone 34-1-2s, 1 mg/kg) or isotype control injected retro-orbitally. In experiments involving DNase 1 treatment, mice that were injected with both LPS and the anti-H-2K$^d$ mAb received i.n. DNase 1 (PULMOZYME®, Genentech, 50 µg/mouse, 1 µg/µl) 10 minutes before or 90 minutes after antibody injection. Control TRALI mice were injected with 50 µl of the DNase 1 vehicle-buffer in DNase 1 experiments. Blood collection, lung harvesting and arterial oxygen saturation measurements were all performed 2 hours after antibody injection. No event of TRALI-related death was recorded under these conditions in any of the treated mice.

Body Temperature Measurements. Rectal temperatures were measured as an indicator of shock-like condition 2 hours post anti-H-2K$^d$ infusion using a rectal temperature probe (MOUSEOX PLUS® system, STARR Life Sciences) connected to a POWERLAB™ data acquisition system (ADInstruments, USA).

Antibody Preparation. Anti-HNA-3a antibodies from blood donors whose plasma induced TRALI in patients and control IgG from a control donor were purified using a protein G-Sepharose column (GE Healthcare). F(ab')$_2$ fragments were generated from purified anti-HNA-3a antibody using the F(ab')$_2$ Preparation Kit (Pierce). Quality of the obtained F(ab')$_2$ was verified after electrophoresis on SDS-PAGE gel and silver stain. Anti-H-2K$^d$ antibodies were purified from the hybridoma 34-1-2s with a protein A-Sepharose column (GE Healthcare). The antibody preparation was then dialyzed and tested by electrophoresis on SDS-PAGE gel followed by silver stain, dot-blot and flow cytometry.

Blood Counts. Mouse peripheral blood counts were measured from EDTA (ethylenediaminetetraacetic acid)-anticoagulated blood with a HEMAVET™ 950 veterinary hematology analyzer (Drew Scientific). This blood counter uses two different currents to analyze the cells. A low voltage current determines the volume and the number of cells (Coulter Impedance principle) and a high voltage current that passes through the cells generates information on their internal structure such as nucleus, fluid, granules and vacuoles.

Bronchoalveolar Lavages (BAL). Mice were sacrificed and intubated with a 24-gauge cannula after their tracheas were surgically isolated. The lungs were flushed three times with 0.8 ml of sterile PBS. BAL fluids were centrifuged for 5 minutes at 800 g. Protein concentration was quantified in the supernatant using the bicinchoninic acid method.

Measurements of Blood Arterial Oxygen Saturation. Blood arterial oxygen saturation was recorded 2 hours after anti-H-2K$^d$ antibody injection, using a small rodent oxymeter sensor (MOUSE$^{OX}$™, STARR Life Sciences) mounted on the collar of each tested mouse. The 2 hour endpoint was used as per the model published by Looney and colleagues in 2009.[20-22]

Human Neutrophils. Human neutrophils were isolated from blood by dextran sedimentation followed by Ficoll-Hypaque gradient centrifugation. Briefly, 10 ml of blood containing EDTA were diluted in 10 ml of 3% Dextran and sedimented for 20 minutes. The leukocyte-rich, erythrocyte-poor upper fraction was then centrifuged at 500 g for 10 minutes to pellet the leukocytes. Leukocytes were layered with Ficoll-Hypaque and separated under centrifugation for 30 minutes at 400 g. Hypotonic red blood cell lysis was then performed to eliminate the residual erythrocytes and the neutrophils were washed in PBS and resuspended in RPMI containing 10 mM HEPES (N-2-hydroxyethylpiperazine-N'-2-ethanesulfonic acid). Neutrophil purity was routinely >98% as assessed by differential cell count after modified Wright-Giemsa staining. Blood samples from different blood donors were selected for the ability of their neutrophils to agglutinate in response to plasma containing anti-HNA-3a antibodies.

Granulocyte Agglutination Test. The granulocyte agglutination test (GAT) was performed as previously described.[11] The agglutination was observed microscopically, and the degree of agglutination was graded from – (weak) to 3+ (strong).

NET Quantification. The protocol was adapted from the method of Kessenbrock and colleagues.[14] HNA-3a-positive neutrophils were allowed to adhere on a 96-well plastic plate for 30 minutes at 37° C. The neutrophils were then primed with 5 ng/ml TNF-α and incubated with 33 nM (equivalent of 5 µg/ml) of control IgG purified from healthy volunteer blood (Control Ab), anti-HNA-3a whole IgG purified from two blood donors whose plasma induced TRALI (Ab1 or Ab2), anti-CD11a IgG (anti CD11a Ab), F(ab')$_2$ fragments (equivalent to 3.66 µg/ml) prepared from a purified anti-HNA-3a IgG preparation from a blood donor whose plasma induced TRALI (F(ab')$_2$), or with 25 nM PMA (positive control). After a 180 minute incubation, cells were fixed with 2% PFA and the DNA was stained using Hoechst 33342. The released DNA was visualized by fluorescence microscopy and percentage of cells making NETs was quantified from 7 to 9 non-overlapping fields in 3 wells for each treatment.

Extracellular DNA and Nucleosome Quantification in Plasma. Plasma DNA and extracellular nucleosomes were quantified according to manufacturer instructions using commercially available quantification kits (from Invitrogen and Roche, respectively).

Myeloperoxidase (MPO) Activity Determination. Mouse lungs were weighed, blended in 50 mmol/L potassium phosphate buffer, centrifuged, resuspended, and sonicated in potassium phosphate buffer supplemented with 50 mmol/L hexadecyltrimethylammonium bromide. After centrifugation of the cell lysates, MPO activity was assessed in the supernatant by adding tetramethylbenzidine and absorbance reading at 450 nm after stopping the reaction with sulfuric acid. For MPO quantification in mouse plasma, plasma was diluted in potassium phosphate buffer supplemented with 50 mmol/L hexadecyltrimethylammonium bromide and MPO activity was measured as previously described for lung tissue. MPO was quantified in human samples using a commercially available ELISA activity assay kit (Invitrogen) according to manufacturer instructions.

Immunohistology. Mouse lungs were fixed by intratracheal infusion of zinc fixative, then excised and bathed in zinc fixative for 2 hours at 4° C. Intratracheal inflation of the lung allowed us to conserve the three-dimensional alveolar structure. The lungs were then washed in PBS, embedded and cryosectioned into 10 µm or 50 µm sections for widefield and multiphoton fluorescence microscopy, respectively. Sections were incubated with zinc fixative for 15 minutes, washed in PBS, and permeabilized (0.1% Triton X-100, 0.1% sodium citrate) on ice. After washing and blocking (3% BSA), the sections were incubated for 2 to 16 hours at 4° C. in 0.3% BSA with 1 µg/ml anti-mouse Gr-1 (Ly-6G/C, clone RB6-8C5, BD Biosciences), 0.3 µg/ml rabbit anti-histone H3Cit (citrulline 2, 8, 17) (ab5103, Abcam), or sheep anti-mouse VWF (1:50 dilution of IgG fraction, ab11713, Abcam). Sections were then washed and incubated with the following Alexa-conjugated secondary antibodies (Invitrogen) in 0.3% BSA: Alexa 555-goat anti-rat IgG (2 µg/ml), Alexa 488-donkey ant-rabbit IgG (1.5 µg/ml), or Alexa 568-donkey anti-sheep IgG (2 µg/ml) for 2 to 4 hours at room temperature. DNA was labeled with 1 µg/ml Hoechst 33342 (Invitrogen) prior to mounting. Fluorescent images were acquired using a Zeiss Axiovert 200 inverted fluorescence microscope in conjunction with a Zeiss AXIOCAM MRM™ monochromatic CCD camera and analyzed with AXIOVISION™ software (Zeiss) or using a Zeiss AXIOPLAN™ upright fluorescence microscope in conjunction with a Hamamatsu CCD Camera coupled to an image intensifier (videoscope), and analyzed with SLIDEBOOK™ software (Intelligent Imaging Innovations).

Multiphoton Fluorescence Microscopy. A custom-built ULTIMA™ system from Prairie Technologies was used. The microscope was equipped with a water immersion objective (20×/0.95 numeric aperture), a laser scanning microscopy device which incorporates a computer with beam-conditioning equipment, and a scanhead connected to an Olympus IX50 microscope stand. For multiphoton excitation and second-harmonic generation, a MaiTai Ti:sapphire laser (Spectra-Physics) was tuned to 1000 nm to balance excitations of various fluorescent probes used. Emitted light and second-harmonic signals were detected through 455/70-nm, 525/50-nm and 590/50-nm band-pass filters with non-descanned detectors for the generation of three-color images. Sequences of image stacks were transformed into volume-rendered movies with VOLOCITY™ (Improvision) or IMARIS™ (Bitplane Scientific Solutions) softwares. Only 50 μm-thick lung tissue cryosections were analyzed.

Transmission Electron Microscopy. Mouse lungs were fixed by intratracheal infusion of 1.5% formaldehyde/1.5% glutaraldehyde in sodium cacodylate buffer (pH 7.35), excised and bathed in the same solution for 2 hours at 4° C. The fixed lungs were sliced into 0.5 mm sections; the sections were washed extensively in distilled water, frozen on a liquid-helium cooled copper block, freeze-dried at −80° C., and coated with 2 nm of platinum at a 45° angle with rotation and 10 nm of carbon without rotation. Tissue was removed from the metal casting using bleach (Austin's A-1-5.25% sodium hypochlorite), washed and picked up on formvar-coated 200 mesh copper grids. Grids were photographed in a JEOL-1200 EX electron microscope at 100 kV.

FcγRIIa Blockade. FcγRIIa (CD32)-binding sites on human neutrophils were blocked by incubation for 15 minutes with the IV.3 antibody25 prior to TNF-α and anti-HNA-3a antibodytreatment. The IV.3 antibody was replaced by PBS (vehicle) for control treatment.

Statistical Analyses. Statistical significance for nonparametric distributions (mouse and human samples) was assessed with the two-tailed Mann-Whitney test for two groups. The one-way ANOVA test with Bonferroni post-test was used for in vitro studies (NET quantifications). GRAPHPAD PRISM™ 4.0 software was used for all analyses. Differences were considered statistically significant at P<0.05. In the figures, significant differences were illustrated with asterisks (* P<0.05;  P<0.01; * P<0.005.

Results

Anti-neutrophil Antibody Linked to TRALI Promotes NET Formation In Vitro

Figure 23C:
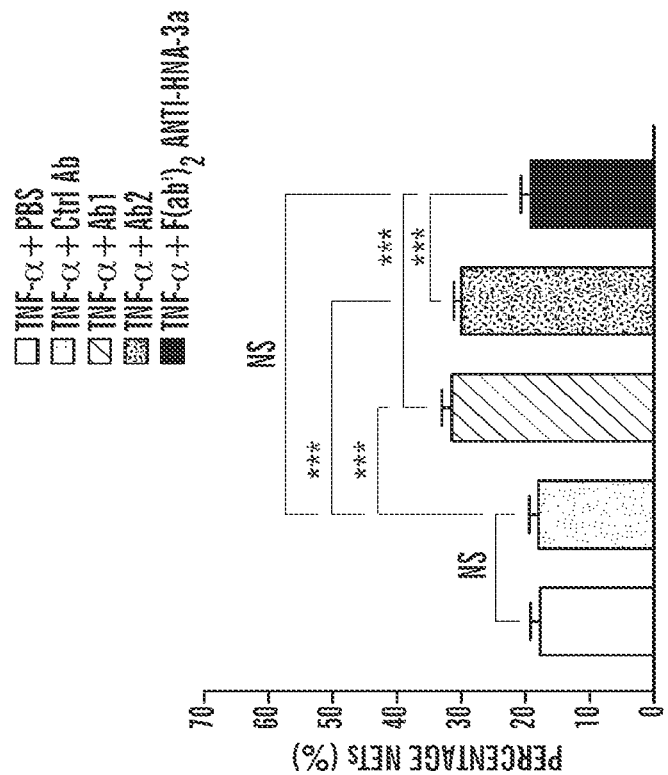
FIGS. 23A-23C demonstrate the effect of anti-HNA-3a antibody on NET formation by human neutrophils.
Figure 23A:
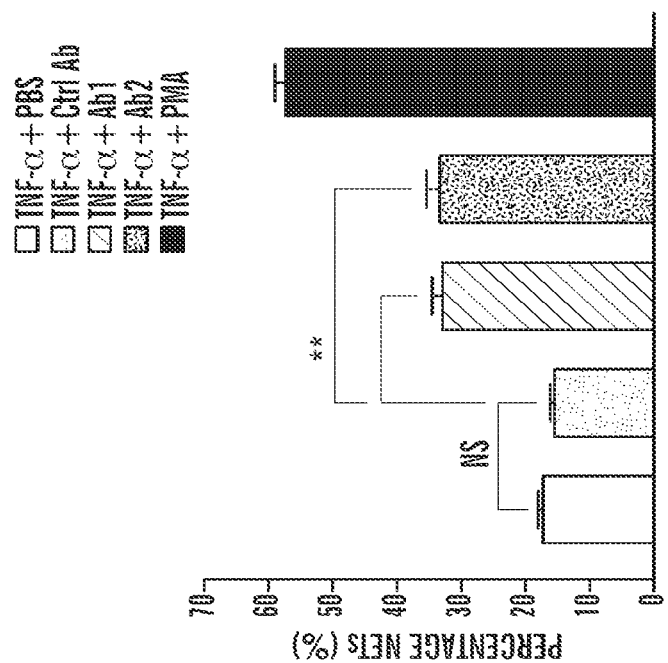
Figure 23B:
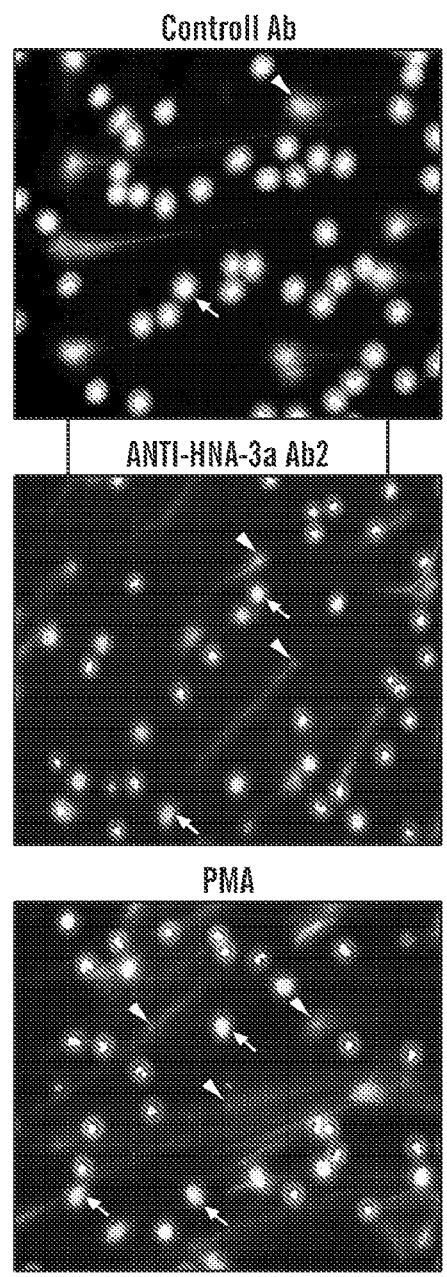

Because anti-HNA-3a antibodies cause the most severe TRALI,[3,18,19] whether such antibodies could promote NET formation by human neutrophils was tested. IgG were purified from two blood donors with anti-HNA-3a antibodies whose plasma caused a TRALI reaction in patients and control IgG were purified from a control donor's plasma. Neutrophils positive for the HNA-3a antigen were isolated from healthy volunteers' blood and primed with 5 ng/ml of tumor necrosis factor-α (TNF-α, a LPS-induced cytokine). The neutrophils were then incubated with 5 μg/ml of either anti-HNA-3a IgG or control IgG for 180 minutes and compared to the effect of phorbol 12-myristate 13-acetate (PMA) to quantify their capacity to induce NETs. Using fluorescence microscopy, it was observed that TNF-α-primed neutrophils formed significantly more NETs upon incubation with the two sources of anti-HNA-3a antibodies (Ab1 and Ab2) compared to neutrophils incubated with control IgG (FIGS. 23A and 23B). Moreover, a majority of the neutrophils treated with the anti-HNA-3a antibody lost their lobulated nucleus morphology. This delobulation was associated with a larger nucleus area (FIG. 23C), which is a typical early event in the formation of NETs.[23]

Figure 24:
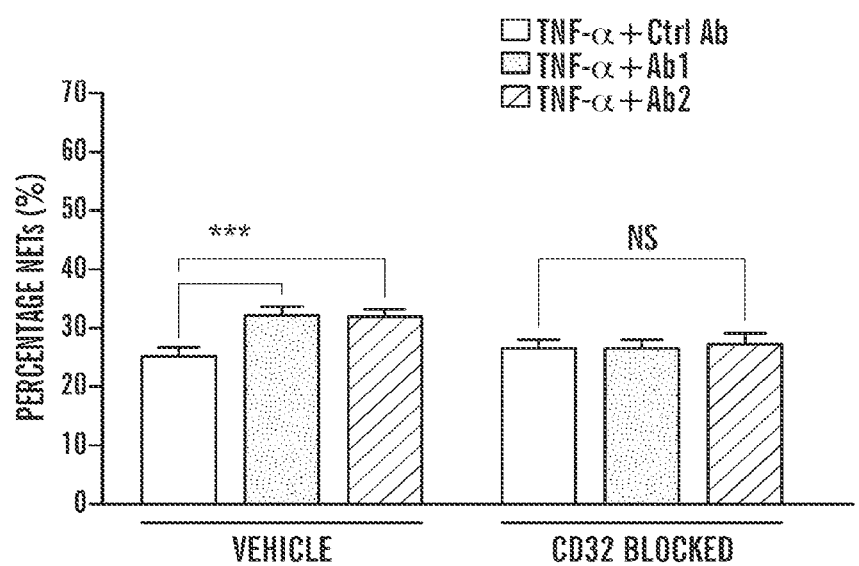
FIG. 24 depicts a graph demonstrating that inhibition of anti-HNA-3a antibody-induced NETs formation by FcγRIIa blockade. Isolated neutrophils were treated for 15 minutes with PBS or with a CD32 (FcγRIIa)-blocking antibody, primed with TNF-α and incubated for 180 minutes with control IgG purified from healthy volunteer blood (TNF-α+ Ctrl Ab) or with anti-HNA-3a antibodies purified from two blood donors whose blood/blood product induced TRALI (TNF-α+Ab1 and TNF-α+Ab2). DNA release was visualized after DNA staining with Hoechst 33342 and fixation. The experiment was independently performed 3 times. Bars represent means±s.e.m. An overall increase in background is observed. This is likely due to the additional incubation of neutrophils during PBS or anti-CD32 antibody pretreatment. *** $P<0.005$.
Figure 25A:
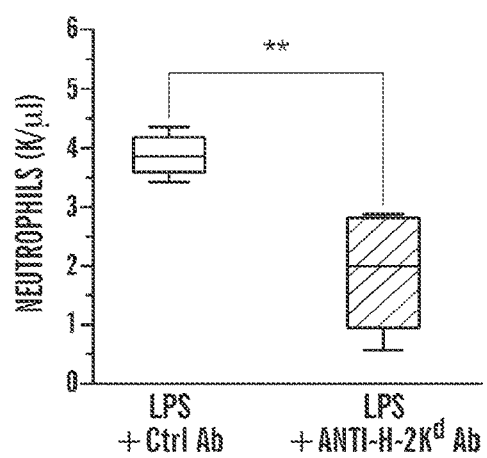
FIGS. 25A-25D depict graphs characterizing the TRALI model in BALB/c mice used in this study. (25A) Peripheral neutrophil and (25B) platelet counts, (25C) BAL proteins and (25D) lung tissue MPO content in mice administered i.p. with LPS (0.1 mg/kg) and i.v. with an isotype control or the anti-H-2Kd Ab (1.0 mg/kg, LPS group and TRALI group) represented by box plot. *$P<0.05$; **$P<0.01$.
Figure 25B:
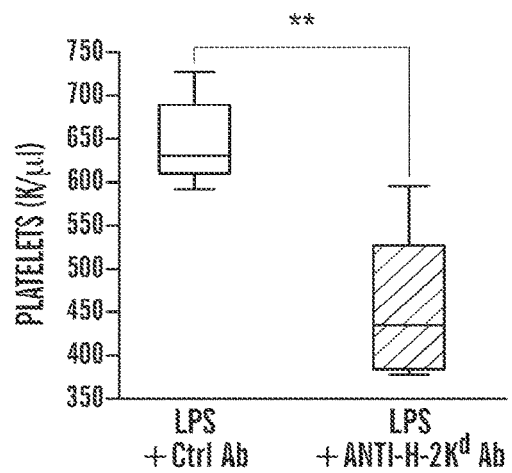
Figure 25C:
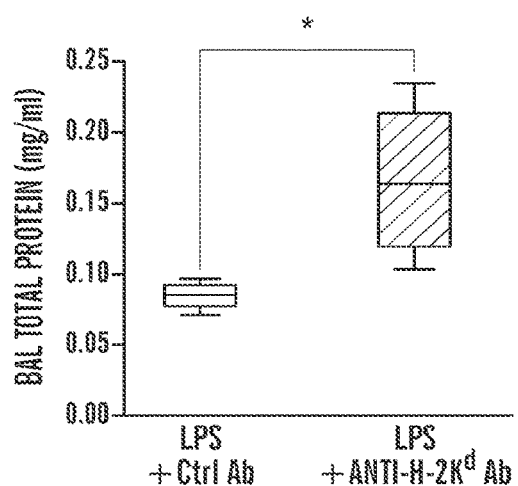
Figure 25D:
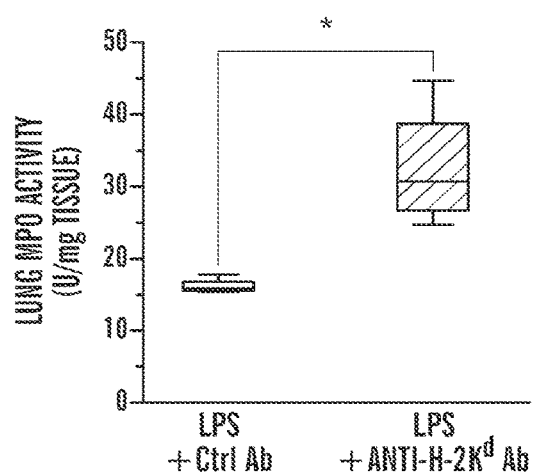

Because FcγR engagement has been shown to be linked to robust ROS generation,[24] and ROS generation promotes NET formation,[9] it was hypothesized that FcγR engagement by anti-neutrophil antibodies could promote NETosis. To test this hypothesis, F(ab')$_2$ fragments were prepared from anti-HNA-3a IgG purified from a blood donor whose plasma induced TRALI (Ab1). The incubation of anti-HNA-3a F(ab')$_2$ fragments with TNF-α-primed neutrophils did not induce NETs generation to a greater extent than TNF-α alone (FIG. 23C). As a second approach, the FcγRIIa (CD32)-binding sites on human neutrophils were blocked with the IV.3 antibody[25] prior to TNF-α and anti-HNA-3a antibody treatment. The increase in NETosis was no longer observed after anti-HNA-3a antibody (Ab1, Ab2) stimulation (FIG. 24). Together these results indicate that anti-HNA-3a antibodies trigger neutrophil activation, ultimately leading to NET generation likely through a FcγRIIa-dependent process.

NET Biomarkers can be Detected in the Bloodstream of Patients with TRALI

In order to determine whether NETs are formed in humans during TRALI, the presence of NET degradation products was assessed in the blood of patients with documented TRALI. For that purpose, serum samples from 6 healthy volunteers and from 5 patients who developed pulmonary insufficiency within 1-6 hours of transfusion and were diagnosed with TRALI (Table 2)[1] were blindly screened. A significant increase in circulating DNA and nucleosome levels was detected in the TRALI patients compared to the healthy subjects (Table 5). Based on the increase in concentration of these markers, samples that originated from TRALI patients versus control individuals were correctly identified. Blood donors that induced TRALI (Table 3) did not contain excessive DNA or nucleosomes when compared to healthy control subjects, indicating that NETs formed in the recipients after transfusion (Table 4). Even though the increase in circulating levels of DNA and nucleosomes cannot be exclusively attributed to NET formation, the tendency for serum myeloperoxidase to increase in TRALI patients likely reflects neutrophil activation.

Antibody-mediated TRALI Causes NET Formation in the Lungs of Mice

Figure 27A:
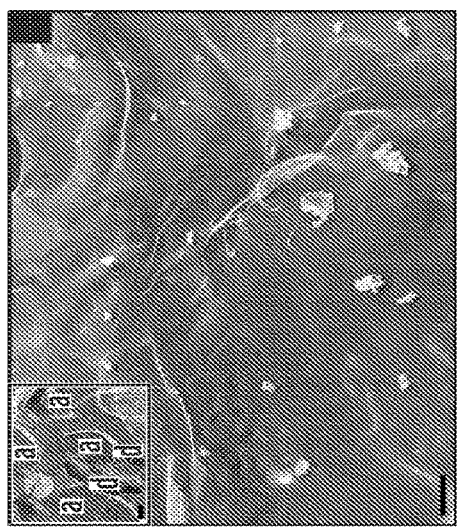
FIGS. 27A-27D depict electron micrographs demonstrating that a DNA-based fibrous mesh is present in the lungs of mice with TRALI. Representative photographs obtained by transmission electron microscopy of the lung epithelial surface of control mice (FIG. 27A), mice with TRALI (FIGS. 27B, 27D) and mice that were injected with LPS (0.5 mg/kg) and received DNase 1 prior to anti-H-2K$^d$ mAb injection (FIG. 27C). The fibrous material found in TRALI lungs is absent after DNase 1 treatment. Scale bar, 1 μm. The insets show low magnification views of the lung surface revealing alveolar sacs (a) and ducts (d); inset scale bars, 2 μm. The pictures are representative of three independent experiments.
Figure 27B:
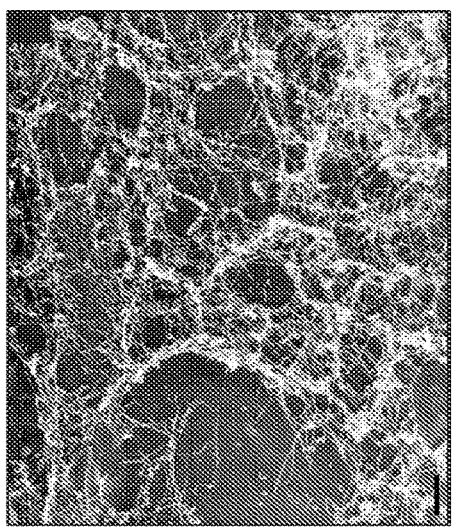
Figure 27C:
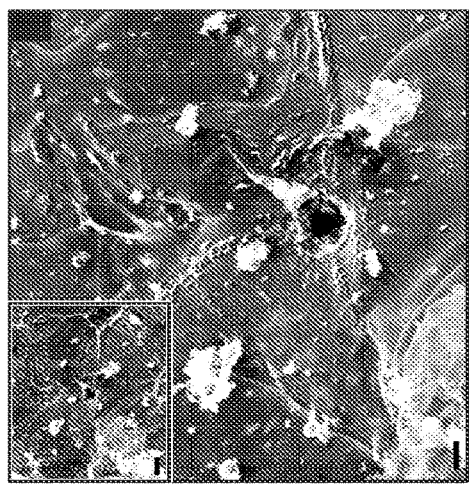
Figure 27D:
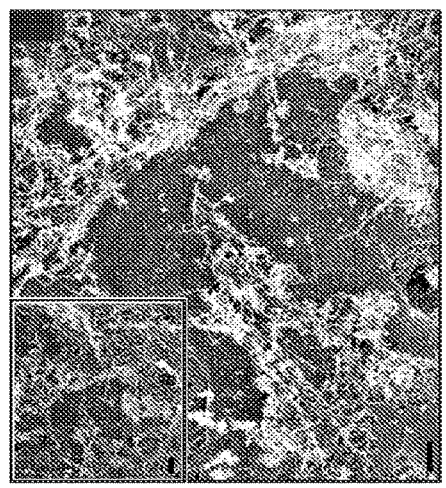

A previously established in vivo model of antibody-induced TRALI in mice was next used.[20,21,26] In this two-event model, BALB/c mice are injected i.p. with a low-dose of LPS (0.1-0.5 mg/kg) and 24 hours later are infused with an anti-MHC class I monoclonal antibody (anti-H-2K$^d$). Two hours later, arterial blood oxygen saturation was measured to document lung function. The mice were then sacrificed and lung injury markers[26] quantified (FIG. 25A-25D, data not shown). As observed in blood from TRALI patients, a significant increase (1.3 to 3.6 fold) in the concentration of NET biomarkers such as DNA, nucleosomes, and myeloperoxidase was detected in the plasma of mice with TRALI compared to mice that were challenged only with LPS (FIGS. 26A-26C). Besides endothelial cells, monocytes and platelets,[20,26,27] neutrophils are essential in the pathophysiology of TRALI.[3,26] Their recruitment to lung tissue combined with their activation induced by antibody transfusion[20] led to the hypothesis that NETs are formed in the lungs of mice during TRALI. Transmission electron microscopy (TEM) was used to address this question (FIGS. 27A-27D). This technique allowed the detection of a fibrous mesh coating the alveoli within the airspace in the TRALI group (FIGS. 27B and 27D), but such a mesh was not detected in control mice (FIG. 27A). Since fibrin and DNA cannot be distinguished by EM[28] and because DNase 1 cleaves DNA but not fibrin,[29] LPS-primed mice were treated with intranasal DNase 1 administration 10 minutes prior to antibody injection. Two hours after anti-H-2K$^d$ mAb challenge, no fibrous material could be detected in the DNase 1-treated alveoli (FIG. 27C); thus DNA was the basis of the fibrous mesh in the alveoli of mice with TRALI. These results are supported by widefield fluorescence microscopy observation of more DNA fibers with morphological NET characteristics in mice with TRALI, (data not shown) by visualization of diffuse DNA structures of irregular shape and DNA streaks next to alveoli. The fluorescence microscopy also showed that this DNA likely originated from neutrophils or a subset of monocytes (Gr-1 positive). Histone citrullination catalyzed by PAD4 (peptidylarginine deiminase 4), an enzyme prominently found in granulocytes[30] has been shown to be a crucial step for neutrophil chromatin decondensation and in NET formation.[8] Multiphoton analysis of fixed lung tissue allowed the observation of areas with robust citrullinated histone H3 staining colocalizing with DNA streaks in the alveoli outside blood vessels in mice with TRALI. Thus the extracellular DNA was most likely of neutrophil origin. In the model described herein, depletion of Gr-1 positive cells prevented the appearance of hypercitrullinated histone H3 formation in the lungs of the mice subjected to TRALI whereas platelet depletion did not preclude the presence of these NET biomarkers in the lungs (data not shown). The robust staining for citrullinated histone H3 observed in mice with TRALI was rarely present in LPS-only-treated mice and could not be detected by widefield fluorescence microscopy in control lungs (data not shown).

NET Disruption in Alveoli during TRALI can Improve Blood Oxygenation in Mice

Because intranasal DNase 1 treatment of the mice prior to anti-H-2K$^d$ mAb infusion can prevent NET deposition in the lungs, whether it could improve lung function in mice with TRALI was examined. Mice subjected to TRALI present transient hypoxia as shown by down spikes in blood arterial oxygenation saturation (saturation <90%) (data not shown), a phenomenon not observed in control healthy mice (data not shown). These down spikes were significantly attenuated in the mice pretreated with DNase 1 (data not shown) compared to the vehicle buffer-pretreated mice. A general effect of DNase 1 on blood oxygenation can be measured and is depicted as an increase of the mean arterial oxygen saturation recorded (overall oxygen saturation stability, FIG. 28A) accompanied by an increase in the minimum arterial oxygen saturation measured during the 20 minute-recording time (hypoxia episode intensity, FIG. 28B) when compared to healthy mice. These results showed that DNase 1 given i.n. as a pretreatment (Pre) but also given i.n. as a treatment 90 minutes after the onset of TRALI (Post) succeeded in correcting the defect in blood oxygenation observed during TRALI. Body temperatures were also monitored as a measure of the shock-like condition induced by the LPS/anti-H-2K$^d$ mAb infusion. While the mice with TRALI were showing signs of hypothermia 2 hours after mAb infusion (FIG. 28C), rectal temperatures were normal in mice subjected to TRALI and that received DNase 1 either as prophylaxis or treatment. These results support the hypothesis that NETs are indeed formed in TRALI lungs and are involved in the pathophysiology of TRALI.

Discussion

NETs are important in anti-bacterial defense,[6,7] but several studies have shown that NETs[31] and their components, such as histones,[12,32] elastase[11] or pentraxin-3[13] are injurious to tissues. Histones, at a high dose, can even induce death when infused intravenously in mice.[12,16] In addition, NETs activate blood coagulation[33] and platelets.[29,34] Histone infusion causes rapid thrombocytopenia in mice[34] and mild thrombocytopenia is one of the hallmarks of the mouse TRALI model[20] where it is shown herein that NETs are generated. Reduced platelet counts have been observed during TRALI in a retrospective study of patients developing TRALI compared to controls.[35] Activation of platelets can, in turn, promote additional neutrophil activation and more NET generation.[33,36] This has been observed in a sepsis model where LPS was shown to activate platelets through TLR4, promoting platelet-neutrophil complex formation and NET generation. Also, collagen-mediated platelet activation, such as would occur in trauma or major surgery, was linked to platelet-induced NET formation.[33] Interestingly, both infection and surgery are risk factors for developing TRALI.[2,37,38] It is proposed herein that NET formation and its injury to the lung is a common denominator of the different scenarios causing TRALI.

Indeed, platelets have been shown to contribute to the TRALI mouse model that described herein where LPS is given as a primer before antibody infusion. Looney and colleagues have shown that after LPS priming, antibody-induced TRALI could be prevented by platelet depletion.[20] A recent study using a model without LPS priming showed that platelets were not required for TRALI development.[27] Even if LPS-activated platelets may be involved in vascular cell activation and in NET formation, it was observed herein that platelet depletion with neuraminidase did not prevent NET formation in the lungs of mice with TRALI. However, this result does not exclude that the presence of platelets may further augment NET formation.

In most animal models, an antibody infusion is needed or is sufficient to induce TRALI. In both mouse models discussed above, Fcγ receptor (FcγR) activation was implicated in the TRALI process.[26,27] Silliman and colleagues have shown in an in vitro study that FcγR are not required in neutrophil-mediated damage of endothelial cells at early time points after anti-HNA-3a antibody incubation'. However, it may not be the case at later time points where FcγR-binding may lead to NET formation in the lungs during TRALI. The question of whether FcγR are involved or not in mouse TRALI was first asked by Looney and colleagues.[26] They have shown that FcγR−/− mice were protected from TRALI following anti-H-2K$^d$ antibody challenge and observed that the injection of wild-type neutrophils into FcγR−/− mice restored ALI (acute lung injury) following mAb delivery. Strait and collaborators recently reported that FcγR were playing a role in TRALI but that they were not responsible for all the lung injury and that macrophages and complement activation were also involved.[27]

It is demonstrated herein that human TRALI-inducing antibodies stimulated NET generation from primed human neutrophils and this required the Fc portion of the antibody. Just crosslinking of the neutrophil antigen/receptor HNA-3a/CLT-2 was not sufficient to activate NET formation since it was observed herein that anti-HNA-3a F(ab')$_2$ fragment-treatment on TNF-α-primed neutrophils did not induce NET generation. Thus NET initiation by the antibody likely also implicates a FcγR binding-dependent mechanism. Furthermore, when TNF-α-primed human neutrophils were treated with another antibody that binds neutrophils, more NETs were observed when compared to treatment with an isotype control antibody (data not shown). Thus, described herein is a specific mechanism ultimately leading to NET formation in antibody-mediated TRALI through FcγR activation. The data described herein are consistent with studies describing NET production in autoimmune diseases such as small-vessel vasculitis[14] or systemic lupus erythematous,[15,39] where FcγR can be activated.[24,40,41]

However, NETs may be formed in non antibody-mediated TRALI as well. No antibodies could be detected in the transfused units to 2 of the 5 TRALI patients examined in this study and yet NET biomarkers were generated and could be detected in their circulation. In 1997, Silliman and colleagues proposed that biologically active lipids released during blood storage could activate neutrophils and cause TRALI.[37,42] Other groups have also reported effects of components present and accumulating in the supernatant of stored platelets on neutrophil activation both in vitro and in animal models.[2,22,43-45] A recent study showed that longer platelet storage was associated with an increased risk of TRALI in patients.[46] One such biologically active lipid that could be formed during platelet storage, platelet-activating factor, is a good inducer of NET formation in vitro[29] and other biologically active lipids could be as well. Similarly, NETs can form in ALI[32,47] in which released cytokines or bacterial presence have already been described as strong NET inducers.[6,13,48] Thus it is possible that a variety of stimulants implicated in TRALI may alone or in combination with another "hit" induce NET formation.

Lungs may be the most susceptible organ for NET deposition after transfusion, as clumped activated neutrophils would likely be trapped in lung microcirculation and transmigrate locally while forming NETs. However, the degradation products of NETs were found systemically in blood of both patients and mice with TRALI. These are likely generated by DNase 1 which is present in plasma of mice and humans and whose function is to degrade DNA released from dying cells.[49] Indeed, there is no certainty that the increase in NET biomarkers measured in human blood from TRALI patients is due only to the TRALI reaction. That is why additional data were provided in order to show that NETs are formed in vitro by neutrophils in response to the HNA-3a anti-neutrophil antibody challenge, and in vivo in the lungs and plasma of originally healthy mice suffering from TRALI. As described above herein, supplementing mice i.v. with DNase 1 prevented NET-initiated thrombosis in a mouse model of deep vein thrombosis[50] and reduced brain injury in a mouse model of stroke.[51] In this mouse TRALI model, NETs were revealed in the lung tissue by their irregular patterns when stained for both DNA and citrullinated histones, a hallmark of NET generation and their DNA bases confirmed by DNase 1 susceptibility. NETs were found in abundance in the TRALI-affected alveoli with only a few detectable in the pulmonary microcirculation. Without wishing to be bound by theory, either they are more protected there from plasma DNase 1 digestion and therefore are easily detected or they preferentially form at this location. Monocytes/macrophages were also shown to be important in the development of mouse TRALI.[27] These cells, in the alveoli, together with lung epithelial cells, generate lung inflammatory mediators such as interleukin-1β and TNF-α,[52] both important NET inducers.[14,17] These two cytokines could provide a strong local stimulus to the neutrophils primed in the vessels by antibodies or bioactive lipids for NET production at this location.

Figure 28A:
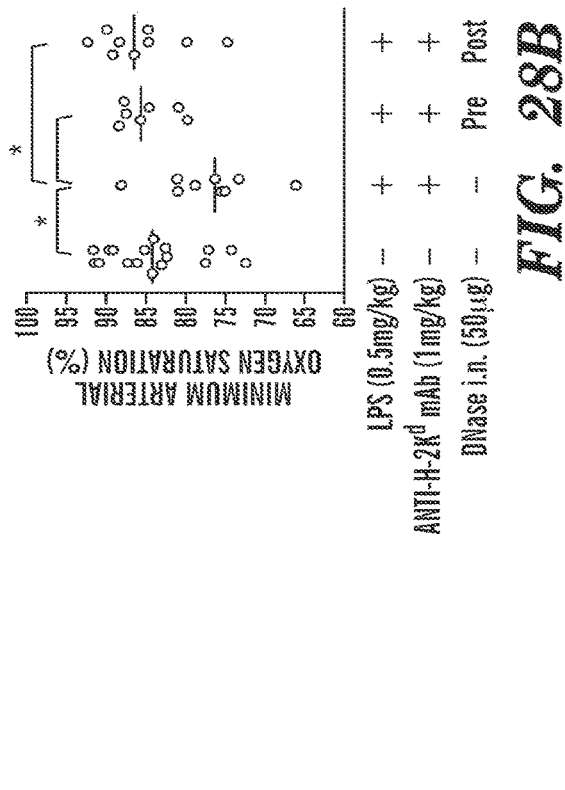
FIGS. 28A-28C depict graphs demonstrating that DNase 1 treatment improves blood oxygenation of mice with TRALI. The mice received i.n. vehicle-buffer or i.n. DNase 1 10 minutes prior to anti-H-2K$^d$ antibody injection. Mice that received DNase 1 showed more stable arterial blood oxygen saturation and improved transient hypoxia when compared to the mice pretreated with the vehicle-buffer.
Figure 28B:
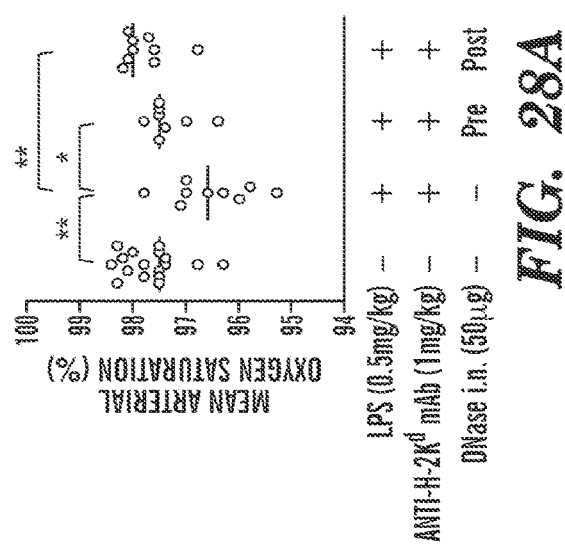
Figure 28C:
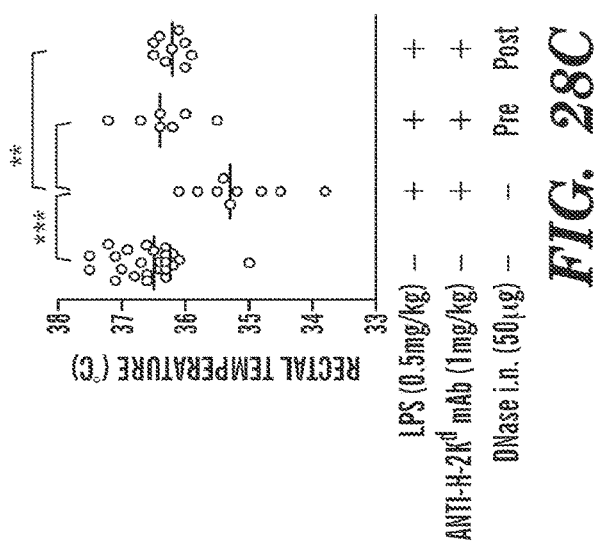

Importantly, as described herein, NET deposition in mouse lungs could be interrupted by DNase 1 inhalation. This treatment not only prevented NET accumulation in the alveoli but also appeared to improve the lung function of the mice experiencing TRALI. Indeed, it seems to be in the alveoli that NETs produced the most preventable damage in TRALI. In experiments described herein, i.v. DNase 1 administration did not improve TRALI outcome, whereas the inhalation of DNase 1 that brought the drug directly to the alveoli had a positive effect both when administered before or after TRALI onset (FIG. 28A-28C). These results are exciting and show that DNase 1 can be used not only as a prophylactic agent but also as a treatment for TRALI after it started.

To conclude, the data described herein document that NETs form during TRALI both in humans and in mice and that NET degradation, as shown experimentally by DNase 1 inhalation, can improve the condition of mice with TRALI. Thus a new mechanistic facet in the understanding of the pathogenesis of TRALI is provided and NETs are identified as a target for TRALI therapy. DNase 1, the drug we herein, is FDA-approved (PULMOZYME®) to treat the lungs of cystic fibrosis patients. These patients were recently shown to produce NETs markers, [53] which were found in their sputum. It is proposed herein that TRALI-associated NET formation can be arrested by preventing neutrophil chromatin decondensation with neutrophil elastase inhibitors[54] or with inhibitors to the histone-citrullinating enzyme peptidylarginine deiminase (PAD4).[8,55] NET inhibitors can be used to treat TRALI and/or as prophylaxis for patients at high risk of developing TRALI.

References for Example 9
1. Kleinman S, Caulfield T, Chan P, et al. Toward an understanding of transfusion-related acute lung injury: statement of a consensus panel. *Transfusion.* 2004; 44(12):1774-1789.
2. Vlaar AP, Hofstra JJ, Determann RM, et al. The incidence, risk factors, and outcome of transfusion-related acute lung injury in a cohort of cardiac surgery patients: a prospective nested case-control study. *Blood.* 2011; 117(16): 4218-4225.
3. Davoren A, Curtis BR, Shulman IA, et al. TRALI due to granulocyte-agglutinating human neutrophil antigen-3a (5b) alloantibodies in donor plasma: a report of 2 fatalities. *Transfusion.* 2003; 43(5):641-645.
4. Hashimoto S, Nakajima F, Kamada H, et al. Relationship of donor HLA antibody strength to the development of transfusion-related acute lung injury. *Transfusion.* 2010; 50(12):2582-2591.
5. Silliman CC, Curtis BR, Kopko PM, et al. Donor antibodies to HNA-3a implicated in TRALI reactions prime neutrophils and cause PMN-mediated damage to human pulmonary microvascular endothelial cells in a two-event in vitro model. *Blood.* 2007; 109(4):1752-1755.
6. Brinkmann V, Reichard U, Goosmann C, et al. Neutrophil extracellular traps kill bacteria. *Science.* 2004; 303(5663): 1532-1535.
7. Urban CF, Ermert D, Schmid M, et al. Neutrophil extracellular traps contain calprotectin, a cytosolic protein complex involved in host defense against *Candida albicans. PLoS Pathog.* 2009; 5(10):e1000639.
8. Wang Y, Li M, Stadler S, et al. Histone hypercitrullination mediates chromatin decondensation and neutrophil extracellular trap formation. *J Cell Biol.* 2009; 184(2):205-213.
9. Fuchs TA, Abed U, Goosmann C, et al. Novel cell death program leads to neutrophil extracellular traps. *J Cell Biol.* 2007; 176(2): 231-241.
10. Buchanan JT, Simpson AJ, Aziz RK, et al. DNase expression allows the pathogen group A *Streptococcus* to escape killing in neutrophil extracellular traps. *Curr Biol.* 2006; 16(4):396-400.
11. Bless NM, Smith D, Charlton J, et al. Protective effects of an aptamer inhibitor of neutrophil elastase in lung inflammatory injury. *Curr Biol.* 1997; 7(11):877-880.
12. Xu J, Zhang X, Pelayo R, et al. Extracellular histones are major mediators of death in sepsis. *Nat Med.* 2009; 15(11):1318-1321.
13. Savchenko AS, Inoue A, Ohashi R, et al. Long pentraxin 3 (PTX3) expression and release by neutrophils in vitro and in ulcerative colitis. *Pathol Int.* 2011; 61(5):290-297.
14. Kessenbrock K, Krumbholz M, Schonermarck U, et al. Netting neutrophils in autoimmune small-vessel vasculitis. *Nat Med.* 2009; 15(6): 623-625.

15. Garcia-Romo GS, Caielli S, Vega B, et al. Netting neutrophils are major inducers of type I IFN production in pediatric systemic lupus erythematosus. *Sci Transl Med.* 2011; 3(73):73ra20.
16. Xu J, Zhang X, Monestier M, Esmon NL, Esmon CT. Extracellular histones are mediators of death through TLR2 and TLR4 in mouse fatal liver injury. *J Immunol.* 2011; 187(5):2626-2631.
17. Mitroulis I, Kambas K, Chrysanthopoulou A, et al. Neutrophil extracellular trap formation is associated with IL-1beta and autophagy-related signaling in gout. *PloS One.* 2011; 6(12):e29318.
18. Curtis BR, Cox NJ, Sullivan MJ, et al. The neutrophil alloantigen HNA-3a (5b) is located on choline transporter-like protein 2 and appears to be encoded by an R>Q154 amino acid substitution. *Blood.* 2010; 115(10): 2073-2076.
19. Greinacher A, Wesche J, Hammer E, et al. Characterization of the human neutrophil alloantigen-3a. *Nat Med.* 2010; 16(1): 45-48.
20. Looney MR, Nguyen JX, Hu Y, Van Ziffle JA, Lowell CA, Matthay MA. Platelet depletion and aspirin treatment protect mice in a two-event model of transfusion-related acute lung injury. *J Clin Invest.* 2009; 119(11): 3450-3461.
21. Hidalgo A, Chang J, Jang JE, Peired AJ, Chiang EY, Frenette PS. Heterotypic interactions enabled by polarized neutrophil microdomains mediate thromboinflammatory injury. *Nat Med.* 2009; 15(4):384-391.
22. Looney MR, Matthay MA. Animal models of transfusion-related acute lung injury. *Crit Care Med.* 2006; 34(5 Suppl):5132-136.
23. Hakkim A, Fuchs TA, Martinez NE, et al. Activation of the Raf-MEK-ERK pathway is required for neutrophil extracellular trap formation. *Nat Chem Biol.* 2011; 7(2): 75-77.
24. Tsuboi N, Asano K, Lauterbach M, Mayadas TN. Human neutrophil Fcgamma receptors initiate and play specialized nonredundant roles in antibody-mediated inflammatory diseases. *Immunity.* 2008; 28(6):833-846.
25. Xiao Z, Visentin GP, Dayananda KM, Neelamegham S. Immune complexes formed following the binding of anti-platelet factor 4 (CXCL4) antibodies to CXCL4 stimulate human neutrophil activation and cell adhesion. *Blood.* 2008; 112(4):1091-1100.
26. Looney MR, Su X, Van Ziffle JA, Lowell CA, Matthay MA. Neutrophils and their Fc gamma receptors are essential in a mouse model of transfusion-related acute lung injury. *J Clin Invest.* 2006; 116(6):1615-1623.
27. Strait RT, Hicks W, Barasa N, et al. MHC class I-specific antibody binding to nonhematopoietic cells drives complement activation to induce transfusion-related acute lung injury in mice. *J Exp Med.* 2011; 208(12):2525-2544.
28. Krautgartner WD, Klappacher M, Hannig M, et al. Fibrin mimics neutrophil extracellular traps in SEM. *Ultrastruct Pathol.* 2010; 34(4):226-231.
29. Fuchs TA, Brill A, Duerschmied D, et al. Extracellular DNA traps promote thrombosis. *Proc Natl Acad Sci USA.* 2010; 107(36): 15880-15885.
30. Asaga H, Nakashima K, Senshu T, Ishigami A, Yamada M. Immunocytochemical localization of peptidylarginine deiminase in human eosinophils and neutrophils. *J Leukoc Biol.* 2001; 70(1):46-51.
31. Gupta AK, Joshi MB, Philippova M, et al. Activated endothelial cells induce neutrophil extracellular traps and are susceptible to NETosis-mediated cell death. *FEBS Lett.* 2010; 584(14):3193-3197.
32. Saffarzadeh M, Juenemann C, Queisser MA, et al. Neutrophil extracellular traps directly induce epithelial and endothelial cell death: a predominant role of histones. *PloS One.* 2012; 7(2):e32366.
33. Massberg S, Grahl L, von Bruehl ML, et al. Reciprocal coupling of coagulation and innate immunity via neutrophil serine proteases. *Nat Med.* 2010; 16(8):887-896.
34. Fuchs TA, Bhandari AA, Wagner DD. Histones induce rapid and profound thrombocytopenia in mice. *Blood.* 2011; 118(13):3708-3714.
35. Vlaar AP, Binnekade JM, Prins D, et al. Risk factors and outcome of transfusion-related acute lung injury in the critically ill: a nested case-control study. *Crit Care Med.* 2010; 38(3):771-778.
36. Clark SR, Ma AC, Tavener SA, et al. Platelet TLR4 activates neutrophil extracellular traps to ensnare bacteria in septic blood. *Nat Med.* 2007; 13(4):463-469.
37. Silliman CC, Boshkov LK, Mehdizadehkashi Z, et al. Transfusion-related acute lung injury: epidemiology and a prospective analysis of etiologic factors. *Blood.* 2003; 101(2):454-462.
38. Gajic O, Rana R, Winters JL, et al. Transfusion-related acute lung injury in the critically ill: prospective nested case-control study. *Am J Respir Crit Care Med.* 2007; 176(9):886-891.
39. Hakkim A, Furnrohr BG, Amann K, et al. Impairment of neutrophil extracellular trap degradation is associated with lupus nephritis. *Proc Natl Acad Sci USA.* 2010; 107(21):9813-9818.
40. Tan Sardjono C, Mottram PL, van de Velde NC, et al. Development of spontaneous multisystem autoimmune disease and hypersensitivity to antibody-induced inflammation in Fcgamma receptor IIa-transgenic mice. *Arthritis Rheum.* 2005; 52(10):3220-3229.
41. Tsuboi N, Ernandez T, Li X, et al. Regulation of human neutrophil Fcgamma receptor IIa by C5a receptor promotes inflammatory arthritis in mice. *Arthritis Rheum.* 2011; 63(2):467-478.
42. Silliman CC, Fung YL, Ball JB, Khan SY. Transfusion-related acute lung injury (TRALI): current concepts and misconceptions. *Blood Rev.* 2009; 23(6):245-255.
43. Wyman TH, Bjornsen AJ, Elzi DJ, et al. A two-insult in vitro model of PMN-mediated pulmonary endothelial damage: requirements for adherence and chemokine release. *Am J Physiol Cell Physiol.* 2002; 283(6):C1592-1603.
44. Khan SY, Kelher MR, Heal JM, et al. Soluble CD40 ligand accumulates in stored blood components, primes neutrophils through CD40, and is a potential cofactor in the development of transfusion-related acute lung injury. *Blood.* 2006; 108(7):2455-2462.
45. Vlaar AP, Hofstra JJ, Kulik W, et al. Supernatant of stored platelets causes lung inflammation and coagulopathy in a novel in vivo transfusion model. *Blood.* 2010; 116(8):1360-1368.
46. Middelburg RA, Borkent B, Jansen M, et al. Storage time of blood products and transfusion-related acute lung injury. *Transfusion.* 2011.
47. Narasaraju T, Yang E, Samy RP, et al. Excessive neutrophils and neutrophil extracellular traps contribute to acute lung injury of influenza pneumonitis. *Am J Pathol.* 2011; 179(1):199-210.
48. Gupta AK, Hasler P, Holzgreve W, Gebhardt S, Hahn S. Induction of neutrophil extracellular DNA lattices by placental microparticles and IL-8 and their presence in preeclampsia. *Hum Immunol.* 2005; 66(11):1146-1154.
49. Napirei M, Gultekin A, Kloeckl T, Moroy T, Frostegard J, Mannherz HG. Systemic lupus-erythematosus: deoxyribonuclease 1 in necrotic chromatin disposal. *Int J Biochem Cell Biol.* 2006; 38(3):297-306.
50. Brill A, Fuchs TA, Savchenko AS, et al. Neutrophil extracellular traps promote deep vein thrombosis in mice. *J Thromb Haemost.* 2012; 10(1): 136-144.
51. De Meyer SF, Fuchs TA, Suidan GL, et al. Extracellular chromatin is an important mediator of ischemic stroke. Paper presented at International Society on Thrombosis and Haemostasis. Jul. 25, 2011. Kyoto, Japan. 2011.
52. Skerrett SJ, Liggitt HD, Hajjar AM, Ernst RK, Miller SI, Wilson CB. Respiratory epithelial cells regulate lung inflammation in response to inhaled endotoxin. *Am J Physiol Lung Cell Mol Physiol.* 2004; 287(1):L143-152.
53. Papayannopoulos V, Staab D, Zychlinsky A. Neutrophil elastase enhances sputum solubilization in cystic fibrosis patients receiving DNase therapy. *PloS One.* 2011; 6(12): e28526.
54. Papayannopoulos V, Metzler KD, Hakkim A, Zychlinsky A. Neutrophil elastase and myeloperoxidase regulate the formation of neutrophil extracellular traps. *J Cell Biol.* 2010; 191(3):677-691.
55. Li P, Li M, Lindberg MR, Kennett MJ, Xiong N, Wang Y. PAD4 is essential for antibacterial innate immunity mediated by neutrophil extracellular traps. *J Exp Med.* 2010; 207(9):1853-1862.

TABLE 2

Description of TRALI patients. These patients' samples were analyzed for NET biomarkers as shown in Table 5.

| TRALI patient # | Age/ gender | Patient leukocyte Abs | Donor Abs | Clinical Findings |
|---|---|---|---|---|
| 1 | 45/F | HLA class I 94% PRA HLA class II 100% PRA Neutrophil Abs of unknown specificity. | Not tested | Developed chest pain, increased hypotension and SOB 2 h 15 after transfusion with 2 units of PRBCs. Dense pulmonary infiltrates on chest x-ray. Sample was collected 2 h 30 after transfusion. |
| 2 | 7/F | HLA Class I 25% PRA Neutrophil Abs of unknown specificity. | Non-specific HLA class I Abs | Developed lip swelling, wheezing, apnea, hypoxia and hypotension 1 h 15 after transfusion with single donor platelets. Bilateral decreased lung volume, increased opacity in right upper lobe suggestive of atelectasis and consolidation on chest x-ray. Sample was collected 48 h after transfusion. |
| 3 | 89/F | HLA Class I positive | ND | Given 2 units of PRBCs 3 days after open-heart surgery. Developed severe SOB about 3 hours after second unit and was intubated and given $O_2$. Striking bilateral pulmonary infiltrates on chest x-ray. Time of sample collection is uncertain. |
| 4 | 80/F | HLA Class I positive HLA Class II positive | ND | Acute SOB and arterial $O_2$ at 83% 1 hour after receiving 2 units of platelets. Bilateral pulmonary edema on chest x-ray. Time of sample collection is uncertain. |
| 5 | 88/M | ND | Donor 1 was male, never transfused. Donor 2 was multiparous female (4 pregnancies) with class I and II HLA Abs. | Developed acute SOB and arterial $O_2$ at 35% 5 h 30 after transfusion of 2 units of PRBCs. Increased opacities and small pulmonary effusion on chest x-ray. Sample was collected 15 h after transfusion. |

PRA: panel reactive antibody (% of lymphocyte panel reactive with serum);
ND: None detected;
SOB: Shortness of breath;
PRBC: packed red blood cells.

TABLE 3

Description of blood donors that induced TRALI reactions associated with anti-HNA-3a antibodies. These donors' blood was analyzed in the granulocyte agglutination test and for NET biomarkers in Table 4. INR: international normalized ratio (standardized prothrombin time).

| Donor number # | Age | Gender | Number of Pregnancies | HLA Ab | Neutrophil Ab | Recipient Clinical Findings |
|---|---|---|---|---|---|---|
| 1 | 50 | Female | 3 | Yes | HNA-3a | A 79-year old male received plasma, including from donor #1, to correct INR before surgical repair of pseudoaneurysm. Within 6 hours, |

TABLE 3-continued

Description of blood donors that induced TRALI reactions associated with anti-HNA-3a antibodies. These donors' blood was analyzed in the granulocyte agglutination test and for NET biomarkers in Table 4. INR: international normalized ratio (standardized prothrombin time).

| Donor number # | Age | Gender | Number of Pregnancies | HLA Ab | Neutrophil Ab | Recipient Clinical Findings |
|---|---|---|---|---|---|---|
| | | | | | | developed acute respiratory distress, hypoxia, and bilateral pulmonary edema found on chest x-ray. |
| 2 | 51 | Female | 3 | No | HNA-3a | A 67-year old female received 19 blood products, including plasma from donor #2, during surgery to replace mitral and atrial heart valves. Recipient developed severe dyspnea and hypoxia, within 6 hours of blood transfusion. Chest x-ray showed pulmonary edema and bilateral lung infiltrates and frothy sputum was aspirated from lungs. Recipient died as a result of the TRALI reaction. |
| 3 | 65 | Female | 4 | No | HNA-3a | Plasma from donor #3 transfused to male recipient with biliary obstruction. Recipient developed chills, rigors, and hypoxia within 6 h. Chest x-ray showed pulmonary edema. |

TABLE 4

Absence of evidence of circulating NET biomarkers in blood donors and control individuals. Granulocyte agglutination test (GAT) and NET biomarker analysis in plasma samples from blood donors that induced TRALI reactions and from control donors. The degree of agglutination was graded from − (weak) to 3+ (strong). P = 0.9148, 0.7461 and 0.4921 when respectively DNA, MPO and nucleosome levels are compared in plasma from blood donors that induced TRALI with control individual plasma. Analyses were performed blinded to sample origin. MPO: myeloperoxidase.

| Sample # Specificity | GAT | DNA (ng/ml) | MPO (mU/ml) | Nucleosomes (OD 405-490) |
|---|---|---|---|---|
| Blood donor with anti-NB1 1 | +/− | 196 | 6.9 | 0 |
| Blood donor with anti-HNA-3a 1 | 3+ | 179 | 9.9 | 0.04 |
| Blood donor with anti-HNA-3a 2 | 2+ | 136 | 0 | 0 |
| Blood donor with anti-HNA-3a 3 | 2+ | 255 | 7.1 | 0 |
| Group median | | 188 | 7 | 0 |
| Control donor 1 | − | 296 | 0 | 0 |
| Control donor 2 | +/− | 203 | 6.3 | 0 |
| Control donor 3 | − | 166 | 1.4 | 0.02 |
| Control donor 4 | − | 173 | 106.9 | 0.04 |
| Control donor 5 | − | 160 | 8.6 | 0.03 |
| Control donor 6 | − | 160 | 0 | 0.03 |
| Group median | | 170 | 4 | 0 |
| P value | | 0.9148 | 0.7461 | 0.4921 |

TABLE 5

Evidence of circulating NET biomarkers in serum of patients with TRALI. Granulocyte agglutination test (GAT) and NET biomarker analysis in serum samples from TRALI patients and control healthy subjects. The degree of agglutination was graded from − (weak) to 3+ (strong). P = 0.0087, 0.1255 and 0.0043 when respectively DNA, MPO and nucleosome levels are compared in serum from patients with TRALI to control serums. Analysis was performed blinded to sample origin. All the TRALI patients' samples were higher than all control samples for at least one biomarker. MPO: myeloperoxidase.

| Sample # Specificity | GAT | DNA (ng/ml) | MPO (mU/ml) | Nucleosomes (OD 405-490) |
|---|---|---|---|---|
| TRALI patient 1 | +/− | 479 | 360.7 | 0.11 |
| TRALI patient 2 | +/− | 473 | 270.8 | 0.40 |
| TRALI patient 3 | +/− | 270 | 112.4 | 0.20 |
| TRALI patient 4 | +/− | 523 | 466.5 | 0.50 |
| TRALI patient 5 | +/− | 522 | 55.5 | 0.11 |
| Group median | | 479 | 270.8 | 0.20 |
| Normal control 1 | − | 266 | 39.7 | 0 |
| Normal control 2 | − | 294 | 79.6 | 0.01 |
| Normal control 3 | − | 250 | 45.9 | 0.06 |
| Normal control 4 | − | 221 | 243 | 0.10 |
| Normal control 5 | − | 241 | 87.4 | 0.07 |
| Normal control 6 | − | 235 | 138.9 | 0.05 |
| Group median | | 245 | 83.5 | 0.06 |
| P value | | 0.0087 | 0.1255 | 0.0043 |

```
Sequence Listing

SEQ ID NO: 1 PAD4 mRNA NCBI Ref Seq: NM_012387
    1 acagccagag ggacgagcta gcccgacgat ggcccagggg acattgatcc gtgtgacccc
   61 agagcagccc acccatgccg tgtgtgtgct gggcaccttg actcagcttg acatctgcag
  121 ctctgccctt gaggactgca cgtccttcag catcaacgcc tccccagggg tggtcgtgga
  181 tattgcccac ggccctccag ccaagaagaa atccacaggt tcctccacat ggccccctgga
  241 ccctggggta gaggtgaccc tgacgatgaa agtggccagt ggtagcacag gcgaccagaa
  301 ggttcagatt tcatactacg gacccaagac tccaccagtc aaagctctac tctacctcac
```

```
    361 cggggtggaa atctccttgt gcgcagacat caccgcacc  ggcaaagtga agccaaccag
    421 agctgtgaaa gatcagagga cctggacctg gggcccttgt  ggacagggtg ccatcctgct
    481 ggtgaactgt gacagagaca atctcgaatc ttctgccatg  gactgcgagg atgatgaagt
    541 gcttgacagc gaagacctgc aggacatgtc gctgatgacc  ctgagcacga agacccccaa
    601 ggacttcttc acaaaccata cactggtgct ccacgtggcc  aggtctgaga tggacaaagt
    661 gagggtgttt caggccacac ggggcaaact gtcctccaag  tgcagcgtag tcttgggtcc
    721 caagtggccc tctcactacc tgatggtccc cggtggaaag  cacaacatgg acttctacgt
    781 ggaggccctc gctttcccgg acaccgactt cccgggggctc  attaccctca ccatctccct
    841 gctggacacg tccaacctgg agctcccega ggctgtggtg  ttccaagaca gcgtggtctt
    901 ccgcgtggcg ccctggatca tgaccccaa  cacccagccc  ccgcaggagg tgtacgcgtg
    961 cagtatttt  gaaaatgagg acttcctgaa gtcagtgact  actctggcca tgaaagccaa
   1021 gtgcaagctg accatctgcc ctgaggagga aacatggat  gaccagtgga tgcaggatga
   1081 aatggagatc ggctacatcc aagccccaca caaaacgctg  cccgtggtct tcgactctcc
   1141 aaggaacaga ggcctgaagg agtttcccat caaacgcgtg  atgggtccag attttggcta
   1201 tgtaactcga gggccccaaa caggggtat  cagtggactg  gactcctttg ggaacctgga
   1261 agtgagcccc ccagtcacag tcaggggcaa ggaatacccg  ctgggcagga ttctcttcgg
   1321 ggacagctgt tatcccagca atgacagccg gcagatgcac  caggccctgc aggacttcct
   1381 cagtgcccag caggtgcagg cccctgtgaa gctctattct  gactggctgt ccgtgggcca
   1441 cgtggacgag ttcctgagct tgtgccagc  acccgacagg  aagggcttcc ggctgctcct
   1501 ggccagcccc aggtcctgct acaaactgtt  ccaggacgag  cagaatgagg gccacgggga
   1561 ggccctgctg ttcgaaggga tcaagaaaaa  aaaacagcag  aaaataaaga acattctgtc
   1621 aaacaagaca ttgagagaac ataattcatt  tgtggagaga  tgcatcgact ggaaccgcga
   1681 gctgctgaag cggagctgg  gcctggccga  gagtgacatc  attgacatcc gcagctctct
   1741 caagctcaaa gagttctcta aggcggaagc  tttttccce  aacatggtga acatgctggt
   1801 gctagggaag cacctgggca tccccaagcc  cttcgggccc  gtcatcaacg gccgctgctg
   1861 cctggaggag aaggtgtgtt ccctgctgga  gccactgggc  ctccagtgca ccttcatcaa
   1921 cgacttcttc acctaccaca tcaggcatgg  ggaggtgcac  tgcggcacca acgtgcgcag
   1981 aaagcccttc tccttcaagt ggtggaacat  ggtgccctga  gcccatcctc cctggcgtcc
   2041 tctccctcct ggccagatgt cgctgggtcc  tctgcagtgt  ggcaagcaag agctcttgtg
   2101 aatattgtgg ctccctgggg gcggccagcc  ctcccagcag  tggcttgctt tcttctcctg
   2161 tgatgtccca gtttcccact ctgaagatcc  aacatggtc  ctagcactgc acactcagtt
   2221 ctgctctaag aagctgcaat aaagttttt  taagtcactt  tgtac SEQ ID NO: 2 PAD4 amino acid sequence NCBI Ref Seq: NP_036519
      1 maqgtlirvt peqpthavcv lgtltqldic ssapedctsf sinaspgvvv diahgppakk
     61 kstgsstwpl dpgvevtltm kvasgstgdq kvqisyygpk tppvkallyl tgveislcad
    121 itrtgkvkpt ravkdqrtwt wgpcgqgail lvncdrdnle ssamdcedde vldsedlqdm
    181 slmtlstktp kdfftnhtlv lhvarsemdk vrvfqatrgk lsskcsvvlg pkwpshylmv
    241 pggkhnmdfy vealafpdtd fpglitltis lldtsnlelp eavvfqdsvv frvapwimtp
    301 ntqppqevya csifenedfl ksvttlamka kckliticpee enmddwmqd  emeigyiqap
    361 hktlpvvfds prnrglkefp ikrvmgpdfg yvtrgpqtgg isgldsfgnl evsppvtvrg
    421 keyplgrilf gdscypsnds rqmhqalqdf lsaqqvqapv klysdwlsvg hvdeflsfvp
    481 apdrkgfrll lasprscykl fqeqqneghg eallfegikk kkqqkiknil snktlrehns
    541 fvercidwnr ellkrelgla esdiidipql fklkefskae affpnmvnml vlgkhlgipk
    601 pfgpvingrc cleekvcsll eplglqctfi ndfftyhirh gevhcgtnvr rkpfsfkwwn
    661 mvp
```

What is claimed herein is:

1. A method of preventing transfusion-related acute lung injury (TRALI), the method comprising:
    contacting a blood transfusion product with an effective amount of an anti-Neutrophil Extracellular Trap (NET) compound; and
    administering the anti-NET compound-contacted blood transfusion product to a subject.

2. The method of claim 1, wherein the anti-NET compound is selected from the group consisting of:
    DNase; RNAse; a histone-degrading enzyme; an inhibitor of chromatin decondensation; an antibody against a component of a NET; an elastase inhibitor; a PAD inhibitor; and a PAD4 inhibitor.

3. The method of claim 2, wherein the PAD4 inhibitor is selected from the group consisting of:
    Cl-amidine and F-amidine.

4. The method of claim 1, wherein said effective amount of anti-NET compound is administered prophylactically.

5. The method of claim 1, wherein said effective amount of anti-NET compound is given repeatedly.

6. The method of claim 1, wherein the subject is further administered an anti-thrombotic treatment.

7. The method of claim 6, wherein the anti-thrombotic treatment is selected from the group consisting of:
    heparin; tPA; anistreplase; streptokinase; urokinase; a coumadin; warfarin; idraparinux; fondaparinux; aspirin; an adenosine diphosphate receptor inhibitor; a phosphodiesterase inhibitor; a glycoprotein IIB/IIA inhibitor; an adenosine reuptake inhibitor; and a thromboxane receptor antagonist.

* * * * *